United States Patent
Okubo et al.

(10) Patent No.: US 12,070,184 B2
(45) Date of Patent: Aug. 27, 2024

(54) IMAGING SYSTEM, ENDOSCOPE SYSTEM, AND CONTROL METHOD

(71) Applicant: OLYMPUS CORPORATION, Hachioji (JP)

(72) Inventors: Ryuhi Okubo, Hachioji (JP); Makoto Ikeda, Hachioji (JP); Satoru Adachi, Hachioji (JP); Nana Akahane, Hachioji (JP)

(73) Assignee: OLYMPUS CORPORATION, Hachioji (JP)

( * ) Notice: Subject to any disclaimer, the term of this patent is extended or adjusted under 35 U.S.C. 154(b) by 0 days.

(21) Appl. No.: 18/188,126

(22) Filed: Mar. 22, 2023

(65) Prior Publication Data
US 2023/0255444 A1    Aug. 17, 2023

Related U.S. Application Data

(63) Continuation of application No. PCT/JP2020/036454, filed on Sep. 25, 2020.

(51) Int. Cl.
*A61B 1/00* (2006.01)
*G06T 7/00* (2017.01)

(52) U.S. Cl.
CPC .... *A61B 1/000095* (2022.02); *A61B 1/00126* (2013.01); *A61B 1/00133* (2013.01); *G06T 7/0012* (2013.01); *G06T 2207/10* (2013.01)

(58) Field of Classification Search
CPC .......... A61B 1/000095; A61B 1/00126; A61B 1/00133; G06T 7/0012; G06T 2207/10
See application file for complete search history.

(56) References Cited

U.S. PATENT DOCUMENTS 10,063,764 B2 * 8/2018 Fukuda ................ H04N 23/672
2019/0076001 A1    3/2019 Tsuyuki
(Continued)

FOREIGN PATENT DOCUMENTS

CN      105163011 A      12/2015
JP      2003-101867 A    4/2003
(Continued)

OTHER PUBLICATIONS

International Search Report dated Nov. 2, 2020, issued in counterpart application No. PCT/JP2020/036454 with English translation (6 pages).

*Primary Examiner* — Georgia Y Epps
*Assistant Examiner* — Don J Williams
(74) *Attorney, Agent, or Firm* — WHDA, LLP

(57) ABSTRACT

An imaging system includes: an optical system configured to form a subject image; a driver configured to drive the optical system; an imaging element configured to capture the subject image and generate image data; and a processor configured to control the imaging element and the driver. The imaging element includes: a first imaging portion configured to capture an image of a first light beam that travels through a first optical path in the optical system; a second imaging portion configured to capture an image of a second light beam that travels through a second optical path shorter than the first optical path; and plural phase difference pixels for phase difference autofocus, the plural phase difference pixels being arranged in at least one of the first imaging portion and the second imaging portion, the plural phase difference pixels being configured to output phase difference signals.

16 Claims, 40 Drawing Sheets

(56) References Cited

U.S. PATENT DOCUMENTS

| | | |
|---|---|---|
| 2020/0015656 A1* | 1/2020 | Tsuyuki ................ A61B 1/051 |
| 2020/0029034 A1 | 1/2020 | Irie et al. |
| 2020/0077030 A1 | 3/2020 | Asukabe et al. |
| 2020/0244893 A1 | 7/2020 | Fujii |

FOREIGN PATENT DOCUMENTS

| | | |
|---|---|---|
| JP | 2008-177903 A | 7/2008 |
| JP | 2009-003122 A | 1/2009 |
| WO | 2016/038917 A1 | 3/2016 |
| WO | 2016/140066 A1 | 9/2016 |
| WO | 2017/203897 A1 | 11/2017 |
| WO | 2018/179875 A1 | 10/2018 |
| WO | 2018/180257 A1 | 10/2018 |
| WO | 2019/031000 A1 | 2/2019 |

\* cited by examiner

FIG.21
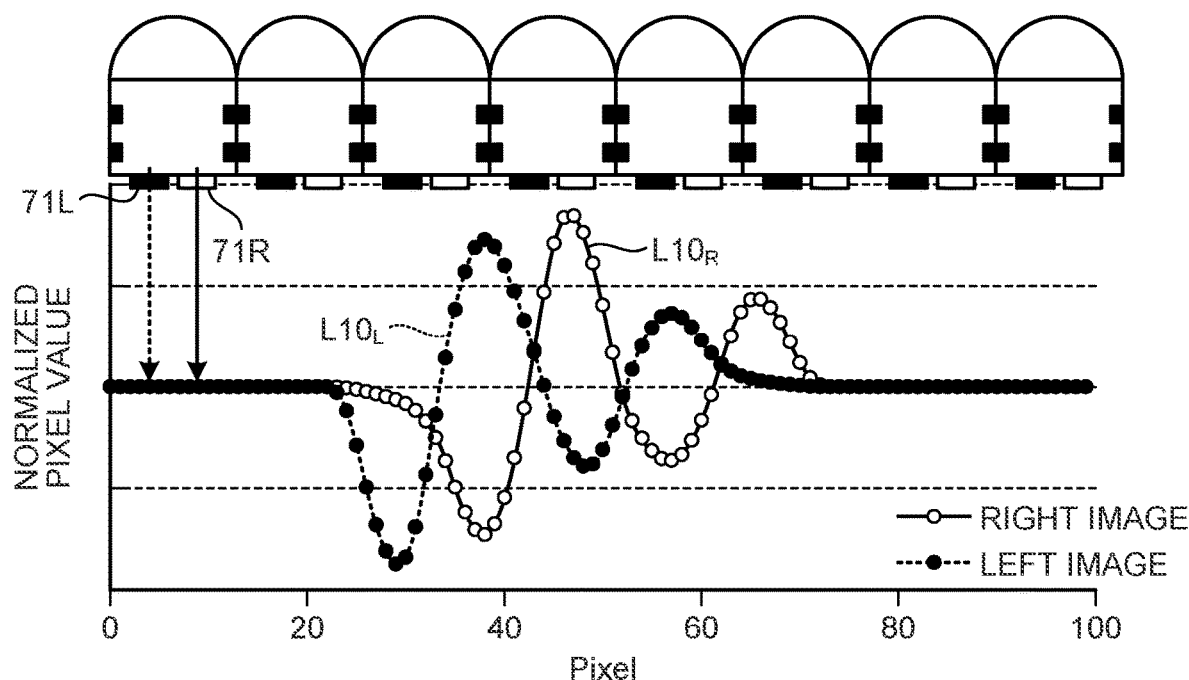
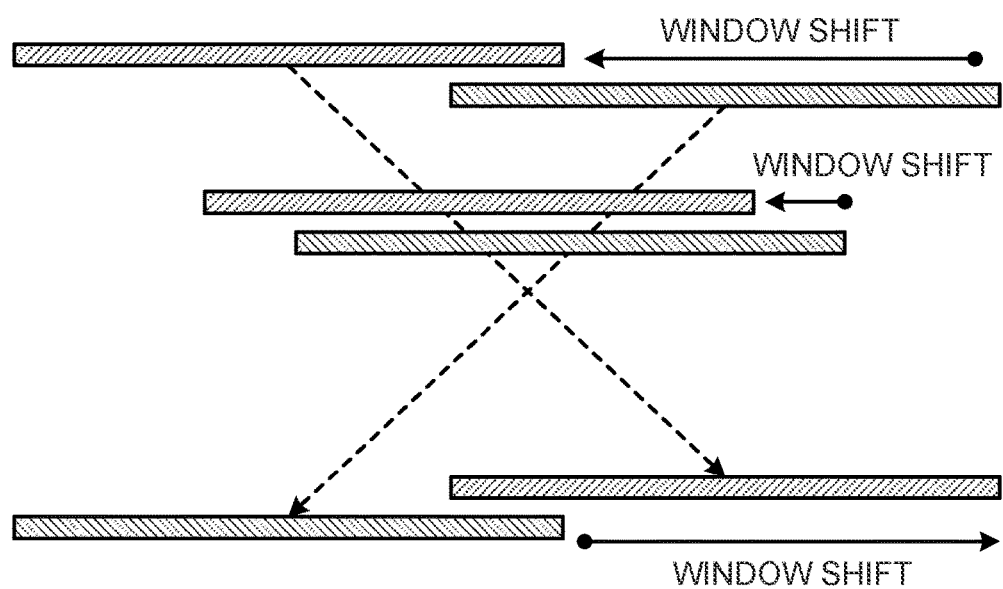

IMAGING SYSTEM, ENDOSCOPE SYSTEM, AND CONTROL METHOD

CROSS-REFERENCE TO RELATED APPLICATION

This application is a continuation of International Application No. PCT/JP2020/036454, filed on Sep. 25, 2020, the entire contents of which are incorporated herein by reference.

BACKGROUND

1. Technical Field

The present disclosure relates to an imaging system, an endoscope system, and a control method.

2. Related Art

In recent years, attempts have been made to: increase the numbers of pixels in imaging elements for endoscopes for the purpose of increasing the number of pixels in images; and downsize the imaging elements for the purpose of achieving minimally invasive treatment of subjects. Accordingly, recent endoscopes have imaging elements with pixels smaller in size and optical systems are made brighter (F-numbers are made smaller) in consideration of their diffraction limits for the purpose of maintaining resolution. However, endoscopes with brighter optical systems have smaller depths of field.

In a known technique, a space division extension of depth of field (EDOF) optical system that forms two optical images that are focused on different positions in the same plane by use of one objective optical system is thus used (see, for example, International Publication WO No. 2017/203897). In this technique: a light beam incident from the objective optical system is split into a reflected light beam and a transmitted light beam by a first surface of a splitter element arranged on the image side of the objective optical system; this transmitted light beam is reflected by a second surface of the splitter element and formed into a first optical image; and the reflected light beam is reflected toward the first surface by a mirror arranged on an optical path and transmitted through the first surface, and is thereby formed into a second optical image.

Furthermore, a focus detecting device for an imaging element has been known in recent years (see, for example, Japanese Unexamined Patent Application Publication No. 2009-003122). This focus detecting device has, arranged therein, a phase difference pixel for PD light shielding autofocus (AF) or a phase difference pixel for PD division AF having the pixel's light receiving surface divided. Part of a PD unit of the phase difference pixel for PD light shielding AF is shielded from light and a light beam incident on the phase difference pixel for PD light shielding AF has been stopped down. The focus detecting device captures a subject image formed by an imaging optical system and detects a focus of the imaging optical system by a pupil division phase difference method. In this focus detecting device using the pupil division phase difference method, a stop that has been provided for each phase difference pixel or a PD unit that has been provided for each phase difference pixel and plurally divided receives a pair of light beams, thereby divides the exit pupil of the imaging optical system to a left half and a right half (or a top half and a bottom half), and an image interval between two images formed by the light beams that have passed through these pupils is thereby found. This image interval and the barycentric angular interval (AF sensitivity) upon the pupil division are used for conversion into a defocus amount (an amount by which a defocus lens is driven). This AF process enables adjustment of the focus position of the optical system.

SUMMARY

In some embodiments, an imaging system includes: an optical system configured to form a subject image of an object; a driver configured to drive the optical system along an optical axis; an imaging element configured to capture the subject image and generate image data; and a processor configured to control the imaging element and the driver, the imaging element including: a first imaging portion that includes plural pixels each having a photoelectric converter, the first imaging portion being configured to capture an image of a first light beam that travels through a first optical path in the optical system; a second imaging portion that includes plural pixels each having a photoelectric converter, the plural pixels being arranged in a two-dimensional matrix, the second imaging portion being configured to capture an image of a second light beam that travels, via part of the first optical path, through a second optical path shorter than the first optical path; and plural phase difference pixels for phase difference autofocus, the plural phase difference pixels being arranged in at least one of the first imaging portion and the second imaging portion, the plural phase difference pixels being configured to output phase difference signals by receiving a pair of light beams resulting from pupil division of a light beam that passes through the optical system, and the processor being configured to calculate an interval between two images based on the phase difference signal, generate a combined image resulting from combination of a first image obtained by the first imaging portion and a second image obtained by the second imaging portion, and drive the driver to cause the optical system to be focused on the object for the combined image based on the interval between two images.

In some embodiments, an endoscope system includes: an endoscope including an insertion portion to be inserted into a subject; and a controller to which the endoscope is detachably connected. The endoscope including: an optical system configured to form a subject image of an object; a driver configured to drive the optical system along an optical axis; and an imaging element configured to capture the subject image and generates image data, the controller includes a processor configured to control the imaging element and the driver, the imaging element including: a first imaging portion that includes plural pixels each having a photoelectric converter, the plural pixels being arranged in a two-dimensional matrix, the first imaging portion being configured to capture an image of a first light beam that travels through a first optical path in the optical system; a second imaging portion that includes plural pixels each having a photoelectric converter, the plural pixels being arranged in a two-dimensional matrix, the second imaging portion being configured to capture an image of a second light beam that travels, via part of the first optical path, through a second optical path shorter than the first optical path; and plural phase difference pixels for phase difference autofocus, the plural phase difference pixels being arranged in at least one of the first imaging portion and the second imaging portion, the plural phase difference pixels being configured to output phase difference signals that are able to be used in detection of the object by receiving a pair of light beams resulting from pupil division of a light beam that passes through the optical system, and the processor being configured to calculate an interval between two images based on the phase difference signal, generate a combined image resulting from combination of a first image obtained by the first imaging portion and a second image obtained by the second imaging portion, and drive the driver to cause the optical system to be focused on the object for the combined image based on the interval between two images.

In some embodiments, provided is a control method executed by a controller configured to control an imaging device including: an optical system configured to form a subject image of an object; a driver configured to drive the optical system along an optical axis; and an imaging element configured to capture the subject image and generate image data, the imaging element including: a first imaging portion that includes plural pixels each having a photoelectric converter, the plural pixels being arranged in a two-dimensional matrix, the first imaging portion being configured to capture an image of a first light beam that travels through a first optical path in the optical system; a second imaging portion that includes plural pixels each having a photoelectric converter, the plural pixels being arranged in a two-dimensional matrix, the second imaging portion being configured to capture an image of a second light beam that travels, via part of the first optical path, through a second optical path shorter than the first optical path; and plural phase difference pixels for phase difference autofocus, the plural phase difference pixels being arranged in at least one of the first imaging portion and the second imaging portion, the plural phase difference pixels being configured to output phase difference signals that are able to be used in detection of the object by receiving a pair of light beams resulting from pupil division of a light beam that passes through the optical system. The control method includes: calculating an interval between two images based on the phase difference signal; generating a combined image resulting from combination of a first image obtained by the first imaging portion and a second image obtained by the second imaging portion; and driving the driver to cause the optical system to be focused on the object for the combined image based on the interval between two images.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 21 is a diagram schematically illustrating phase difference signals of right-open phase difference pixels and left-open phase difference pixels, according to the first embodiment;

DETAILED DESCRIPTION

Embodiments of the present disclosure will hereinafter be described in detail, together with the drawings. The present disclosure is not limited by the following embodiments. Furthermore, the drawings referred to in the following description schematically illustrate shapes, sizes, and positional relations merely to an extent that allows substance of the present disclosure to be understood. That is, the present disclosure is not limited only to the shapes, sizes, and positional relations exemplified by the drawings. In addition, endoscope systems each including a flexible endoscope will hereinafter be described as medical systems each including an autofocus system according to the present disclosure, but without being limited to these endoscope systems, the present disclosure is also applicable to an endoscope system including a rigid endoscope. Of course, an autofocus system according to the present disclosure is also applicable to a medical operating microscope system. What is more, an autofocus system according to the present disclosure is not limited to medical uses, but is also applicable to industrial uses.

First Embodiment

Configuration of Endoscope System

Figure 1:
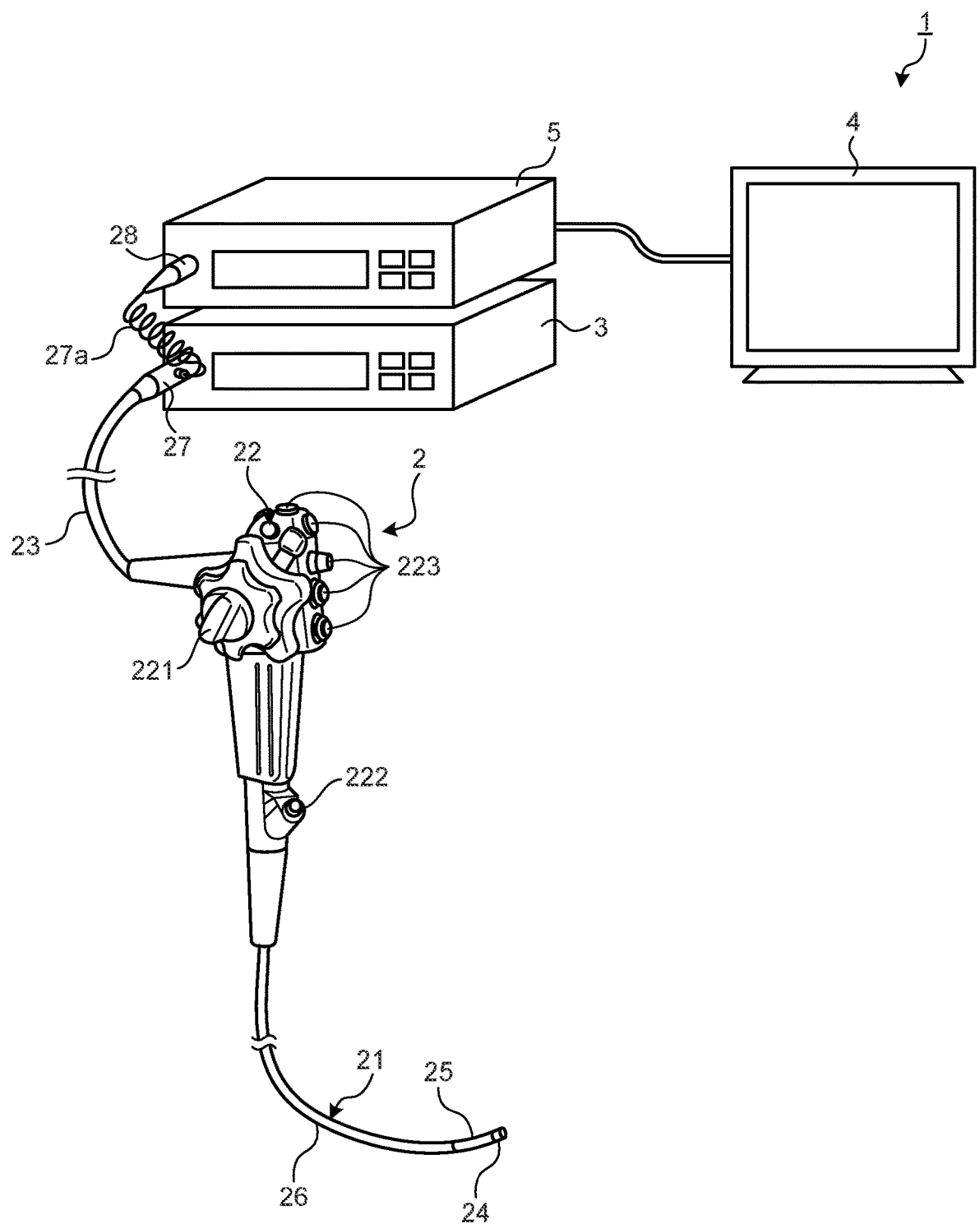
FIG. 1 is a schematic diagram illustrating a schematic configuration of an endoscope system according to a first embodiment.
Figure 2:
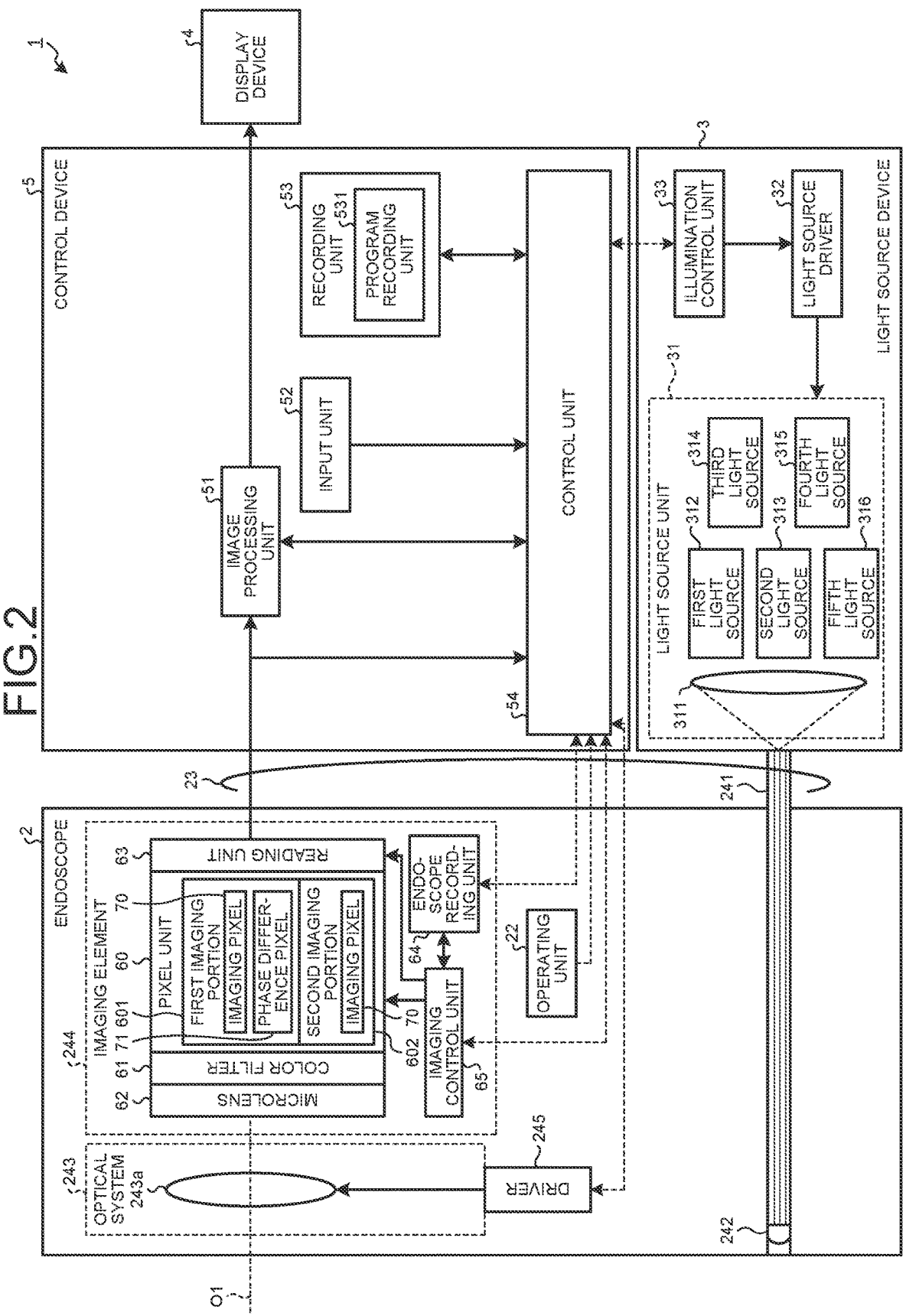
FIG. 2 is a block diagram illustrating a functional configuration of main parts of the endoscope system according to the first embodiment.

FIG. 1 is a schematic diagram illustrating a schematic configuration of an endoscope system according to a first embodiment. FIG. 2 is a block diagram illustrating a functional configuration of main parts of the endoscope system according to the first embodiment.

An endoscope system 1 illustrated in FIG. 1 and FIG. 2 is for: capturing an image of the interior of the body of a subject, such as a patient, through insertion into the body of the subject; and displaying a display image based on data on the image captured. A user, such as a medical doctor, examines the presence of any bleeding site, tumor site, and anomaly site and measures a size of any of these sites, by observing the display image. The endoscope system 1 includes an endoscope 2, a light source device 3, a display device 4, and a control device 5.

Configuration of Endoscope

A configuration of the endoscope 2 will be described first.

By capturing an image of the interior of the body of a subject, the endoscope 2 generates image data (RAW data) and outputs the generated image data to the control device 5. The endoscope 2 includes an insertion portion 21, an operating unit 22, and a universal cord 23.

The insertion portion 21 has an elongated shape having flexibility. The insertion portion 21 has: a distal end portion 24 having an imaging element 244 described later and built therein; a bending portion 25 including plural bending pieces and freely bendable; and a flexible tube portion 26 that is connected to a proximal end of the bending portion 25, has flexibility, and is elongated.

The distal end portion 24 is configured by use of, for example, glass fiber. The distal end portion 24 has a light guide 241 forming a light guiding path for light supplied from the light source device 3, an illumination lens 242 provided at a distal end of the light guide 241, an optical system 243 that condenses reflected light from a subject, an imaging element 244 arranged at an image forming position of the optical system 243, and a driver 245 that causes the optical system 243 to move along an optical axis O1.

The illumination lens 242 is configured by use of one or plural lenses and outputs light supplied from the light guide 241, to the outside.

The optical system 243 is configured by use of plural lenses, condenses reflected light reflected by a subject, and forms a subject image on an imaging surface of the imaging element 244.

Detailed Configuration of Optical System

Figure 3:
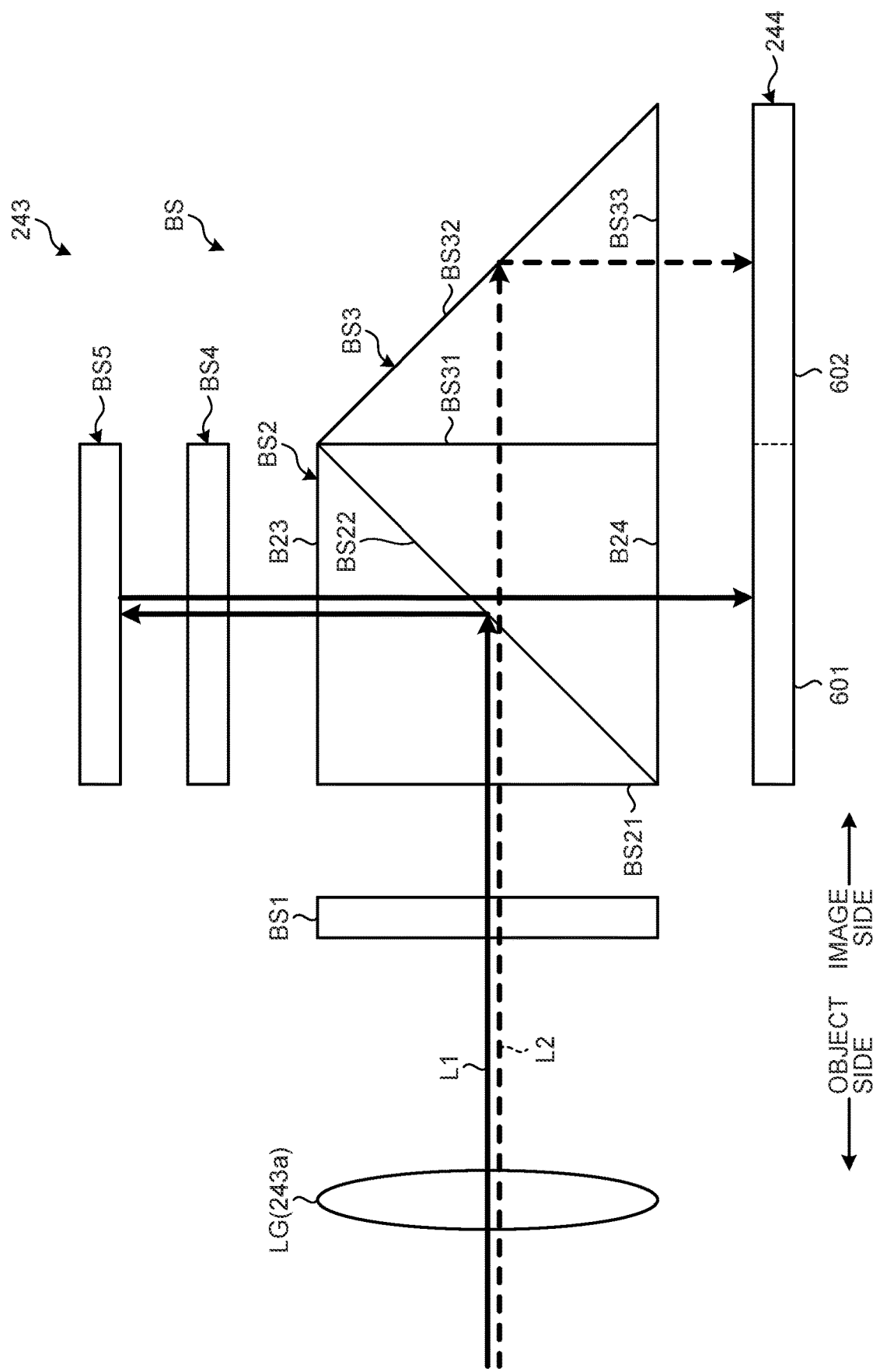
FIG. 3 is a schematic diagram illustrating a configuration of an optical system according to the first embodiment.
Figure 4:
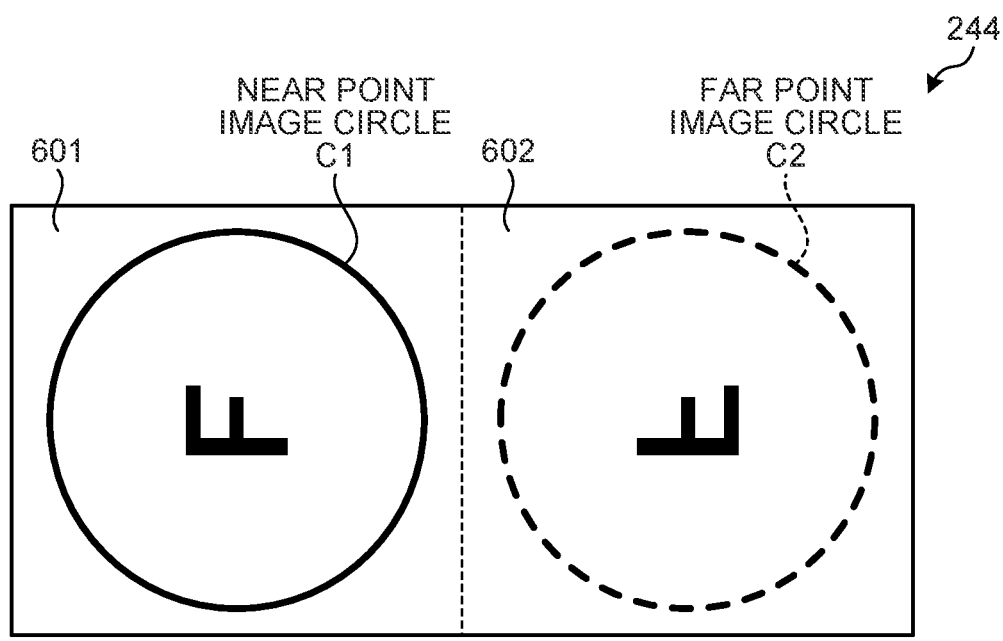
FIG. 4 is a schematic diagram of image circles formed on an imaging surface of an imaging element according to the first embodiment.

A detailed configuration of the optical system 243 will now be described. FIG. 3 is a schematic diagram illustrating a configuration of the optical system 243. FIG. 4 is a schematic diagram of image circles formed on the imaging surface of the imaging element 244.

The optical system 243 illustrated in FIG. 3 has a lens group LG and an optical path splitter unit BS. The left side in FIG. 3 will be referred to as an object side and the right side as an image side. For convenience of explanation, with respect to FIG. 3 and hereinafter, only one focus lens 243a of the lens group LG including plural lenses will be used in the explanation.

The lens group LG is implemented by use of the plural lenses and an aperture diaphragm. The lens group LG outputs a light beam (a subject image) condensed from a predetermined visual field area, to the optical path splitter unit BS. The plural lenses include the focus lens 243a. The focus lens 243a is provided movably along the optical axis O1 and changes a focus position (a focal position) of the lens group LG by moving along the optical axis O1, on the basis of driving by the driver 245 described later.

The optical path splitter unit BS is arranged on an optical path of the lens group LG. The optical path splitter unit BS is arranged on the image side of the lens group LG. The optical path splitter unit BS has a ½ wavelength plate BS1, a polarization beam splitter BS2, a reflection prism BS3, a ¼ wavelength plate BS4, and a reflection mirror BS5.

The ½ wavelength plate BS1 is arranged on the optical path between the lens group LG and the polarization beam splitter BS2. The ½ wavelength plate BS1 imparts a phase difference of π (λ/2) to a light beam incident from the lens group LG, in an electric field oscillation direction (a plane of polarization) of the light beam, and outputs the resultant light beam to the polarization beam splitter BS2.

The polarization beam splitter BS2 transmits part (hereinafter referred to as the "second light beam L2") of the light beam incident from the ½ wavelength plate BS1 through a transmission and reflection surface BS22 therein and reflects the remaining light (hereinafter, referred to as the "first light beam L1") of the light beam to the ¼ wavelength plate BS4. Furthermore, the polarization beam splitter BS2 transmits the first light beam L1 incident from the ¼ wavelength plate BS4 therethrough toward the imaging element 244. In this first embodiment, the polarization beam splitter BS2 functions as an optical path splitter element and the transmission and reflection surface BS22 functions as an optical path splitter surface.

The reflection prism BS3 reflects the second light beam L2 incident from the polarization beam splitter BS2 toward the imaging element 244.

The ¼ wavelength plate BS4 is arranged on an optical path between the polarization beam splitter BS2 and the reflection mirror BS5. The ¼ wavelength plate BS4 imparts a phase difference of π/2 (λ/4) to the first light beam L1 incident from the polarization beam splitter BS2, in an electric field oscillation direction (a plane of polarization) of the first light beam L1 and outputs the resultant first light beam L1 to the reflection mirror BS5. Furthermore, the ¼ wavelength plate BS4 imparts a phase difference of π/2 (λ/4) to the first light beam L1 incident from the reflection mirror BS5, in an electric field oscillation direction (a plane of polarization) of the first light beam L1 and outputs the resultant first light beam L1 to the polarization beam splitter BS2.

The reflection mirror BS5 is arranged opposite to an optical surface BS23 of the polarization beam splitter BS2. The reflection mirror BS5 reflects the first light beam L1 incident from the ¼ wavelength plate BS4 toward the ¼ wavelength plate BS4.

As described above, the first light beam L1 and second light beam L2 illustrated in FIG. 3 travel in directions different from each other. An optical path through which the first light beam L1 travels will hereinafter be referred to as a first optical path and an optical path through which the second light beam L2 travels will hereinafter be referred to as a second optical path.

The first optical path is formed to intersect the second optical path. The second optical path is formed on an extension of the optical path of the lens group LG. In FIG. 3, the first optical path is orthogonal to the second optical path.

The first optical path has, positioned thereon, the ½ wavelength plate BS1, an optical surface BS21, the transmission and reflection surface BS22, the optical surface BS23, the ¼ wavelength plate BS4, and the reflection mirror BS5. Accordingly, the first light beam L1 is transmitted through the ½ wavelength plate BS1 and the optical surface BS21 and reflected by the transmission and reflection surface BS22. The first light beam L1 reflected by the transmission and reflection surface BS22 is transmitted through the optical surface BS23 and the ¼ wavelength plate BS4 and reflected by the reflection mirror BS5. The first light beam L1 reflected by the reflection mirror BS5 is transmitted through the ¼ wavelength plate BS4, the optical surface BS23, the transmission and reflection surface BS22, and an optical surface BS24, to be incident on a light receiving surface (see FIG. 4) of a first imaging portion 601 in the imaging element 244 described later (a near point image circle C1 in FIG. 4).

That is, reflection of light occurs twice on the first optical path, at the transmission and reflection surface BS22 and the reflection mirror BS5. Furthermore, transmission of light occurs eight times on the first optical path, through the ½ wavelength plate BS1, the optical surface BS21, the optical surface BS23, the ¼ wavelength plate BS4, the transmission and reflection surface BS22, and the optical surface BS24. As a result, the sum total of the number of times reflection occurs and the number of times transmission occurs is ten, on the first optical path.

By contrast, the second optical path has, positioned thereon, the ½ wavelength plate BS1, the optical surface BS21, the transmission and reflection surface BS22, an optical surface BS31, a reflection surface BS32, and an optical surface BS33. Accordingly, the second light beam L2 is transmitted through the ½ wavelength plate BS1, the optical surface BS21, the transmission and reflection surface BS22, and the optical surface BS33 and reflected by the reflection surface BS32. The second light beam L2 reflected by the reflection surface BS32 is transmitted through the optical surface BS33 to be incident on a light receiving surface (see FIG. 4) of a second imaging portion 602 in the imaging element 244 described later (a far point image circle C2 in FIG. 4).

That is, on the second optical path, reflection of light occurs once at the reflection surface BS32, and transmission of light occurs five times through the ½ wavelength plate BS1, the optical surface BS21, the transmission and reflection surface BS22, the optical surface BS31, and the optical surface BS33. As a result, the sum total of the number of times reflection occurs and the number of times transmission occurs is six, on the second optical path.

Therefore, in the optical system 243, the sum total (ten times) of reflection and transmission on the first optical path is more than the sum total (six times) of reflection and transmission on the second optical path.

By reference back to FIG. 1 and FIG. 2, the description of the configuration of the endoscope 2 will be continued.

The imaging element 244 is configured by use of an image sensor, such as a complementary metal oxide semiconductor (CMOS), and outputs image data (PAW data) to the control device 5 by performing imaging at a predetermined frame rate. The imaging element 244 has: a pixel unit 60 including plural pixels each having a photoelectric converter, such as a photodiode, the plural pixels being arranged in a two-dimensional matrix; a color filter 61 arranged to be layered over each light receiving surface of the pixel unit 60; microlenses 62 arranged on an upper surface of the color filter 61; a reading unit 63 that reads image signals from the pixel unit 60; an endoscope recording unit 64 that records therein various types of information related to the imaging element 244; and an imaging control unit 65 that controls the reading unit 63.

As illustrated in FIG. 4 described above, the pixel unit 60 has: the first imaging portion 601 that includes plural pixels each having a photoelectric converter, the plural pixels being arranged in a two-dimensional matrix, and captures an image of the first light beam that travels through the first optical path in the optical system 243; and the second imaging portion 602 that includes plural pixels each having a photoelectric converter, the plural pixels being arranged in a two-dimensional matrix, and captures an image of the second light beam that travels, via part of the optical system 243, through the second optical path shorter than the first optical path.

Figure 5:
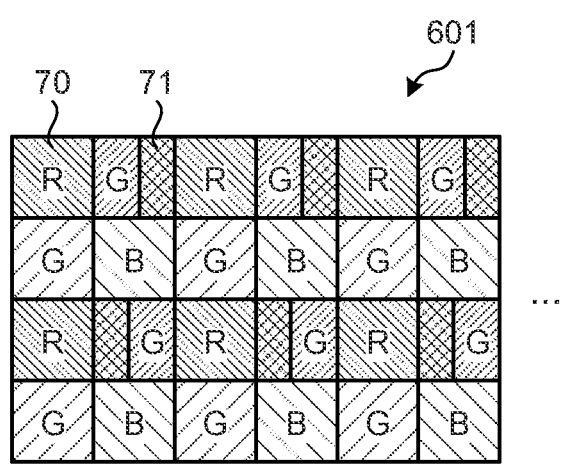
FIG. 5 is a diagram schematically illustrating a first imaging portion according to the first embodiment.
Figure 6:
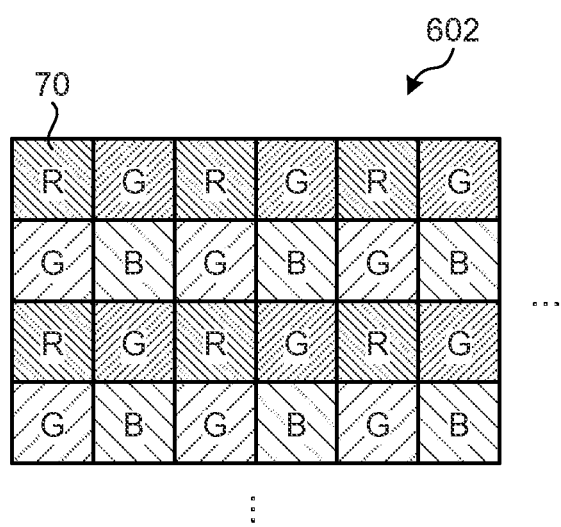
FIG. 6 is a diagram schematically illustrating a second imaging portion according to the first embodiment.

FIG. 5 is a diagram schematically illustrating the first imaging portion 601. FIG. 6 is a diagram schematically illustrating the second imaging portion 602. In FIG. 5 and FIG. 6, the first imaging portion 601 and the second imaging portion 602 are integrally formed in the imaging element 244, but without being limited to this example, they may be formed to be separately bodied.

The first imaging portion 601 will be described first.

As illustrated in FIG. 5, the first imaging portion 601 has imaging pixels 70 and phase difference pixels 71 for phase difference autofocus.

The imaging pixels 70 include plural pixels each having a photoelectric converter, the plural pixels being arranged in a two-dimensional matrix, and capture an image of the first light beam that travels through the first optical path in the optical system 243. Any one of red filters, green filters, and blue filters in the color filter 61 is arranged on each of light receiving surfaces of the imaging pixels 70. The color filter 61 has a Bayer arrangement. Any imaging pixel 70 having a red filter arranged thereon will hereinafter be referred to as an R pixel, any imaging pixel having a green filter arranged thereon as a G pixel, and any imaging pixel 70 having a blue filter arranged thereon as a B pixel.

The phase difference pixels 71 output phase difference signals (image signals) for focus detection. Specifically, the phase difference pixels 71 output phase difference signals usable for detection of an object by receiving a pair of light beams resulting from pupil division of a light beam passing through the optical system 243. The phase difference pixels 71 are arranged at predetermined intervals, in place of imaging pixels 70. For example, the phase difference pixels 71 are each arranged at the place for a green filter in a unit of the Bayer arrangement. Of course, the phase difference pixels 71 are not necessarily arranged as described above and may each be arranged in place of an imaging pixel 70 at any place. Furthermore, the phase difference pixels 71 are each not necessarily arranged at the place for a green filter in a unit of the Bayer arrangement, and may each be arranged, for example, at the place for a red filter or blue filter. Furthermore, the plural phase difference pixels 71 are each either a right-open pixel or a left-open pixel, generate a pair of left and right phase difference signals for focus detection, and outputs this pair of left and right phase difference signals. Image data in one frame generated by the imaging element 244 include image signals and phase difference signals.

Configuration of Phase Difference Pixel

A configuration of each of the phase difference pixels 71 will now be described.

Figure 7:
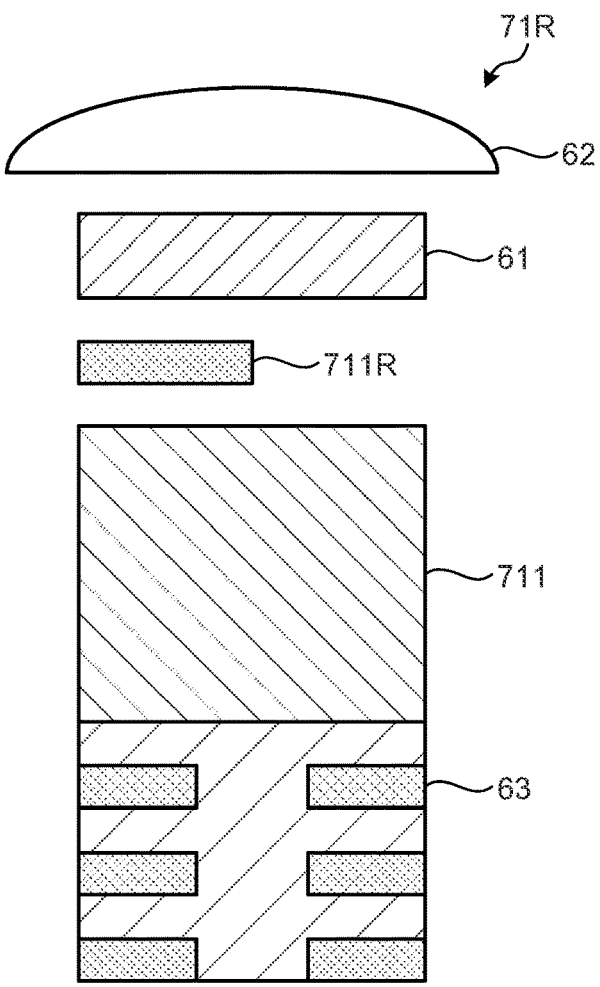
FIG. 7 is a sectional view of a right-open pixel of phase difference pixels according to the first embodiment.
Figure 8:
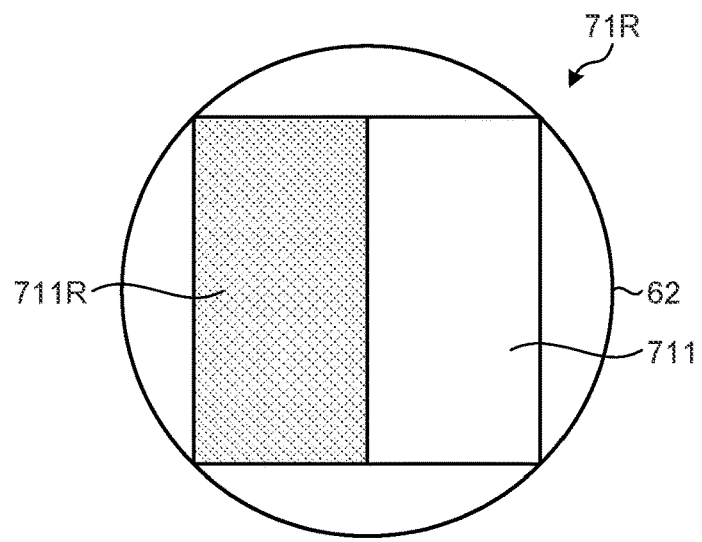
FIG. 8 is a top view of the right-open pixel of the phase difference pixels according to the first embodiment.
Figure 9:
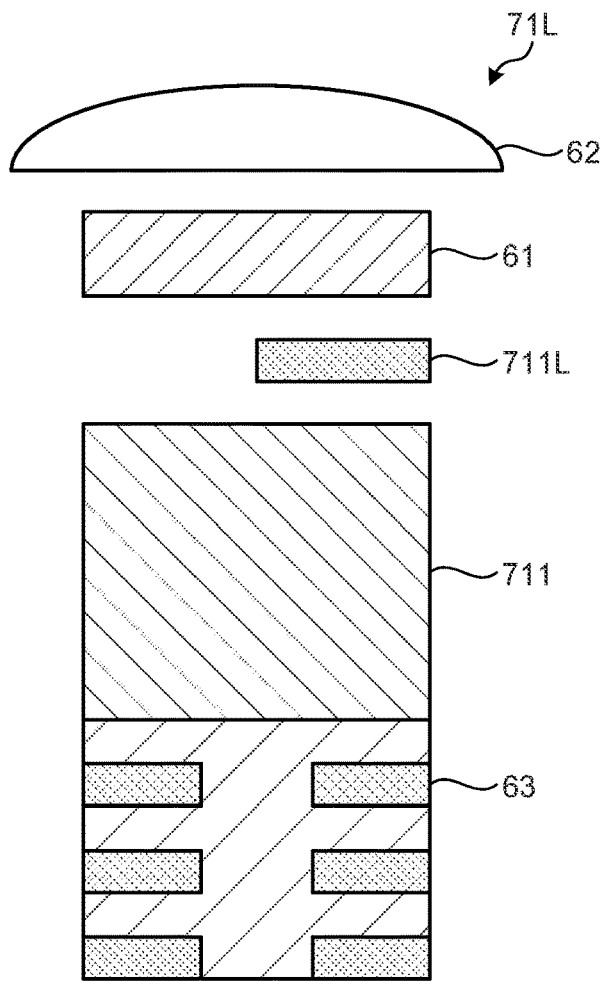
FIG. 9 is a sectional view of a left-open pixel of the phase difference pixels according to the first embodiment.
Figure 10:
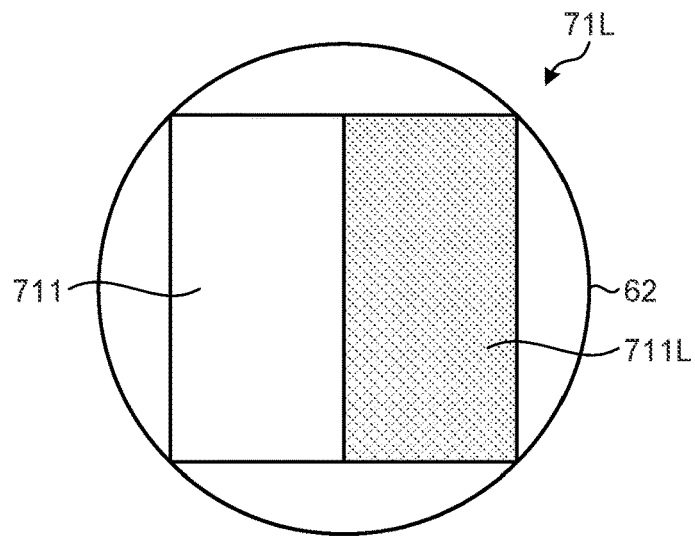
FIG. 10 is a top view of the left-open pixel of the phase difference pixels according to the first embodiment.

FIG. 7 is a sectional view of a right-open pixel of the phase difference pixels 71. FIG. 8 is a top view of the right-open pixel of the phase difference pixels 71. FIG. 9 is a sectional view of a left-open pixel of the phase difference pixels 71. FIG. 10 is a top view of the left-open pixel of the phase difference pixels 71. In a case where either a right-open phase difference pixel 71R or a left-open phase difference pixel 71L is referred to hereinafter, that pixel will simply be written as a phase difference pixel 71.

The right-open phase difference pixel 71R illustrated in FIG. 7 and FIG. 8 will be described first.

As illustrated in FIG. 7 and FIG. 8, the right-open phase difference pixel 71R includes a light receiving unit 711 that includes, for example, a photodiode, and that functions as a photoelectric conversion element, and has: a light shield 711R that blocks light incident on a left area of a light receiving surface; the color filter 61 (for example, a G filter); and a microlens 62 that have been formed to be layered over one another in this order on a top surface side of the light receiving unit 711. Furthermore, the right-open phase difference pixel 71R has a reading unit 63 that reads a right phase difference pixel signal (electric signal) from the light receiving unit 711, the reading unit 63 having been formed to be layered on a bottom surface side of the light receiving unit 711.

The left-open phase difference pixel 71L illustrated in FIG. 9 and FIG. 10 will be described next.

As illustrated in FIG. 9 and FIG. 10, the left-open phase difference pixel 71L includes a light receiving unit 711 that includes, for example, a photodiode, and that functions as a photoelectric conversion element; and has a light shield 711L that blocks light incident on a right area of a light receiving surface, the color filter 61 (for example, a G filter), and a microlens 62 that have been formed to be layered over one another in this order on a top surface side of the light receiving unit 711. Furthermore, the left-open phase difference pixel 71L has a reading unit 63 that reads a left phase difference pixel signal (electric signal) from the light receiving unit 711, the reading unit 63 having been formed to be layered on a bottom surface side of the light receiving unit 711.

The right-open phase difference pixels 71R and the left-open phase difference pixels 71L are each arranged in place of one G pixel of two G pixels of a unit of the Bayer arrangement of the color filter 61 and each unit of the Bayer arrangement (RGGB) has one of the right-open phase difference pixels 71R and left-open phase difference pixels 71L arranged therein. Furthermore, the right-open phase difference pixels 71R and the left-open phase difference pixels 71L are alternately arranged along a vertical direction of the first imaging portion 601. How the right-open phase difference pixels 71R and the left-open phase difference pixels 71L are arranged may be modified as appropriate and their arrangement intervals may thus be modified as appropriate.

The first imaging portion 601 configured as described above outputs image data per frame to the control device 5. The image data include image signals including plural electric signals generated by the imaging pixels 70 and plural pairs of left and right phase difference signals generated by the right-open phase difference pixels 71R and the left-open phase difference pixels 71L. That is, the plural right-open phase difference pixels 71R and plural left-open phase difference pixels 71L generate a pair of left and right phase difference signals for adjustment of the focal position.

The second imaging portion 602 will now be described by reference back to FIG. 6.

As illustrated in FIG. 6, the second imaging portion 602 has imaging pixels 70 only. The second imaging portion 602 captures an image of the second light beam that travels through the second optical path in the optical system 243.

By reference back to FIG. 1 and FIG. 2, the description of the configuration of the endoscope 2 will be continued.

Under control by the imaging control unit 65, the reading unit 63 reads each of image signals from the imaging pixels 70 and phase difference signals from the phase difference pixels 71 and outputs the read signals as image data to the control device 5, the imaging pixels 70 and phase difference pixels 71 being included in the first imaging portion 601. Furthermore, the reading unit 63 reads image signals from the imaging pixels 70 included in the second imaging portion 602 and outputs the read image signals as image data to the control device 5. The reading unit 63 is configured by use of, for example, a vertical scanning circuit and a horizontal scanning circuit. An A/D conversion circuit, for example, may be provided in the reading unit 63, and digital image data may be output to the control device 5.

The endoscope recording unit 64 records therein various types of information related to the endoscope 2. For example, the endoscope recording unit 64 records therein, for example, identification information identifying the endoscope 2, identification information on the imaging element 244, and reference information indicating premeasured measurement results for that particular endoscope 2. This reference information includes various types of information related to the optical system 243, AF calculation parameters, and the imaging element 244. The various types of information on the optical system 243 are, for example, information related to the focal position, magnification (focal length), diaphragm position, diaphragm diameter, exit pupil position, exit pupil diameter, focus lens position, and vignetting corresponding to image height and direction. Furthermore, information on a corrected F-number and a corrected exit pupil position that correspond to the state of the lens (optical system 243) is recorded as the AF calculation parameters. The various types of information on the imaging element 244 include position information on defective pixels. When the endoscope 2 is connected to the control device 5 described later, under control by a control unit 54, the reference information is loaded and recorded into a recording unit 53 of the control device 5 described later. Furthermore, transmission of the AF calculation parameters to the control device 5 enables calculation of information on AF sensitivity at the control unit 54. The endoscope recording unit 64 is configured by use of, for example, a non-volatile memory.

On the basis of an instruction signal or a control signal input from the control device 5, the imaging control unit 65 controls operation of the imaging element 244. Specifically, on the basis of a clock signal input from the control device 5, the imaging control unit 65 controls the frame rate and imaging timing of the imaging element 244. The imaging control unit 65 is configured by use of, for example, a timing generator.

Under control by the control device 5, the driver 245 causes the focus lens 243a of the optical system 243 to move along the optical axis O1. The driver 245 is implemented by use of, for example, a voice coil motor or a stepping motor. In this first embodiment, a configuration including at least the optical system 243, the imaging element 244, and the driver 245 functions as an imaging device.

The operating unit 22 has: a bending knob 221 that bends the bending portion 25 upward, downward, leftward, and/or rightward; a treatment tool insertion portion 222 through which a treatment tool, such as biopsy forceps, an electric knife, or an examination probe, is inserted into a body cavity; and plural switches 223 that receive peripheral device operating instruction signals and a pre-freeze signal, the peripheral device operating instruction signals being for, in addition to the light source device 3 and the control device 5, an air feeding means, a water feeding means, and a gas feeding means, the pre-freeze signal being for instructing the imaging element 244 to capture a still image. The treatment tool inserted from the treatment tool insertion portion 222 comes out from an opening (not illustrated in the drawings) via a treatment tool channel (not illustrated in the drawings) in the distal end portion 24.

The universal cord 23 has, built therein, at least the light guide 241 and an assembly cable having one or plural cables bundled together. The assembly cable is a signal line for transmission and reception of signals between the endoscope 2 and the light source device 3 and the control device 5, and includes a signal line for transmission and reception of setting data, a signal line for transmission and reception of image data, and a signal line for transmission and reception of a driving clock signal for driving the imaging element 244. The universal cord 23 has a connector 27 attachable to and detachable from the light source device 3. A coil cable 27a that is coil-shaped extends from the connector 27. A connector 28 attachable to and detachable from the control device 5 is provided at an extended end of the coil cable 27a.

Configuration of Light Source Device

A configuration of the light source device 3 will be described next.

The light source device 3 supplies illumination light to be emitted to a subject, from the distal end portion 24 of the endoscope 2. The light source device 3 includes a light source unit 31, a light source driver 32, and an illumination control unit 33.

The light source unit 31 emits at least one of: white light including light of a red wavelength band, light of a green wavelength band, and light of a blue wavelength band; and special light, to a subject. The light source unit 31 has a condenser lens 311, a first light source 312, a second light source 313, a third light source 314, a fourth light source 315, and a fifth light source 316.

The condenser lens 311 is configured by use of one or plural lenses. The condenser lens 311 condenses light emitted by each of the first light source 312, the second light source 313, the third light source 314, the fourth light source 315, and the fifth light source 316, and outputs the condensed light to the light guide 241.

The first light source 312 is configured by use of a red light emitting diode (LED) lamp. The first light source 312 emits light (hereinafter, simply referred to as "R light") of a red wavelength band (610 nm to 750 nm), on the basis of electric current supplied from the light source driver 32.

The second light source 313 is configured by use of a green LED lamp. The second light source 313 emits light (hereinafter, simply referred to as "G light") of a green wavelength band (500 nm to 560 nm), on the basis of electric current supplied from the light source driver 32.

The third light source 314 is configured by use of a blue LED lamp. The third light source 314 emits light (hereinafter, simply referred to as "B light") of a blue wavelength band (435 nm to 480 nm), on the basis of electric current supplied from the light source driver 32.

The fourth light source 315 is configured by use of a violet LED lamp. The fourth light source 315 emits light (hereinafter, simply referred to as "V light") of a violet wavelength band (for example, 400 nm to 435 nm), on the basis of electric current supplied from the light source driver 32.

The fifth light source 316 is configured by use of an amber LED lamp. The fifth light source 316 emits light (hereinafter, simply referred to as "A light") of an amber wavelength band (595 nm to 610 nm), on the basis of electric current supplied from the light source driver 32.

By supplying electric current to the first light source 312, the second light source 313, the third light source 314, the fourth light source 315, and the fifth light source 316, under control by the illumination control unit 33, the light source driver 32 causes the first light source 312, the second light source 313, the third light source 314, the fourth light source 315, and the fifth light source 316 to emit light according to an observation mode set for the endoscope system 1. Specifically, in a case where the observation mode set for the endoscope system 1 is a normal observation mode, under control by the illumination control unit 33, the light source driver 32 causes the first light source 312, the second light source 313, and the third light source 314 to emit light to output white light (hereinafter, simply referred to as "W light"). Furthermore, in a case where the observation mode set for the endoscope system 1 is a special light observation mode, under control by the illumination control unit 33, the light source driver 32 causes the second light source 313 and fourth light source 315 to emit light to output special light (hereinafter, simply referred to as "S light").

On the basis of an instruction signal received from the control device 5, the illumination control unit 33 controls the lighting timing of the light source device 3. Specifically, the illumination control unit 33 causes the first light source 312, the second light source 313, and the third light source 314 to perform output on a predetermined cycle. The illumination control unit 33 is configured by use of, for example, a central processing unit (CPU). Furthermore, in a case where the observation mode of the endoscope system 1 is the normal observation mode, by controlling the light source driver 32, the illumination control unit 33 causes the first light source 312, the second light source 313, and the third light source 314 to emit light to output W light. Furthermore, in a case where the observation mode of the endoscope system 1 is the special light observation mode, by controlling the light source driver 32, the illumination control unit 33 causes S light to be output through combination of the second light source 313 and the fourth light source 315. According to the observation mode of the endoscope system 1, by controlling the light source driver 32, the illumination control unit 33 may cause output through combination of any two or more of the first light source 312, the second light source 313, the third light source 314, the fourth light source 315, and the fifth light source 316.

Configuration of Display Device

A configuration of the display device 4 will be described next.

The display device 4 displays a display image based on image data received from the control device 5, the image data having been generated by the endoscope 2. The display device 4 displays various types of information related to the endoscope system 1. The display device 4 is configured by use of, for example, a display panel of liquid crystal or organic electroluminescence (EL).

Configuration of Control Device

A configuration of the control device 5 will be described next.

The control device 5 receives image data generated by the endoscope 2, performs predetermined image processing of the image data received, and outputs the image data processed, to the display device 4. Furthermore, the control device 5 integrally controls the overall operation of the endoscope system 1. The control device 5 includes an image processing unit 51, an input unit 52, the recording unit 53, and the control unit 54.

Under control by the control unit 54, the image processing unit 51 receives image data generated by the endoscope 2, performs predetermined image processing of the image data received, and outputs the image data processed, to the display device 4. The image processing unit 51 is configured by use of a memory and a processor having hardware, such as a graphics processing unit (GPU), a digital signal processor (DSP), or a field programmable gate array (FPGA).

The input unit 52 receives input of an instruction signal for instructing operation of the endoscope system 1 and outputs the instruction signal received, to the control unit 54. The input unit 52 is configured by use of switches, buttons, and a touch panel, for example.

The recording unit 53 records therein various programs executed by the endoscope system 1, data being executed by the endoscope system 1, and image data generated by the endoscope 2. The recording unit 53 is configured by use of a volatile memory, a non-volatile memory, and a memory card, for example. The recording unit 53 has a program recording unit 531 that records therein various programs executed by the endoscope system 1.

The control unit 54 has a memory and a processor including one or more pieces of hardware, such as at least an FPGA or a CPU. The control unit 54 controls each unit included in the endoscope system 1. On the basis of phase difference signals input from the phase difference pixels 71, the control unit 54 calculates reliability of the phase difference signals output by the phase difference pixels 71, and on the basis of the phase difference signals output by the phase difference pixels 71, calculates an interval between two images. On the basis of the reliability and the interval between two images, the control unit 54 drives the driver 245 to cause the optical system 243 to be focused on an object (subject). The reliability is any one or more of: saturation information on the phase difference pixels 71 (for example, the number of phase difference pixels 71 having saturated pixel values); a contrast value of the phase difference pixels 71 (for example, a contrast value between pixel values of the right-open phase difference pixels 71R and pixel values of the left-open phase difference pixels 71L); monotonicity of the phase difference pixels 71 (for example, monotonic increase or decrease of the image values in the area direction causes erroneous distance measurement); and the minimum correlation value. Furthermore, the control unit 54 determines whether or not the reliability of the phase difference signals output from the phase difference pixels 71 is equal to or higher than a predetermined threshold; and in a case where the control unit 54 has determined that the reliability is equal to or higher than the predetermined threshold, the control unit 54 calculates an interval between two images on the basis of the phase difference signals output from the phase difference pixels 71, and in a case where the control unit 54 has determined that the reliability is not equal to or higher than the predetermined threshold, the control unit 54 drives the driver 245 to change the focus state of the optical system 243 until the reliability is determined to be equal to or higher than the predetermined threshold. Furthermore, on the basis of the phase difference signals output from the phase difference pixels 71, the control unit 54 calculates an interval between two images, the interval representing a phase difference between two subject images in a pupil division direction of at least one of the first light beam and the second light beam, and calculates a defocus amount and a defocus direction corresponding to the interval between two images on the basis of the interval between two images. In the first embodiment, the control unit 54 functions as a processor. Furthermore, in the first embodiment, the optical system 243, the imaging element 244, and the control unit 54 function as an autofocus system.

Focus Range of Optical System

Focus ranges of the optical system 243 described above will be described next.

Figure 11:
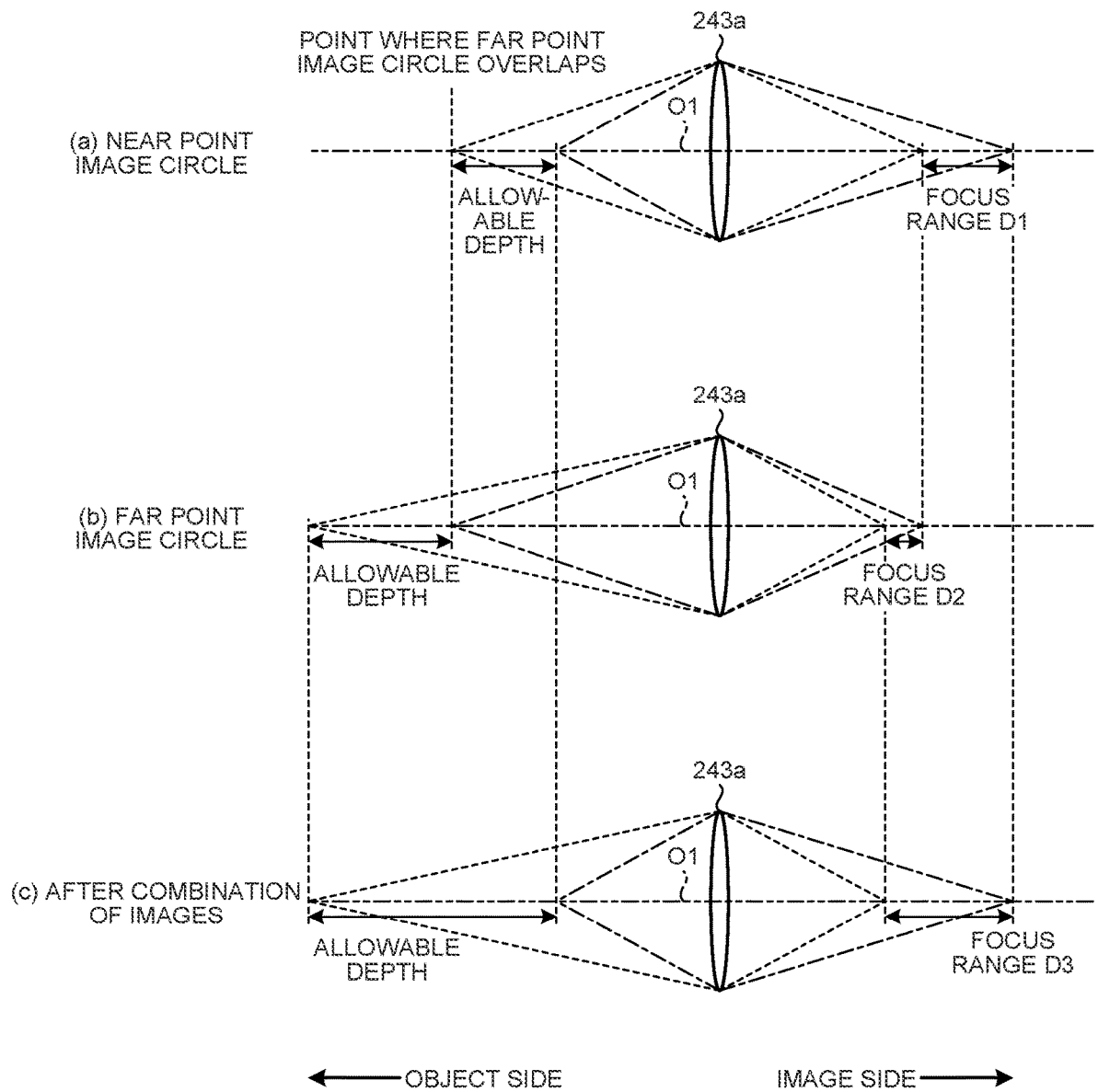
FIG. 11 is a diagram schematically illustrating focus ranges of the optical system according to the first embodiment.
Figure 12:
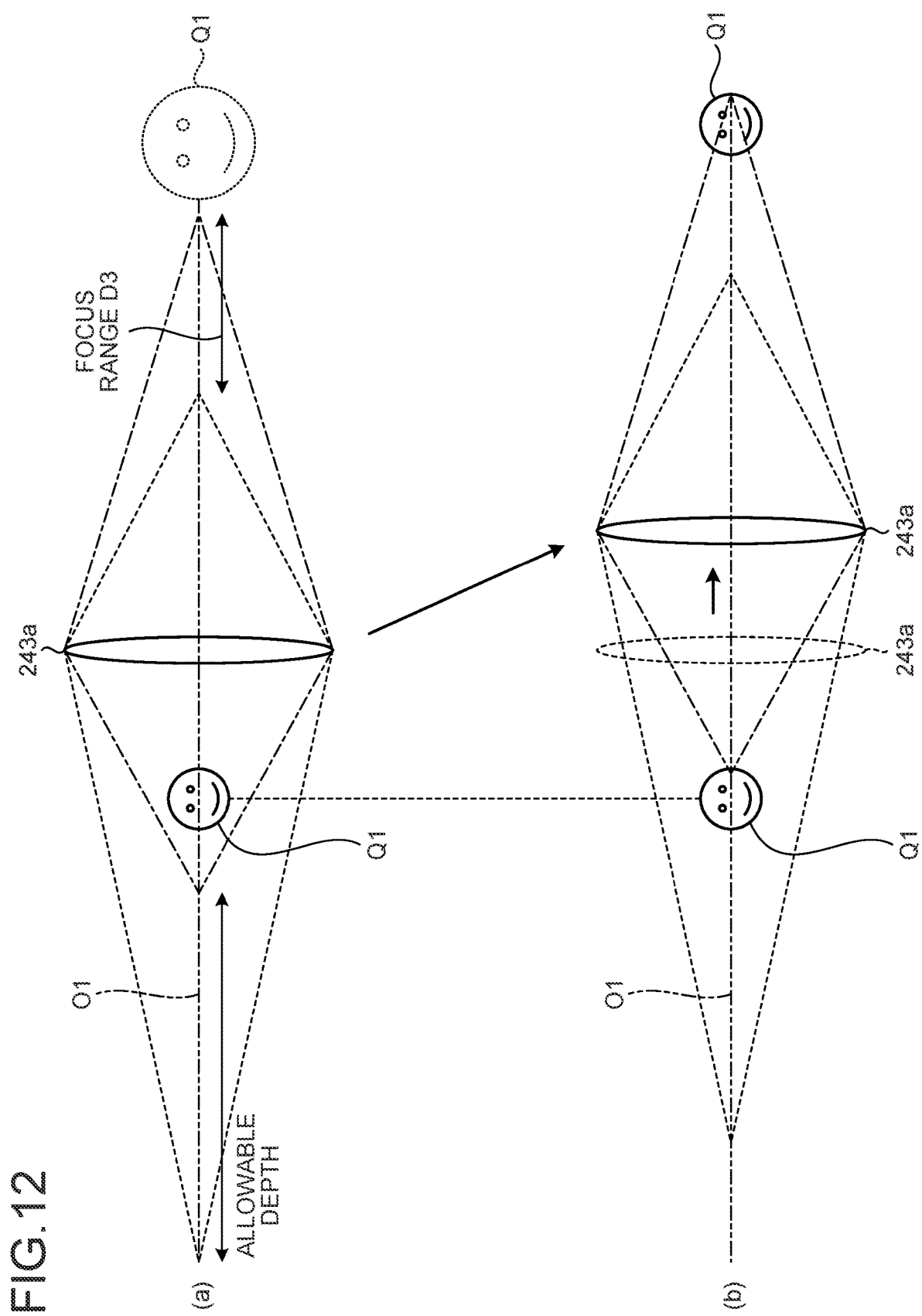
FIG. 12 is a diagram schematically illustrating a focus range of the optical system upon an AF process.

FIG. 11 is a diagram schematically illustrating the focus ranges of the optical system 243. FIG. 12 is a diagram schematically illustrating a focus range of the optical system 243 upon an AF process. In FIG. 11, from the top, (a) illustrates a focus range of the optical system 243 for the near point image circle C1 at the first imaging portion 601, (b) illustrates a focus range of the optical system 243 for the far point image circle C2 at the second imaging portion 602, and (c) illustrates a focus range of the optical system 243, the focus range resulting from virtual combination (depth combination) of image data on the near point image circle C1 and far point image circle C2. Furthermore, in FIG. 12, from the top, (a) illustrates a focus range of the optical system 243, the focus range being that before the AF process and (b) illustrates a focus range of the optical system 243, the focus range being that after the AF process.

As illustrated by (c) in FIG. 11, a focus range D3 of the optical system 243, the focus range D3 resulting from the combination of the image data on the near point image circle C1 and far point image circle C2, becomes a range (depth enlargement range) resulting from enlargement of a depth of focus ranges D1 and D2 of the near point image circle C1 and far point image circle C2 (D3=D1+D2). In this case, as illustrated in FIG. 12, even if the optical system 243 is in a state of being defocused on a subject Q1 (object), movement of the focus lens 243*a* along the optical axis O1 through drive of the driver 245 by the control unit 54 enables the depth of focus to be increased and thus the focus range to be set on at least one of the near point image circle C1 and the far point image circle C2 (see (a) of FIG. 12 to (b) of FIG. 12.

That is, in this first embodiment, on the basis of phase difference signals output from the phase difference pixels 71 of the first imaging portion 601, the control unit 54 calculates reliability of the phase difference signals and an interval between two images and performs control of changing the focus state of the optical system 243 to be focused by driving the driver 245 on the basis of the interval between two images to cause the focus lens 243*a* of the optical system 243 to move along the optical axis O1.

Outline of Pupil Division Phase Difference Method

An outline of a pupil division phase difference method will be described next.

Figure 13:
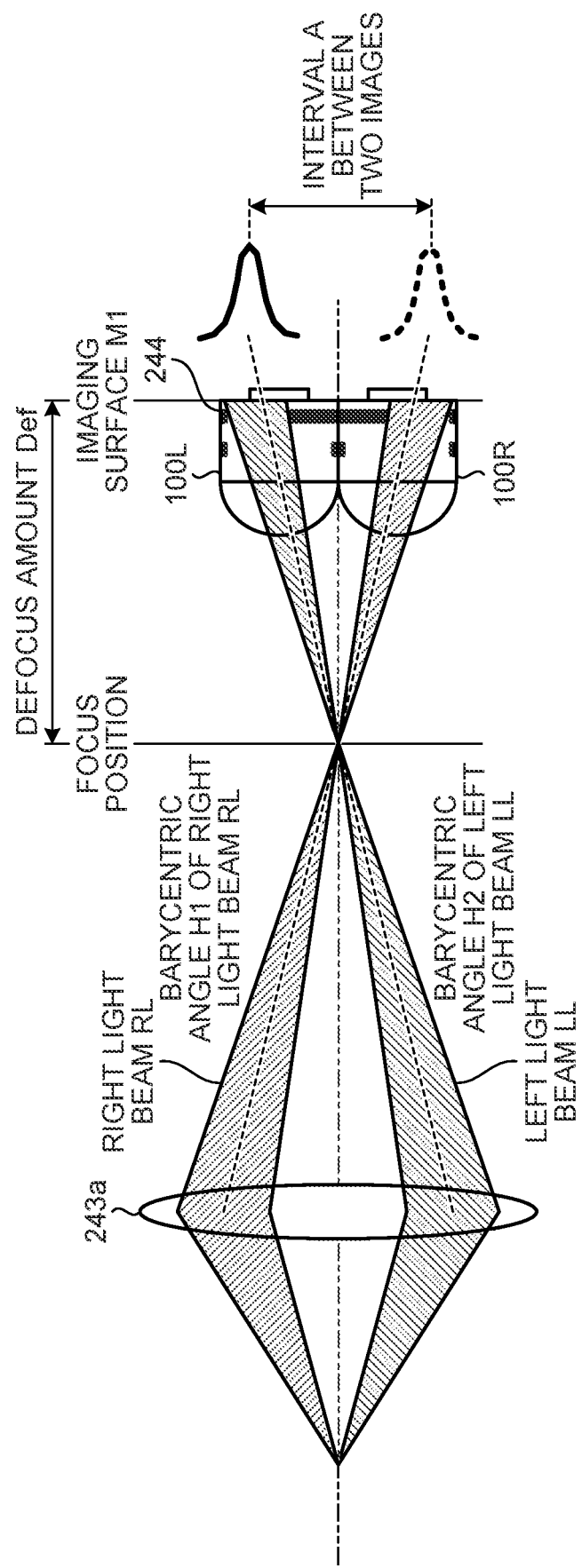
FIG. 13 is a diagram illustrating how a right light beam and a left light beam enter the imaging surface in a pupil division phase difference method.

FIG. 13 is a diagram illustrating how a right light beam and a left light beam enter the imaging surface in the pupil division phase difference method. In the pupil division phase difference method, an optical path from a subject is divided, for example, to the right and left at an exit pupil to cause a light beam from the right (right light beam RL) and a light beam from the left (left light beam LL) to be incident on an imaging surface M1 (light receiving surface) of the imaging element 244. That is, in the pupil division phase difference method, a pixel (hereinafter, referred to as the "R pixel 100R") that receives the right light beam and a pixel (hereinafter, referred to as the "L pixel 100L") that receives the left light beam are provided in the imaging element 244, and images of the right light beam RL and the left light beam LL are separately formed on the imaging surface M1 of the R pixel 100R and L pixel 100L.

In FIG. 13, a right image resulting from the right light beam RL incident via the optical system 243 (lens) is acquired by the R pixel 100R, and a left image resulting from the left light beam LL is acquired by the L pixel 100L. The amount and direction of displacement between these right image and left image on the imaging surface M1 correspond to the defocus amount and defocus direction.

A distance between a barycentric angle H1 and a barycentric angle H2 on the imaging surface M1 is an interval A between two images, the barycentric angle H1 being determined by the right light beam RL and light receiving sensitivity of the R pixel 100R described later, the barycentric angle H2 being determined by the left light beam and light receiving sensitivity of the L pixel 100L described later. This interval A between two images is proportional to the distance (defocus amount) between the imaging surface M1 and the focus. The coefficient of this proportionality is AF sensitivity. Therefore, where the AF sensitivity in FIG. 13 is a, a defocus amount Def is able to be expressed by Equation (1) below.

$$\text{Def} = \alpha \times A \quad (1)$$

Figure 14:
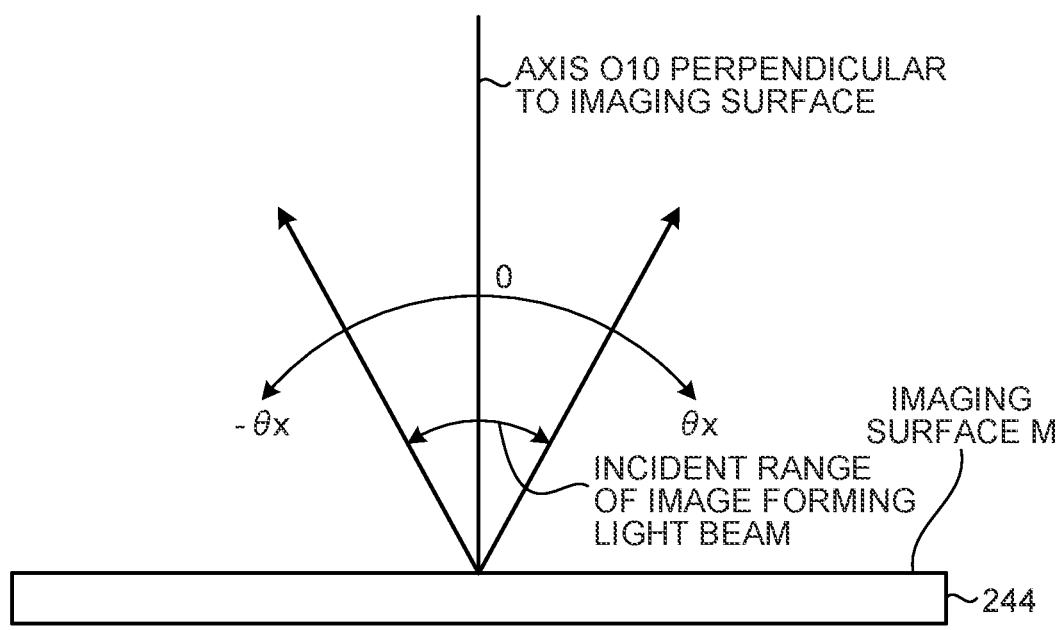
FIG. 14 is a diagram illustrating a range of incident angle along a pupil division direction of a light beam incident on a light receiving surface.

A relation between a light receiving sensitivity characteristic and image forming light beam incident angle will be described next. FIG. 14 is a diagram illustrating a range of incident angle (light ray incident angle θx) in a pupil division direction of a light beam (image forming light beam) incident on a light receiving surface.

As illustrated in FIG. 14, with an axis O10 being at 0 degrees, the axis O10 being perpendicular to the imaging surface M1 (light receiving surface), a light ray incident angle θx is represented by an angle in a positive or negative direction between the axis O10 perpendicular to the imaging surface M1 and a light ray incident angle.

Figure 15A:
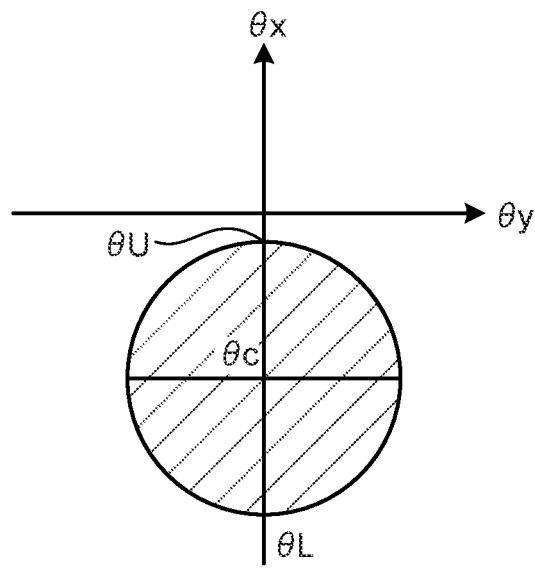
FIG. 15A is an explanatory diagram for explanation of an effective aperture for an incident light beam incident on a focus detecting pixel having a lateral image height X.
Figure 15B:
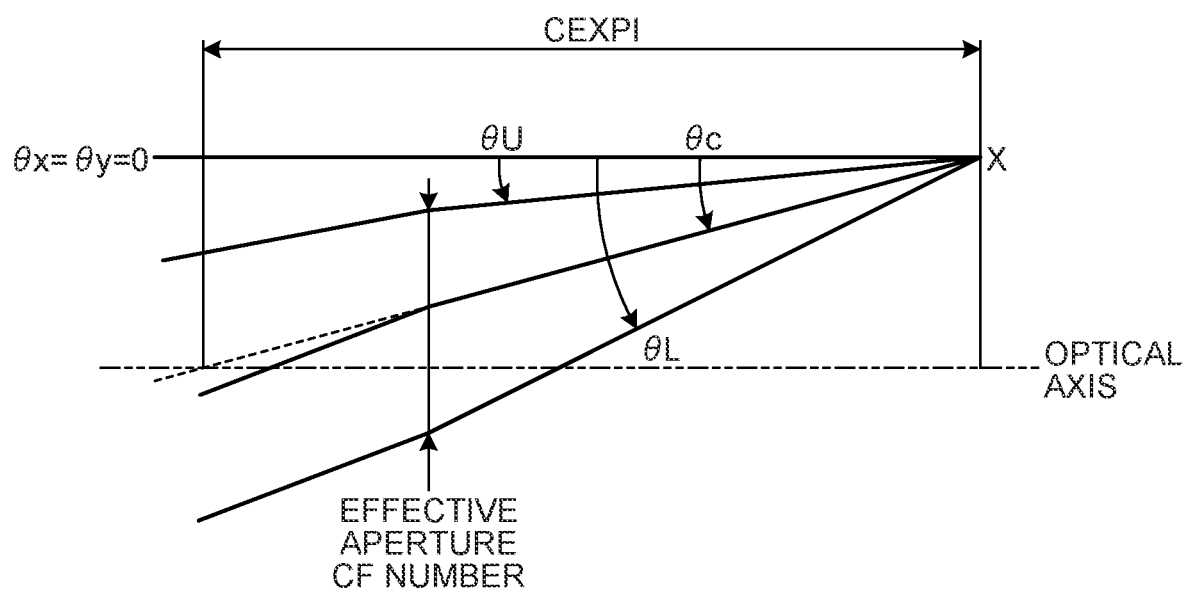
FIG. 15B is an explanatory diagram for explanation of image forming light beam incident angle that is along the center of an image forming light beam.

FIG. 15A is an explanatory diagram for explanation of an effective aperture (corrected F-number) for an incident light beam incident on a focus detecting pixel having a lateral image height X. FIG. 15B is an explanatory diagram for explanation of image forming light beam incident angle θc that is along the center of an image forming light beam.

As illustrated in FIG. 15A and FIG. 15B, the light ray incident angle on the imaging surface M1 (light receiving surface) corresponds, one on one, to the position of an intersection between a light ray W10 (a broken line in FIG. 15B) passing the center of the image forming light beam and an optical axis. The proportion of change in this position is smaller than the proportion of change in the image forming light beam incident angle θc. Therefore, using information on this position instead of information on the image forming light beam incident angle θc enables precise control with a comparatively small number of bits. In this first embodiment, this position, that is, the position at which a straight line passing the center of an image forming light beam intersects the optical axis will hereinafter be referred to as the corrected exit pupil position (CEXPI). This may be different from an exit pupil position defined ordinarily as a paraxial amount. Furthermore, the corrected exit pupil position (CEXPI) can be expressed by Equation (2) below and the corrected F-number (CF number) can be expressed by Equation (3) below.

$$\text{Tan } \theta c = (\text{Tan } \theta U + \text{Tan } \theta L)/2 \quad (2)$$

$$\text{CEXPI} = x/\text{Tan } \theta c$$

$$\text{CF value} = \text{Tan } \theta L - \text{Tan } \theta U \quad (3)$$

Figure 16:
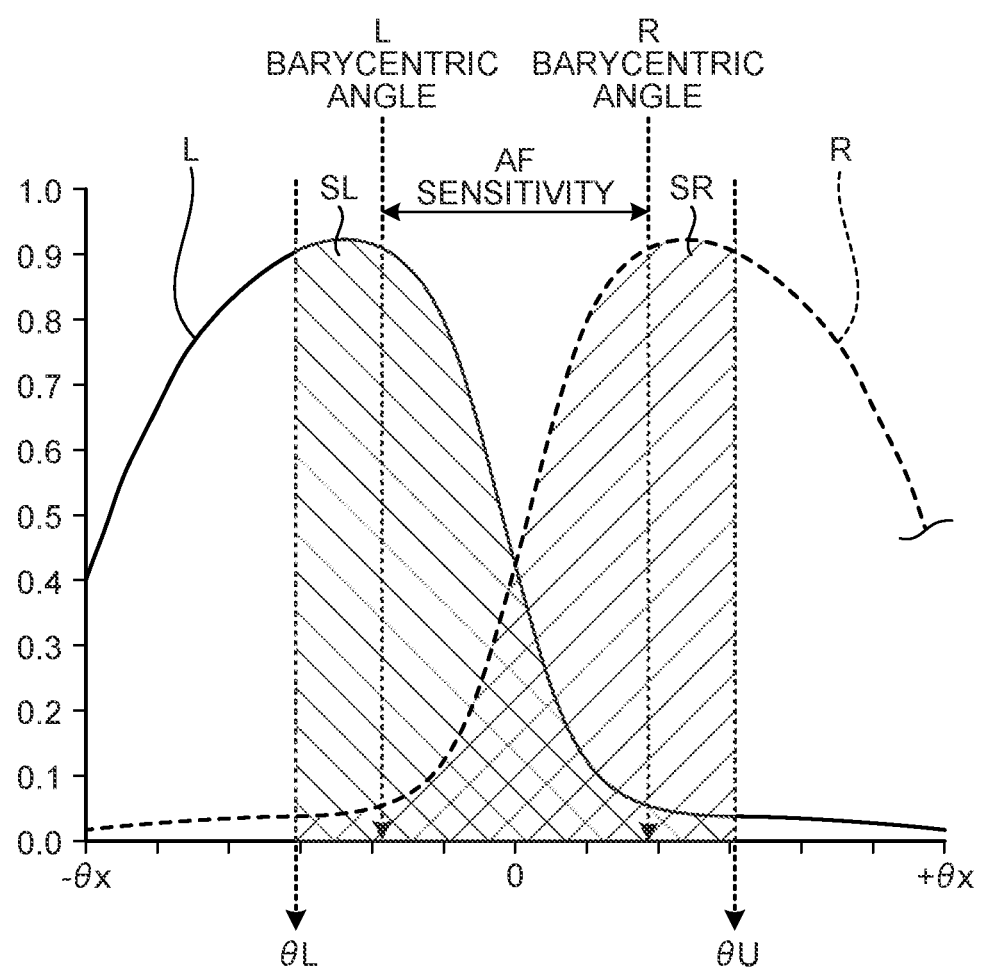
FIG. 16 is a diagram illustrating, with a solid line and a broken line, characteristics of light receiving sensitivity of a pixel that receives a left light beam that has been transmitted through a left pupil and a pixel that receives a right light beam that has been transmitted through a right pupil, with the horizontal axis representing light ray incident angle and the vertical axis representing the light receiving sensitivity.

FIG. 16 is a diagram illustrating, with a solid line L and a broken line R, characteristics of reception sensitivity of the L pixel 100L that receives the left light beam transmitted through the left pupil and the R pixel 100R that receives the right light beam transmitted through the right pupil, with the horizontal axis representing the light ray incident angle θ and the vertical axis representing the light receiving sensitivity. FIG. 16 illustrates light receiving sensitivity characteristics of phase difference pixels 71 (focus detecting pixels) positioned on the optical axis and the light receiving sensitivity characteristics of the L pixel 100L and R pixel 100R are substantially bilaterally symmetric about a light ray incident angle of 0.

The light receiving sensitivity of the phase difference pixels 71 (focus detecting pixels) has angular characteristics in the pupil division direction. In the first embodiment, AF sensitivity is calculated from the angle ranges of the image forming light beams and the angular characteristics of the focus detecting pixels. That is, in the first embodiment, as AF calculation parameters for obtaining appropriate AF sensitivity, information on the sensitivity of the L pixel 100L and R pixel 100R and information (the corrected F-numbers representing the widths of the light beams and the corrected exit pupil positions representing the slopes of the light beams) related to the angle ranges of the image forming light beams incident on the L pixel 100L and R pixel 100R are used.

The AF sensitivity will be described now.

In this first embodiment, for simplification of calculation, a range of a light beam incident on a phase difference pixel 71 (focus detecting pixel) is found by use of a corrected F-number and information on a corrected exit pupil position, and AF sensitivity is thereby found. In this case, the incident angle of the image forming light beam incident on the imaging surface M1 (light receiving surface) at a predetermined image height is influenced by, for example, aberration in the optical system 243 between the diaphragm and the imaging surface M1 (light receiving surface), and thus differs depending on the optical system 243. In this embodiment, information on the image forming light beam incident angle corresponding to the image height on the imaging surface M1 (light receiving surface) is an AF calculation parameter, the information being obtained in the optical system 243.

FIG. 16 is an explanatory diagram for explanation of relations between: light receiving sensitivity of the phase difference pixels 71 and the incident angle ranges of the image forming light beams; and AF sensitivity. The solid line L represents the light receiving sensitivity of the L pixel 100L and the broken line R represents the light receiving sensitivity of the R pixel 100R. It is assumed that image forming light beams are incident on the phase difference pixels 71 in the angle ranges indicated by thick broken lines, the phase difference pixels 71 having the sensitivity characteristics illustrated in FIG. 16. That is, FIG. 16 illustrates that the image forming light beams are incident in only the angle ranges corresponding to the corrected F-number (CF number), with the image forming light beam incident angles θc being at the center.

The amount of light received by the L pixel 100L can be represented by a shaded area in FIG. 16. Furthermore, the amount of light received by the R pixel can be represented by a shaded area in FIG. 16. The barycentric position of the shaded area in FIG. 16 can be considered to correspond to the incident direction of the left light beam and the barycentric position of the shaded area in FIG. 16 can be considered to correspond to the incident direction of the right light beam. The angular interval between these barycentric positions (barycentric angular interval) is considered to be proportional to the AF sensitivity.

That is, barycentric angular intervals GL and GR can be expressed by Equations (4) and (5) below and AF sensitivity can be expressed by Equation (6) below in which barycentric angular interval is multiplied by a predetermined constant A. Herein, fL and fR are respectively light receiving sensitivity characteristics of L and R pixels. In actuality, as represented by a shaded area in FIG. 15A, a light beam is two-dimensional with θx and θy, and the barycentric angular interval GL is thus expressed by Equation (7) below (since the same applies to the barycentric angular interval GR, explanation thereof will be omitted).

$$GL = \frac{\int_{\theta L}^{\theta U} f_L(\theta x) \cdot \theta x \cdot d\theta x}{\int_{\theta L}^{\theta U} f_L(\theta x) \cdot d\theta x} \quad (4)$$

$$GR = \frac{\int_{\theta L}^{\theta U} f_R(\theta x) \cdot \theta x \cdot d\theta x}{\int_{\theta L}^{\theta U} f_R(\theta x) \cdot d\theta x} \quad (5)$$

$$AF \text{ sensitivity} = |GL - GR| \times A \quad (A \text{ is a constant}) \quad (6)$$

$$GL = \frac{\int\int_{\theta L}^{\theta U} f_L(\theta x, \theta y) \cdot \theta x \cdot \theta y \cdot d\theta x \cdot d\theta y}{\int\int_{\theta L}^{\theta U} f_L(\theta x, \theta y) \cdot d\theta x \cdot d\theta y} \quad (7)$$

FIG. 16 illustrates the light receiving sensitivity characteristics of the focus detecting pixels on the axis but the light receiving sensitivity characteristics of the phase difference pixels 71 (focus detecting pixels) change according to the image height. Therefore, the control device 5 holds and uses information on the light receiving sensitivity characteristics of the phase difference pixels 71 (focus detecting pixels) for different image heights.

Furthermore, the areas of the shaded areas in FIG. 16 correspond to the amounts of light received by the L pixel 100L and R pixel 100R. If there is a difference between the amounts of light received by the L pixel 100L and R pixel 100R for the same subject, an L image based on the L pixel 100L and an R image based on the R pixel 100R will differ from each other and detection of the interval between two images will be difficult. Therefore, performing illuminance correction (shading correction) for the L and R image signals according to the areas of the shaded areas in FIG. 16 facilitates detection of the interval between two images. An area SL of the shaded area in FIG. 16 and an area SR of the shaded area in FIG. 16 can be expressed by Equations (8) and (9) below and an illuminance correction coefficient can be expressed by, for example, Equation (10) below. The illuminance correction is performed by multiplication of output of the L pixel by this illuminance correction coefficient. In actuality, as represented by the shaded area in FIG. 15A, the light beam is two-dimensional with θx and θy and the area SL is thus expressed by Equation (11) below (the same applies to the area SR and description thereof will thus be omitted).

$$SL = \int_{\theta L}^{\theta U} f_L(\theta x) \cdot d\theta x \quad (8)$$

$$SR = \int_{\theta L}^{\theta U} f_R(\theta x) \cdot d\theta x \quad (9)$$

$$\text{Illuminance correction coefficient} = SR/SL \quad (10)$$

$$SL = \int\int f_L(\theta x, \theta y) \cdot d\theta x \cdot d\theta y \quad (11)$$

Process by Endoscope System

A process executed by the endoscope system 1 will be described next.

Figure 17:
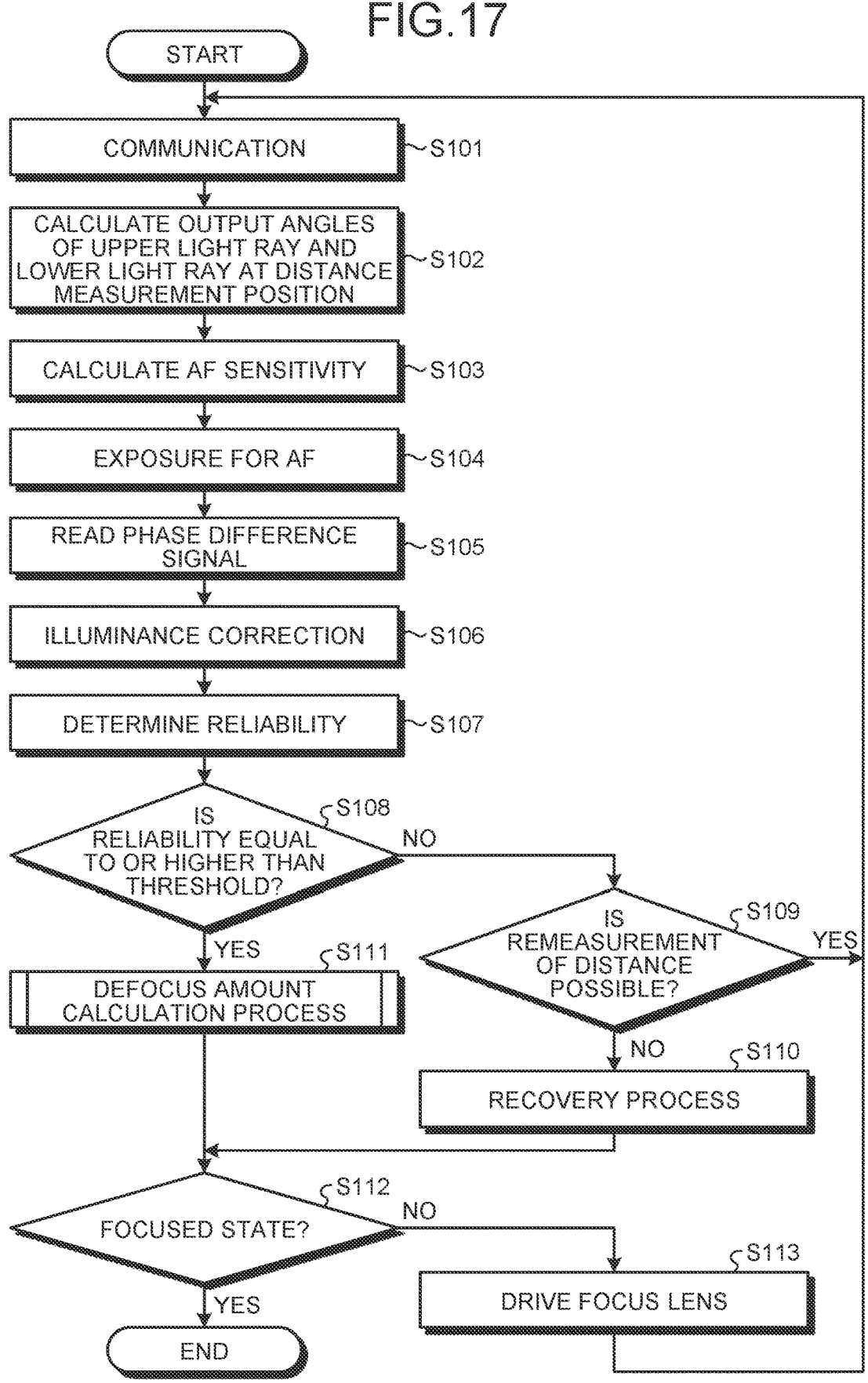
FIG. 17 is a flowchart illustrating an outline of a process executed by the endoscope system according to the first embodiment.

FIG. 17 is a flowchart illustrating an outline of the process executed by the endoscope system 1. An example of an AF process executed by the endoscope system 1 will be described by reference to FIG. 17.

As illustrated in FIG. 17, firstly, the control unit 54 performs communication with the endoscope 2 (Step S101). In this communication, the control unit 54 obtains lens information from the endoscope recording unit 64 of the endoscope 2 and obtains the lens information described above (corrected F-number (CF number) and corrected exit pupil position (CEXPI)) from the memory. The communication with the endoscope 2 may be implemented between the control unit 54 and the imaging control unit 65, periodically or as needed, instead of being implemented through this step.

Subsequently, the control unit 54 calculates angles at which an upper light ray and a lower light ray of a light beam are output at a distance measurement position (Step S102). By using a subject distance, an aperture, and data from the recording unit 53 (memory), the control unit 54 finds a CF number and CEXPI, and calculates, from these values, an output angle θU of the upper light ray of the light beam to the position measurement position and an output angle θL of the lower light ray of the light beam to the position measurement position.

Thereafter, the control unit 54 calculates AF sensitivity (Step S103). Specifically, by using the output angle θU of the upper light ray of the light beam to the distance measurement position, the output angle θL of the lower light ray of the light beam to the distance measurement position, and light receiving sensitivity characteristics of the phase difference pixels 71 (focus detecting pixels), the control unit 54 finds AF sensitivity through calculation of the above described interval between barycentric angles. The control unit 54 may find the AF sensitivity by referring to a table including precalculated AF sensitivity for each incident light ray angle.

Subsequently, by controlling the imaging control unit 65, the control unit 54 causes the imaging element 244 to execute exposure for AF (Step S104), causes the reading unit 63 to read phase difference signals from the phase difference pixels 71 and output the phase difference signals to the control device 5 (Step S105), and performs illuminance correction (Step S106). The illuminance correction for the phase difference signals (focus detecting pixel values) read at Step 3105 is performed by use of the AF calculation parameter (illuminance correction coefficient) calculated at Step S103 described above.

Subsequently, the control unit 54 determines reliability of the phase difference signals input from the phase difference pixels 71 (Step 3107). Specifically, on the basis of evaluation values obtained from correlation calculation by use of the phase difference signals, the control unit 54 calculates reliability of the phase difference signals. The evaluation values obtained from correlation calculation by use of the phase difference signals include any one or more of: saturation information on the phase difference pixels 71 (for example, the number of phase difference pixels 71 having saturated pixel values); a contrast value of the phase difference pixels 71 (for example, a contrast value between a pixel value of a right-open phase difference pixel 71R and a pixel value of a left-open phase difference pixel 71L); monotonicity of the phase difference pixels 71 (for example, monotonic increase or decrease of the image values in the area direction causes erroneous distance measurement); and the minimum correlation value.

Thereafter, the control unit 54 determines whether or not the reliability is equal to or higher than a threshold (Step S108). For example, the control unit 54 determines whether or not the total number of phase difference pixels 71 having unsaturated pixel value is 80% or more of the total number of all of the phase difference pixels 71, for the reliability. In a case where the control unit 54 has determined that the reliability is equal to or higher than the threshold (Step S108: Yes), the endoscope system 1 proceeds to Step S111 described later. On the contrary, in a case where the control unit 54 determines that the reliability is not equal to or higher than the threshold (Step S108: No), the endoscope system 1 proceeds to Step S109 described later.

At Step S109, the control unit 54 determines, on the basis of the phase difference signals, whether or not remeasurement of distance is possible. In a case where the control unit 54 has determined that remeasurement of distance is possible (Step S109: Yes), the endoscope system 1 proceeds to Step S101 described above. On the contrary, in a case where the control unit 54 has determined that remeasurement of distance is not possible (Step S109: No), the endoscope system 1 proceeds to Step S110 described later.

At Step S110, the control unit 54 performs a recovery process. Specifically, by controlling the imaging control unit 65, the control unit 54 causes the imaging control unit 65 to execute a recovery process of causing the imaging element 244 to perform exposure for AF again and causing the driver 245 to perform scan driving in which the focus state of the optical system 243 is changed until the reliability becomes equal to higher than the threshold. In this case, when the reliability is in a predetermined range, by controlling the imaging control unit 65, the control unit 54 may cause the imaging control unit 65 to execute a recovery process of causing the imaging element 244 to perform only exposure for AF again and stopping the driver 245. After Step S110, the endoscope system 1 returns to Step S101 described above.

At Step S111, the endoscope system 1 executes a defocus amount calculation process for the optical system 243. Details of this defocus amount calculation process will be described later.

Subsequently, the control unit 54 determines whether or not the optical system 243 is in a focused state (a state of being in focus) (Step S112). In a case where the control unit 54 has determined that the optical system 243 is in the focused state (Step S112: Yes), the endoscope system 1 ends this process. On the contrary, in a case where the control unit 54 has determined that the optical system 243 is not in the focused state (Step S112: No), the endoscope system 1 proceeds to Step S113.

At Step 3113, by driving the driver 245, the control unit 54 causes, on the basis of a result of the defocus amount calculation process, the focus lens 243*a* of the optical system 243 to move along the optical axis O1 and change the focusing state of the optical system 243. For example, on the basis of the defocus direction and defocus amount by the defocus amount calculation process described later, the control unit 54 drives the driver 245 to thereby cause the focus lens 243*a* of the optical system 243 to move in the defocus direction along the optical axis O1 and change the focusing state of the optical system 243. After Step S109, the endoscope system 1 returns to Step S101 described above.

Outline of Defocus Amount Calculation Process

An outline of the defocus amount calculation process at Step S111 in FIG. 17 described above will be described next.

Figure 18:
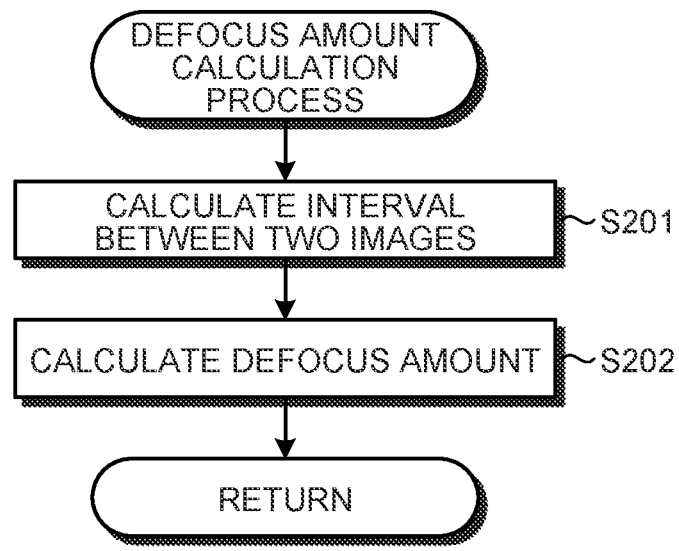
FIG. 18 is a flowchart illustrating an outline of a defocus amount calculation process.

FIG. 18 is a flowchart illustrating the outline of the defocus amount calculation process.

As illustrated in FIG. 18, firstly, the control unit 54 calculates, on the basis of the phase difference signals output from the plural pairs of left and right phase difference pixels 71, an interval between two images (Step S201). The interval between two images herein is a phase difference between two subject images, that is, an amount of displacement of image interval. Specifically, the interval between two images is a distance on the imaging surface of the imaging element 244, the distance being between: a right image corresponding to a right phase difference pixel signal output by a right-open phase difference pixel 71R through incidence of a right light beam on the right-open phase difference pixel 71R, the right light beam being of the light beam subjected to pupil division to the right and left via the optical system 243; and a left image corresponding to a left phase difference pixel signal output by a left-open phase difference pixel 71L through incidence of a left light beam on the left-open phase difference pixel 71L, the left light beam being of the light beam subjected to pupil division to the right and left via the optical system 243. Furthermore, the interval between two images is proportional to the distance (defocus amount) from the imaging surface of the imaging element 244 to the focus position (focus) of the optical system 243. This defocus amount is able to be calculated from the interval between two images and AF sensitivity (defocus amount=interval between two images×AF sensitivity).

Subsequently, the control unit 54 calculates a focus direction and a defocus amount of the optical system 243, on the basis of the interval between two images (Step S202). After Step 3202, the endoscope system 1 returns to the main routine in FIG. 17.

Outline of Interval Between Two Images

Details of the interval between two images will be described next.

Figure 19A:
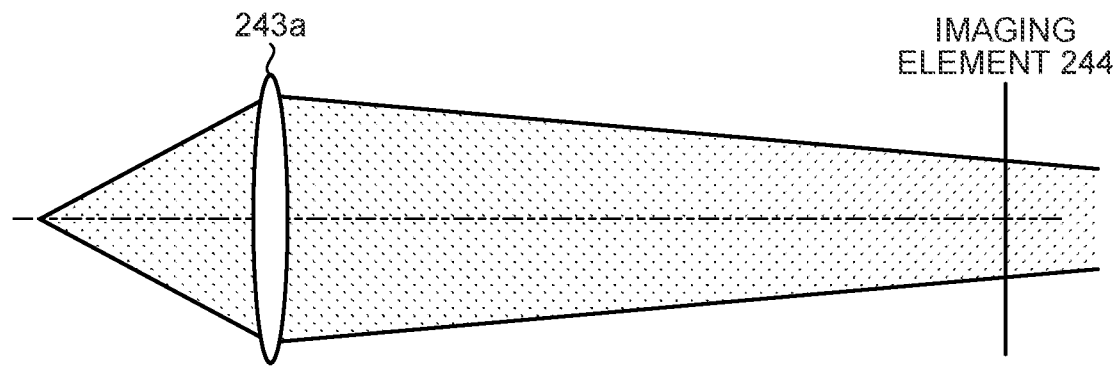
FIG. 19A is a schematic diagram illustrating a state where the front of a subject image formed at the imaging element by the optical system according to the first embodiment is out of focus.
Figure 19B:
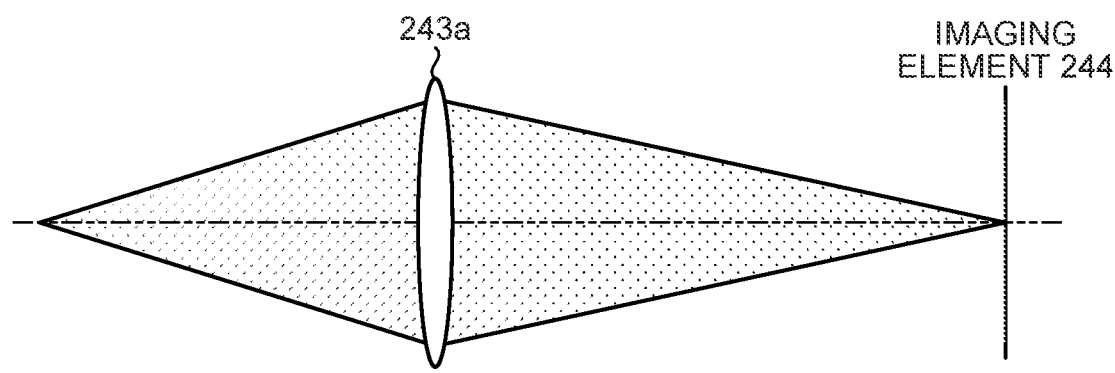
FIG. 19B is a schematic diagram illustrating a state where a subject image formed at the imaging element by the optical system according to the first embodiment is in focus.
Figure 19C:
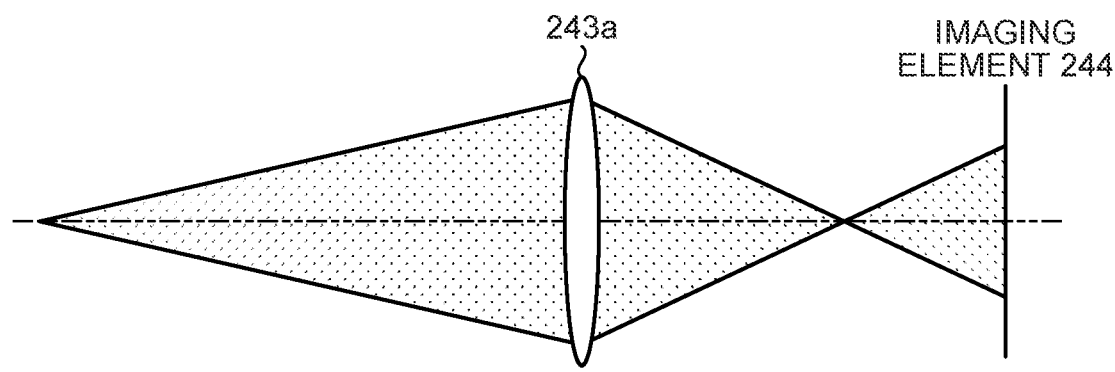
FIG. 19C is a schematic diagram illustrating a state where the back of a subject image formed at the imaging element by the optical system according to the first embodiment is out of focus.
Figure 20A:
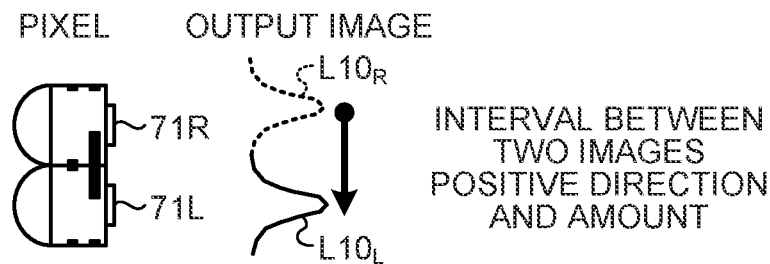
FIG. 20A is a diagram schematically illustrating a direction in which a subject image formed at the imaging element by the optical system according to the first embodiment has been displaced, and an interval between two images, in a state where the front of the subject image is out of focus.
Figure 20B:
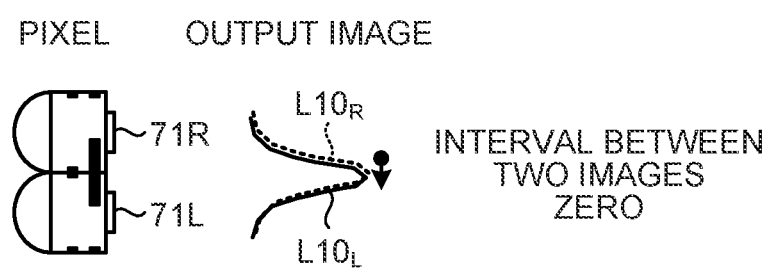
FIG. 20B is a diagram schematically illustrating a direction in which a subject image formed at the imaging element by the optical system according to the first embodiment has been displaced, and an interval between two images, in a state where the subject image is in focus.
Figure 20C:
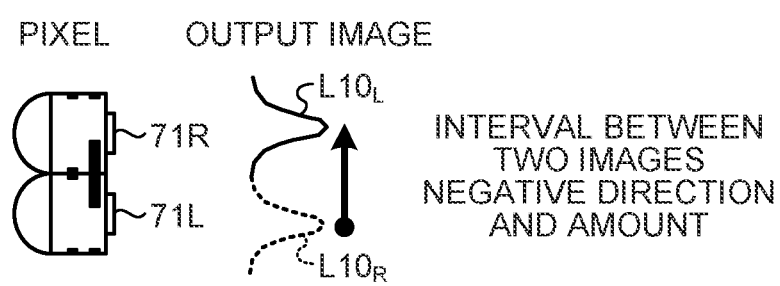
FIG. 20C is a diagram schematically illustrating a direction in which a subject image formed at the imaging element by the optical system according to the first embodiment has been displaced, and an interval between two images, in a state where the back of the subject image is out of focus.

FIG. 19A is a schematic diagram illustrating a state where the front of a subject image formed at the imaging element 244 by the optical system 243 is out of focus. FIG. 19B is a schematic diagram illustrating a state where a subject image formed at the imaging element 244 by the optical system 243 is in the focused state (state of being in focus). FIG. 19C is a schematic diagram illustrating a state where the back of a subject image formed at the imaging element 244 by the optical system 243 is out of focus. FIG. 20A is a diagram schematically illustrating the image displacement direction and interval between two images in the state where the front of the subject image formed at the imaging element 244 by the optical system 243 is out of focus. FIG. 20B is a diagram schematically illustrating the image displacement direction and interval between two images in the focused state (state of being in focus) of the subject image formed at the imaging element 244 by the optical system 243. FIG. 20C is a diagram schematically illustrating the image displacement direction and interval between two images in the state where the back of the subject image formed at the imaging element 244 by the optical system 243 is out of focus.

Furthermore, as illustrated in FIG. 19A and FIG. 20A, in the state where the front of the subject image formed at the imaging element 244 by the optical system 243 is out of focus, the interval between two images for the image phase difference signals output by the right-open phase difference pixel 71R and left-open phase difference pixel 71L has a "positive (+)" value.

Furthermore, as illustrated in FIG. 19B and FIG. 20B, in the focused state (state of being in focus) of the subject image formed at the imaging element 244 by the optical system 243, the image phase difference signals output by the right-open phase difference pixel 71R and left-open phase difference pixel 71L overlap each other and the interval between two images is "0".

Furthermore, as illustrated in FIG. 19C and FIG. 20C, in the state where the back of the subject image formed at the imaging element 244 by the optical system 243 is out of focus, the interval between two images for the image phase difference signals output by the right-open phase difference pixel 71R and left-open phase difference pixel 71L has a "negative (−)" value.

As described above, on the basis of the image interval of the pair of left and right phase difference signals output by the right-open phase difference pixel 71R and left-open phase difference pixel 71L, the control unit 54 calculates a focus movement direction (defocus direction) of the focus lens 243a of the optical system 243 and an interval between two images. Furthermore, because the focused position (focus position) of the optical system 243 has been set, the interval between two images is a quantity having a positive or negative sign. The interval between two images is able to be calculated by a publicly known phase difference AF method.

Method of Calculating Interval Between Two Images

A method of calculating an interval between two images will be described next.

Figure 22A:
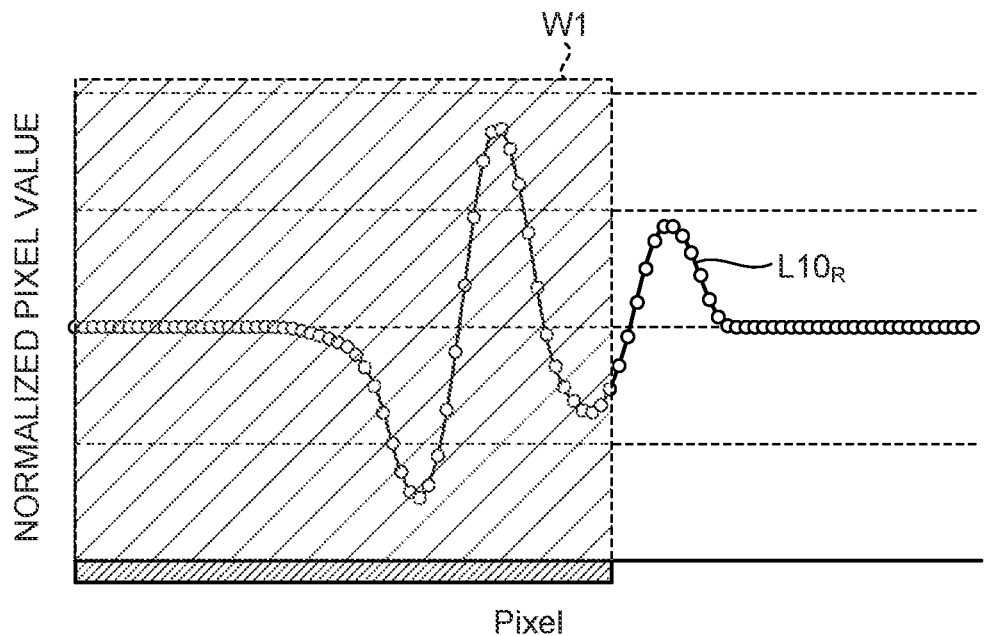
FIG. 22A is a diagram illustrating a state in which a predetermined window of the phase difference signal of the right-open phase difference pixels in FIG. 21 has been cut out.
Figure 22B:
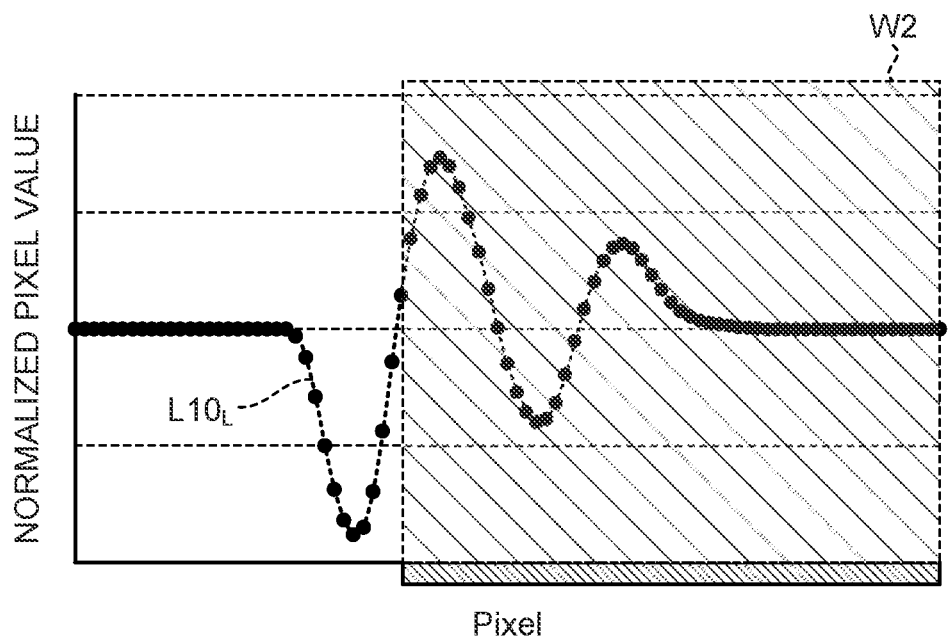
FIG. 22B is a diagram illustrating a state in which a predetermined window of the phase difference signal of the left-open phase difference pixels in FIG. 21 has been cut out.
Figure 23:
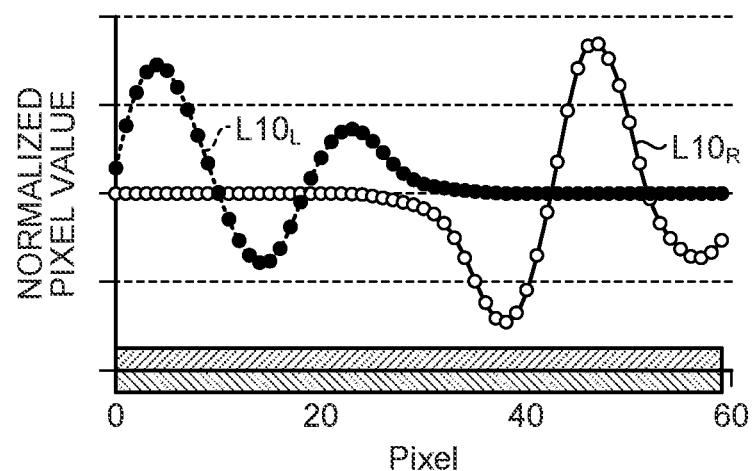
FIG. 23 is a diagram schematically illustrating correlation values between the phase difference signals of the right-open phase difference pixels and left-open phase difference pixels in FIG. 21.
Figure 24:
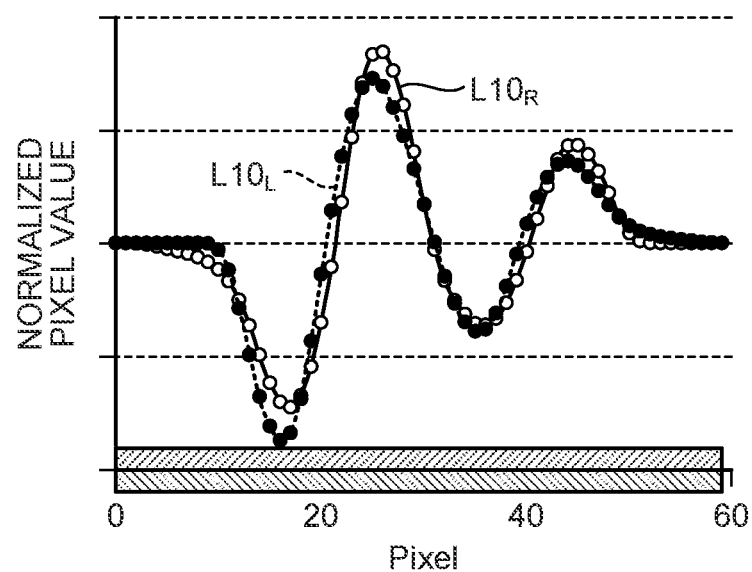
FIG. 24 is a diagram schematically illustrating correlation values between the phase difference signals of the right-open phase difference pixels and left-open phase difference pixels in FIG. 21.
Figure 25:
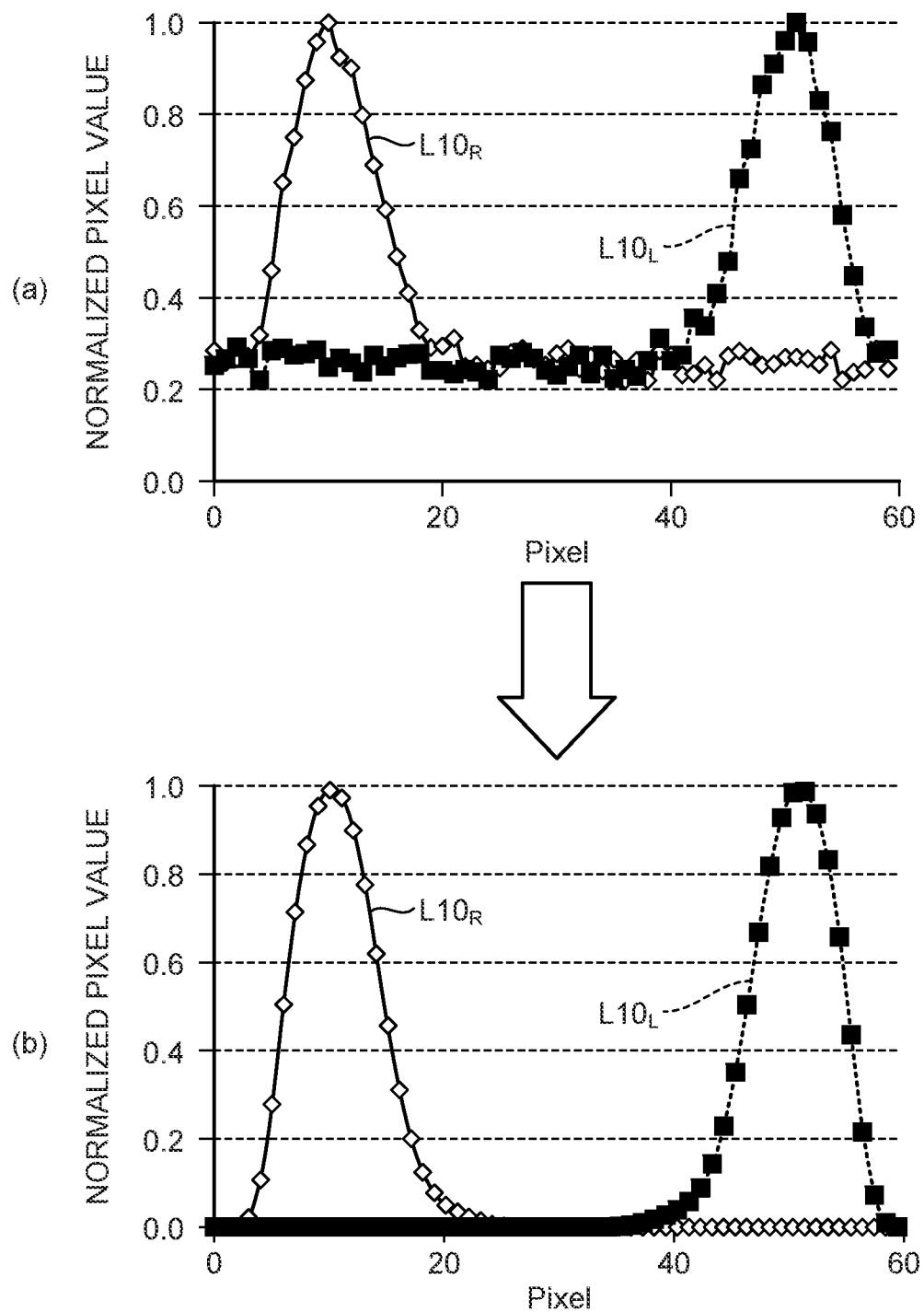
FIG. 25 is a diagram schematically illustrating the phase difference signals of the right-open phase difference pixels and left-open phase difference pixels, according to the first embodiment, the phase difference signals being those before filtering of the phase difference signals and those after the filtering.

FIG. 21 is a diagram schematically illustrating phase difference signals from right-open phase difference pixels 71R and left-open phase difference pixels 71L. FIG. 22A is a diagram illustrating a state where a predetermined window (range) of the phase difference signal from the right-open phase difference pixels 71R has been cut out. FIG. 22B is a diagram illustrating a state where a predetermined window (range) of the phase difference signal from the left-open phase difference pixels 71L has been cut out. FIG. 23 is a diagram schematically illustrating correlation values between the phase difference signals from the right-open phase difference pixels 71R and left-open phase difference pixels 71L in FIG. 21. FIG. 24 is a diagram schematically illustrating correlation values between the phase difference signals from the right-open phase difference pixels 71R and left-open phase difference pixels 71L in FIG. 21. FIG. 25 is a diagram schematically illustrating the phase difference signals from the right-open phase difference pixels 71R and left-open phase difference pixels 71L, the phase difference signals being those before filtering and those after the filtering. In FIG. 21 to FIG. 25, the horizontal axes represent pixel position (pixel address) and the vertical axes represent normalized pixel value. Furthermore, in FIG. 21 to FIG. 25, a curve L10 represents change in pixel value of the phase difference signal from the right-open phase difference pixels 71R and a curve L10$_L$ represents change in pixel value of the phase difference signal from the left-open phase difference pixels 71L.

As illustrated in FIG. 21, FIG. 22A, and FIG. 22B, by cutting out predetermined windows (ranges) of intervals between two images based on the phase difference signals output by the pairs of right-open phase difference pixels 71R and left-open phase difference pixels 71L, the control unit 54 calculates a correlation value for each pair of the right-open phase difference pixel 71R and the left-open phase difference pixel 71L. In this case, the control unit 54 calculates the absolute sum of differences in the window for the pairs of right-open phase difference pixels 71R and left-open phase difference pixels 71L (see, for example, FIG. 23) to retrieve a window amount with the smallest correlation. As illustrated in FIG. 24, the control unit 54 then calculates an interval between two images that is a window shift amount with the highest correlation (the smallest absolute value of difference). As illustrated in FIG. 25, to reduce the calculation error for the interval between two images, the control unit 54 subjects the phase difference signals to filtering according to the subject, the phase difference signals being output by the pairs of right-open phase difference pixels 71R and left-open phase difference pixels 71L.

As described above, the control unit 54 cuts out predetermined windows (ranges) of the phase difference signals output by the pairs of right-open phase difference pixels 71R and left-open phase difference pixels 71L, retrieves a window amount with the smallest correlation, and calculates an interval between two images that is a window shift amount with the highest correlation (the smallest absolute value of difference).

As described above, the control unit 54 calculates AF sensitivity, and on the basis of this AF sensitivity and the interval between two images, the control unit 54 calculates a defocus amount. The method of calculating the AF sensitivity is described in Japanese Unexamined Patent Application Publication No. 2017-227792 and detailed description thereof will thus be omitted.

That is, on the basis of a defocus amount and a defocus direction that are calculation results of the defocus amount calculation process, and a defocus amount based on AF sensitivity, the control unit 54 drives the driver 245 to thereby cause the focus lens 243a of the optical system 243 to move along the optical axis O1 and change the focusing state of the optical system 243. For example, on the basis of AF evaluation values (defocus direction and defocus amount (defocus amount=interval between two images×AF sensitivity)) by the above described defocus amount calculation process, the control unit 54 drives the driver 245 to thereby cause the focus lens 243a of the optical system 243 to move in the defocus direction along the optical axis O1 and change the focusing state of the optical system 243. The AF precision is thereby able to be improved even in a case where the optical system 243 that is an EDOF optical system and the phase difference pixels 71 for AF are used.

In the first embodiment described above, on the basis of phase difference signals input from the phase difference pixels 71, the control unit 54 calculates reliability of the phase difference signals output by the phase difference pixels 71 and calculates AF evaluation values on the basis of the phase difference signals output by the phase difference pixels 71. On the basis of the reliability and AF evaluation values, the control unit 54 then drives the driver 245 to cause the optical system 243 to be focused on an object (subject), and image quality degradation is thus able to be prevented and AF precision is able to be improved, even in a case where the optical system 243 that is a space division EDOF optical system and the phase difference pixels 71 for AF are used.

Furthermore, the first embodiment enables spectral characteristics of the first light beam and spectral characteristics of the second light beam to be approximately the same because the sum total of the number of times transmission of the first light beam occurs and the number of times reflection of the first light beam occurs is more than the sum total of the number of times transmission of the second light beam occurs and the number of times reflection of the second light beam occurs, the first light beam traveling through the first optical path in the optical system 243, the second light beam traveling through the second optical path in the optical system 243.

Furthermore, the first embodiment enables improvement of AF control because: the control unit 54 determines whether or not reliability of the phase difference signals output from the phase difference pixels 71 is equal to or higher than the predetermined threshold; in a case where the control unit 54 has determined that the reliability is equal to or higher than the predetermined threshold, the control unit 54 calculates AF evaluation values on the basis of the phase difference signals output from the phase difference pixels 71; and in a case where the control unit 54 has determined that the reliability is not equal to or higher than the predetermined threshold, the control unit 54 drives the driver 245 to cause the focus state of the optical system 243 to be changed until the reliability is determined to be equal to or higher than the predetermined threshold.

Furthermore, the first embodiment enables prevention of image quality degradation and improvement of AF precision because the control unit 54 calculates, on the basis of the phase difference signals output from the phase difference pixels 71, an interval between two images representing a phase difference between two subject images in the pupil division direction of at least one of the first light beam and second light beam, and calculates, on the basis of this interval between two images, AF evaluation values that are a defocus amount and a defocus direction corresponding to the interval between two images.

Furthermore, the first embodiment enables prevention of image quality degradation and improvement of AF precision even in a case where the optical system 243 that is a space division EDOF optical system and the phase difference pixels 71 for AF are used, because the first imaging portion 601 has the plural phase difference pixels 71 arranged therein.

Figure 26:
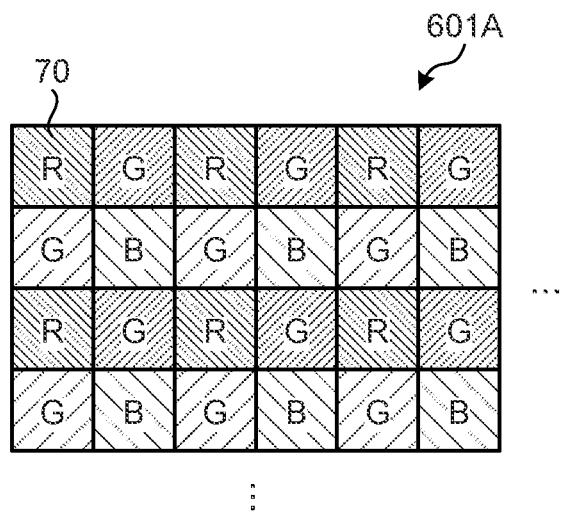
FIG. 26 is a diagram schematically illustrating a first imaging portion according to a modified example of the first embodiment.
Figure 27:
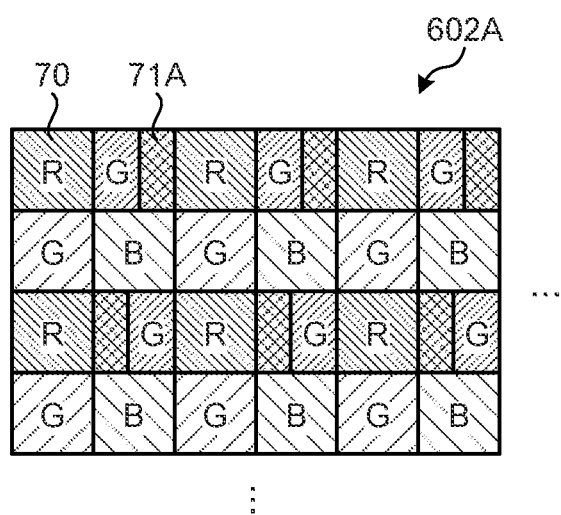
FIG. 27 is a diagram schematically illustrating a second imaging portion according to the modified example of the first embodiment.

In the above described first embodiment, the phase difference pixels 71 are provided in the first imaging portion 601 (near the near point image circle) but phase difference pixels 71 may be provided in the second imaging portion 602 (near the far point image circle). Specifically, as illustrated in FIG. 26 and FIG. 27, only imaging pixels may be provided in a first imaging portion 601A (near a near point image circle) (see FIG. 26) and phase difference pixels 71A may be provided in a second imaging portion 602A (near a far point image circle) (see FIG. 27).

Second Embodiment

A second embodiment will be described next. An endoscope system according to the second embodiment has a configuration different from that of the above described endoscope system 1 according to the first embodiment and executes a process different from that by the endoscope system 1. Specifically, a first focus detecting unit and a second focus detecting unit each configured by use of plural phase difference pixels are respectively provided in a first imaging portion (at a near point image circle) and a second imaging portion (at a far point image circle) in an imaging element. After description of the configuration of the endoscope system according to the second embodiment, the process executed by the endoscope system according to the second embodiment will be described, hereinafter. The same reference signs will be assigned to components that are the same as those of the above described endoscope system 1 according to the first embodiment, and detailed description thereof will be omitted.

Functional Configuration of Endoscope System

Figure 28:
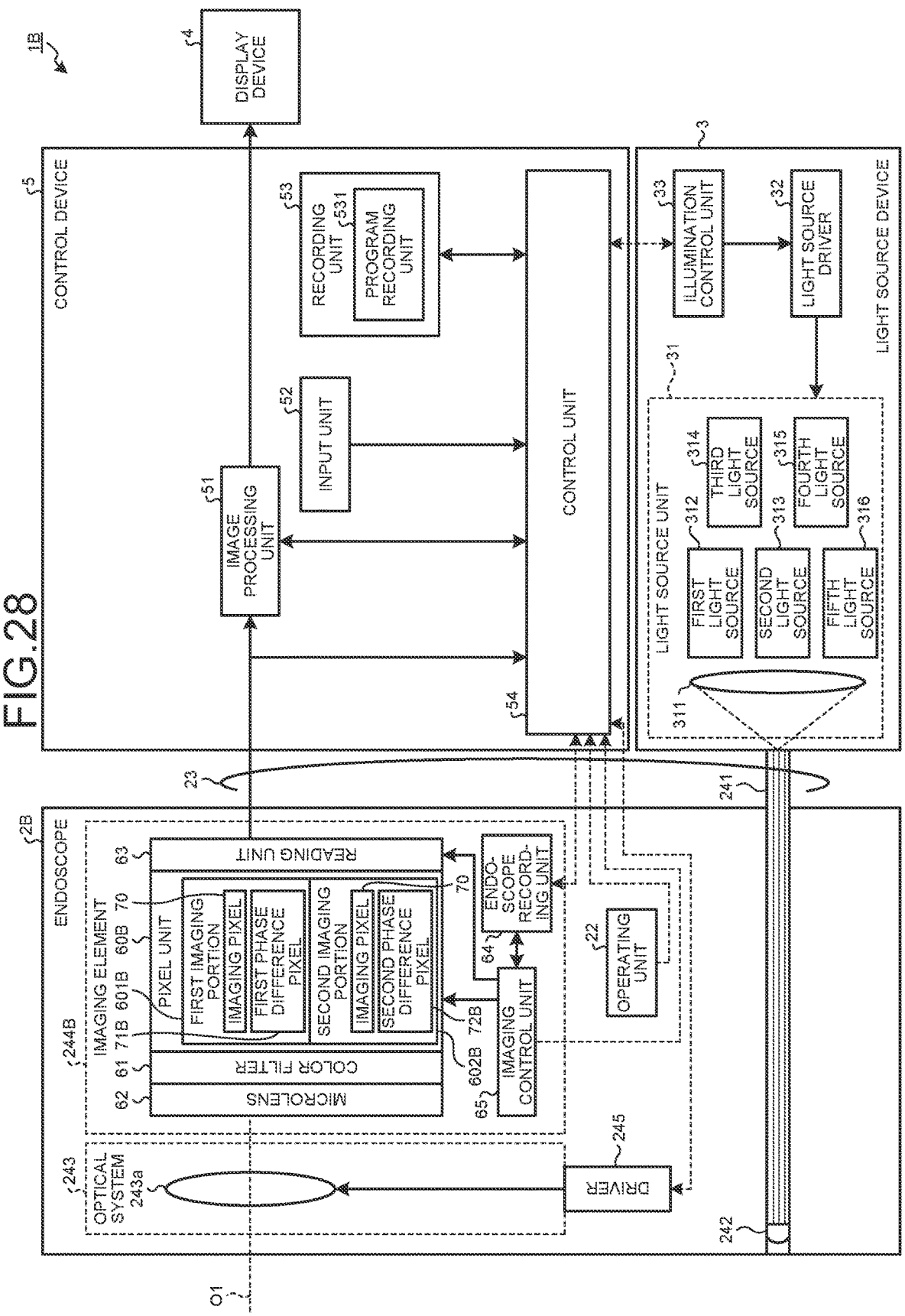
FIG. 28 is a block diagram illustrating a functional configuration of an endoscope system according to a second embodiment.

FIG. 28 is a block diagram illustrating a functional configuration of the endoscope system according to the second embodiment.

An endoscope system 1B illustrated in FIG. 28 includes an imaging element 244B instead of the imaging element 244 according to the first embodiment described above.

The imaging element 244B includes a pixel unit 60B instead of the pixel unit 60 according to the first embodiment described above. The pixel unit 60B has a first imaging portion 601B and a second imaging portion 602B.

Figure 29:
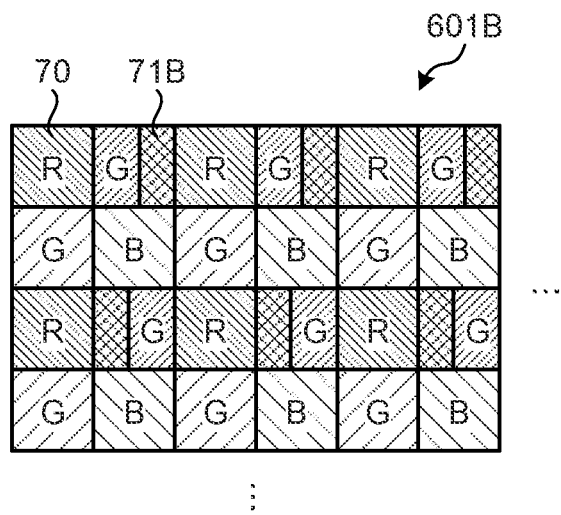
FIG. 29 is a diagram schematically illustrating a first imaging portion according to the second embodiment.
Figure 30:
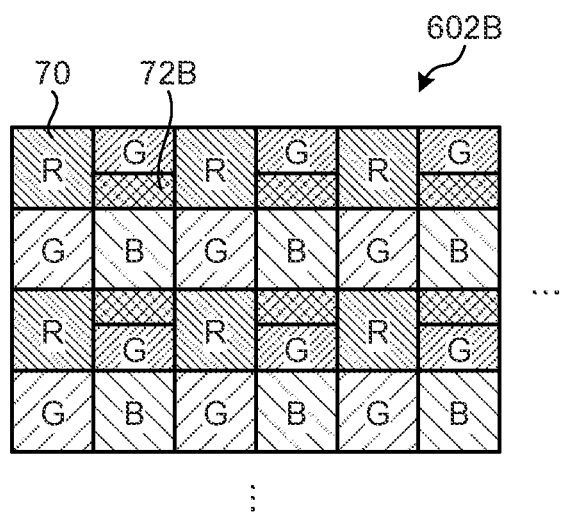
FIG. 30 is a diagram schematically illustrating a second imaging portion according to the second embodiment.

FIG. 29 is a diagram schematically illustrating the first imaging portion 601B. FIG. 30 is a diagram schematically illustrating the second imaging portion 602B. In FIG. 29 and FIG. 30, the first imaging portion 601B and the second imaging portion 602B are integral with each other but without being limited to this example, they may be separately bodied. Furthermore, the first imaging portion 601B and the second imaging portion 602B have the same number of pixels and the same pixel size, but without being limited to this example, they may have different numbers of pixels and/or pixel sizes.

The first imaging portion 601B will be described first.

The first imaging portion 601B includes plural pixels each having a photoelectric converter, the plural pixels being arranged in a two-dimensional matrix, and captures an image of a first light beam that travels through the first optical path in the optical system 243. The first imaging portion 601B has imaging pixels 70 and first phase difference pixels 71B.

As illustrated in FIG. 29, the first phase difference pixels 71B output a first phase difference signal (image signal) for focus detection. Furthermore, as illustrated in FIG. 29, the first phase difference pixels 71B are arranged at predetermined intervals in place of imaging pixels 70. Specifically, the first phase difference pixels 71B are each arranged at the place for a green filter in a unit of a Bayer arrangement. The arrangement of the first phase difference pixels 71B is not limited to this example, and the first phase difference pixels 71B may each be arranged in place of an imaging pixel 70 at any place. Furthermore, the first phase difference pixels 71B are each not necessarily arranged at the place of a green filter in a unit of a Bayer arrangement, and may, for example, be arranged at the place of a red filter or a blue filter. Furthermore, the plural first phase difference pixels 71B are each one of a right-open pixel and a left-open pixel, generate a pair of left and right phase difference signals for focus detection, and output this pair of left and right phase difference signals.

The second imaging portion 602B will be described next.

As illustrated in FIG. 30, the second imaging portion 602B includes plural pixels each having a photoelectric converter, the plural pixels being arranged in a two-dimensional matrix, and captures an image of a second light beam that travels through the second optical path in the optical system 243. The second imaging portion 602B has imaging pixels 70 and second phase difference pixels 72B.

The second phase difference pixels 72B output a second phase difference signal (image signal) for focus detection. Furthermore, as illustrated in FIG. 30, the second phase difference pixels 72B are arranged at predetermined intervals in place of imaging pixels 70. Specifically, the second phase difference pixels 72B are each arranged at the place for a green filter in a unit of a Bayer arrangement. The arrangement of the second phase difference pixels 72B is not limited to this example, and the second phase difference pixels 72B may each be arranged in place of an imaging pixel 70 at any place. Furthermore, the second phase difference pixels 72B are each not necessarily arranged at the place of a green filter in a unit of a Bayer arrangement, and may, for example, be arranged at the place of a red filter or a blue filter. Furthermore, the plural second phase difference pixels 72B are each one of a top-open pixel and a bottom-open pixel, generate a pair of upper and lower phase difference signals for focus detection, and output this pair of upper and lower phase difference signals.

As described above, the first phase difference pixels 71B and the second phase difference pixels 72B are arranged so that the first phase difference pixels 71B and the second phase difference pixels 72B will be orthogonal to each other in a case where the first imaging portion 601B and the second imaging portion 602B are superimposed on each other with reference to a predetermined pixel. Furthermore, the first phase difference pixels 71B of the first imaging portion 601B and the second phase difference pixels 72B of the second imaging portion 602B are respectively arranged orthogonally to each other so that a pupil division direction of the first light beam and a pupil division direction of the second light beam differ from each other.

Outline of AF Process by Optical System

An outline of an AF process by the optical system 243 in the endoscope system 1B will be described next.

Figure 31:
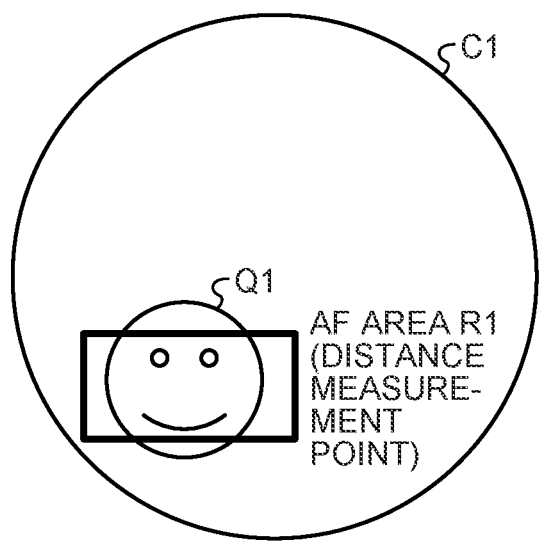
FIG. 31 is a diagram schematically illustrating a focusing state of a subject image at the first imaging portion according to the second embodiment.
Figure 32:
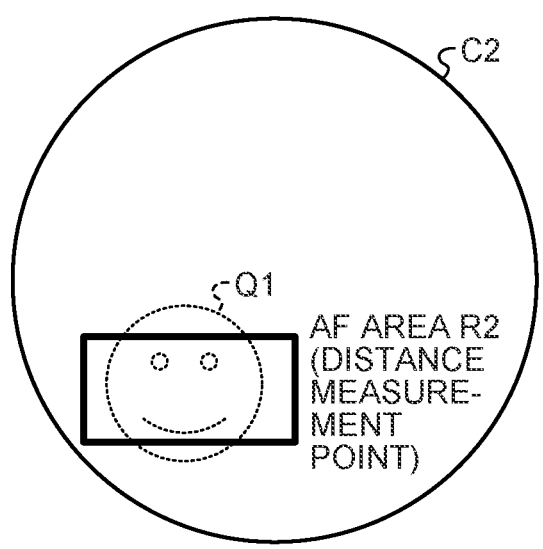
FIG. 32 is a diagram schematically illustrating a focusing state of the subject image at the second imaging portion according to the second embodiment.
Figure 33:
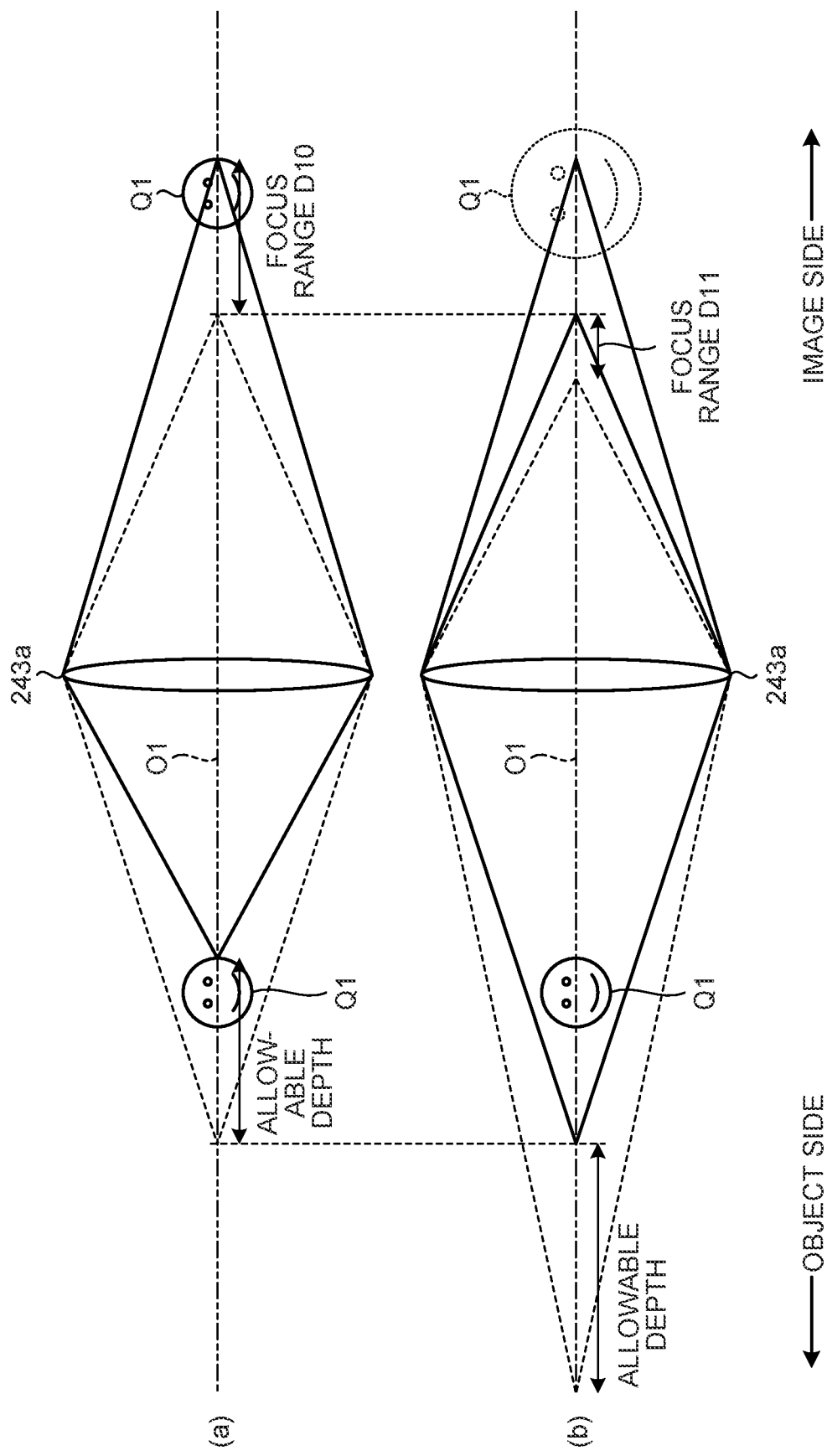
FIG. 33 is a diagram schematically illustrating an outline of an AF process by an optical system in the endoscope system according to the second embodiment.

FIG. 31 is a diagram schematically illustrating a focusing state of a subject image at the first imaging portion 601B. FIG. 32 is a diagram schematically illustrating a focusing state of a subject image at the second imaging portion 602B. FIG. 33 is a diagram schematically illustrating the outline of the AF process by the optical system 243 in the endoscope system 1B. In FIG. 33, (a) illustrates a focusing state of the first imaging portion 601B (near point image circle) and (b) illustrates a focusing state of the second imaging portion 602B (far point image circle).

As illustrated in FIG. 31 to FIG. 33, in the AF process, in a case where an object point position on which a subject image is desired to be focused is different from an image circle of an object point detected, due to the pupil division directions for the phase difference pixels 71, even if an image is more defocused than the other image, if there are many detectable edges, reliability of the phase difference signals becomes high. In this case, the AF process enables, on the basis of a defocus amount and a defocus direction that are AF evaluation values for one of the object point image circles, focusing on the other object point image circle.

For example, as illustrated in FIG. 31 to FIG. 33, in the case described with respect to the AF process, reliability of phase difference signals in an AF area R1 in the near point image circle at the first imaging portion 601B is low (there are no detectable edges) and reliability of phase difference signals in an AF area R2 of the far point image circle at the second imaging portion 602B is high. In this case, in the AF process, on the basis of a defocus amount detected for the far point image circle of the second imaging portion 602B and an optical path length difference that is a difference between the first optical path and the second optical path, focusing on the near point is enabled. As described above, in a case where focusing on the near point image circle at the first imaging portion 601B is achieved, a defocused image is obtained in the far point image circle at the second imaging portion 602B.

Process by Endoscope System

Figure 34:
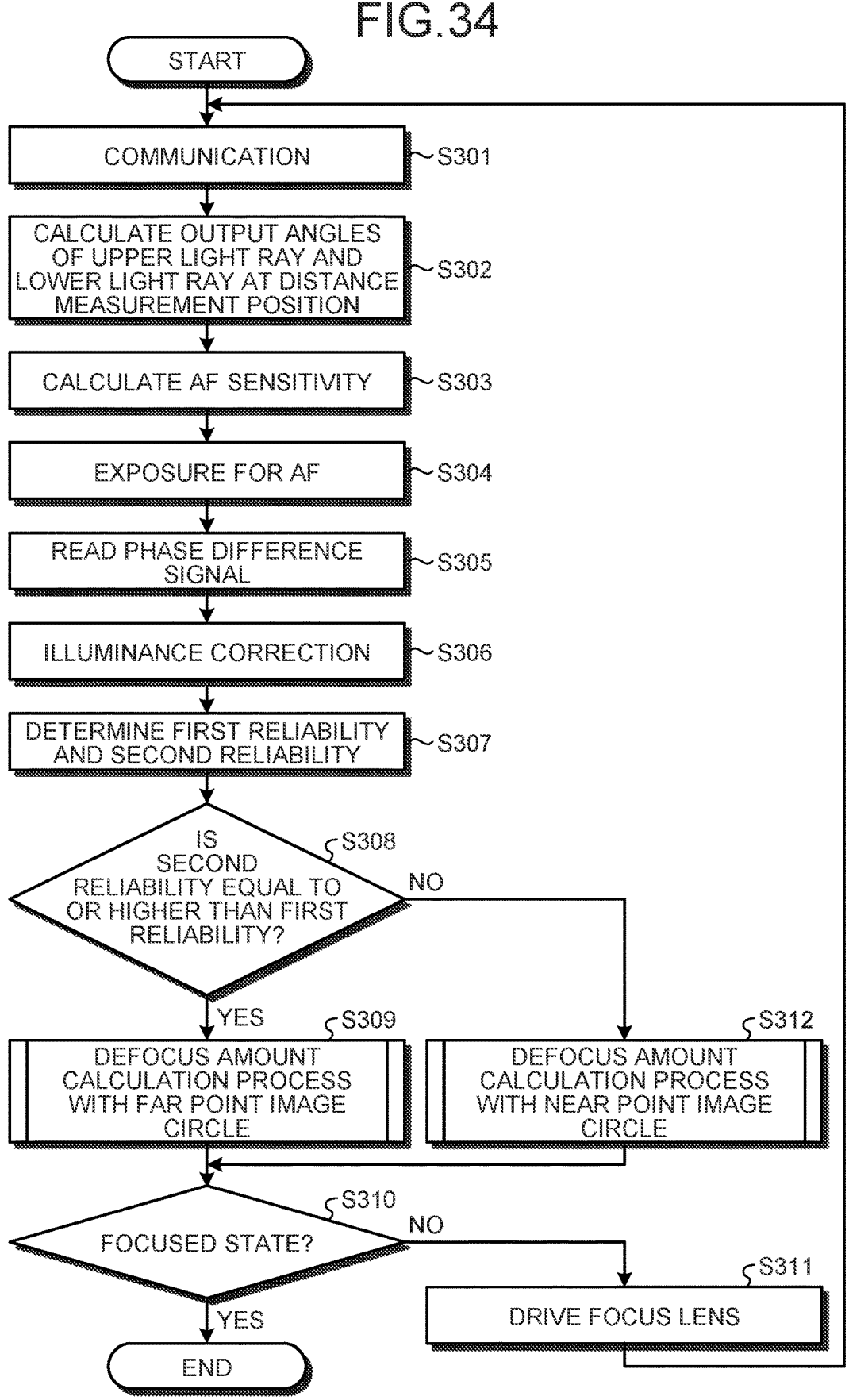
FIG. 34 is a flowchart illustrating an outline of a process executed by the endoscope system according to the second embodiment.

A process executed by the endoscope system 1B will be described next. FIG. 34 is a flowchart illustrating an outline of the process executed by the endoscope system 1B.

In FIG. 34, Step S301 to Step S306 respectively correspond to Step 3101 to Step S106 in FIG. 17 described above.

At Step S307, the control unit 54 determines first reliability of a first phase difference signal input from the first phase difference pixels 71B and second reliability of a second phase difference signal input from the second phase difference pixels 72B. Specifically, similarly to Step S107 in FIG. 17 described above, the control unit 54 determines first reliability of a first phase difference signal input from the first phase difference pixel 71B and second reliability of a second phase difference signal input from the second phase difference pixels 72B.

Subsequently, the control unit 54 determines whether or not the second reliability is equal to or higher than the first reliability (Step S308). In a case where the control unit 54 has determined that the second reliability is equal to or higher than the first reliability (Step S308: Yes), the endoscope system 1B proceeds to Step S309 described later. On the contrary, in a case where the control unit 54 has determined that the second reliability is not equal to or higher than the first reliability (Step S308: No), the endoscope system 1B proceeds to Step S312 described later.

At Step S309, on the basis of the second phase difference signal output by the second imaging portion 602B, the control unit 54 executes a far point image circle defocus amount calculation process of calculating a defocus amount. Details of this far point image circle defocus amount calculation process will be described later. After Step S309, the endoscope system 1B proceeds to Step S310 described later.

Step S310 and Step S311 respectively correspond to Step S112 and Step S113 in FIG. 17 described above.

At Step S312, on the basis of the first phase difference signal output by the first imaging portion 601B, the control unit 54 executes a near point image circle defocus amount calculation process of calculating a defocus amount. Details of this near point image circle defocus amount calculation process will be described later. After Step S312, the endoscope system 1B proceeds to Step S310.

Far Point Image Circle Defocus Amount Calculation Process

Figure 35:
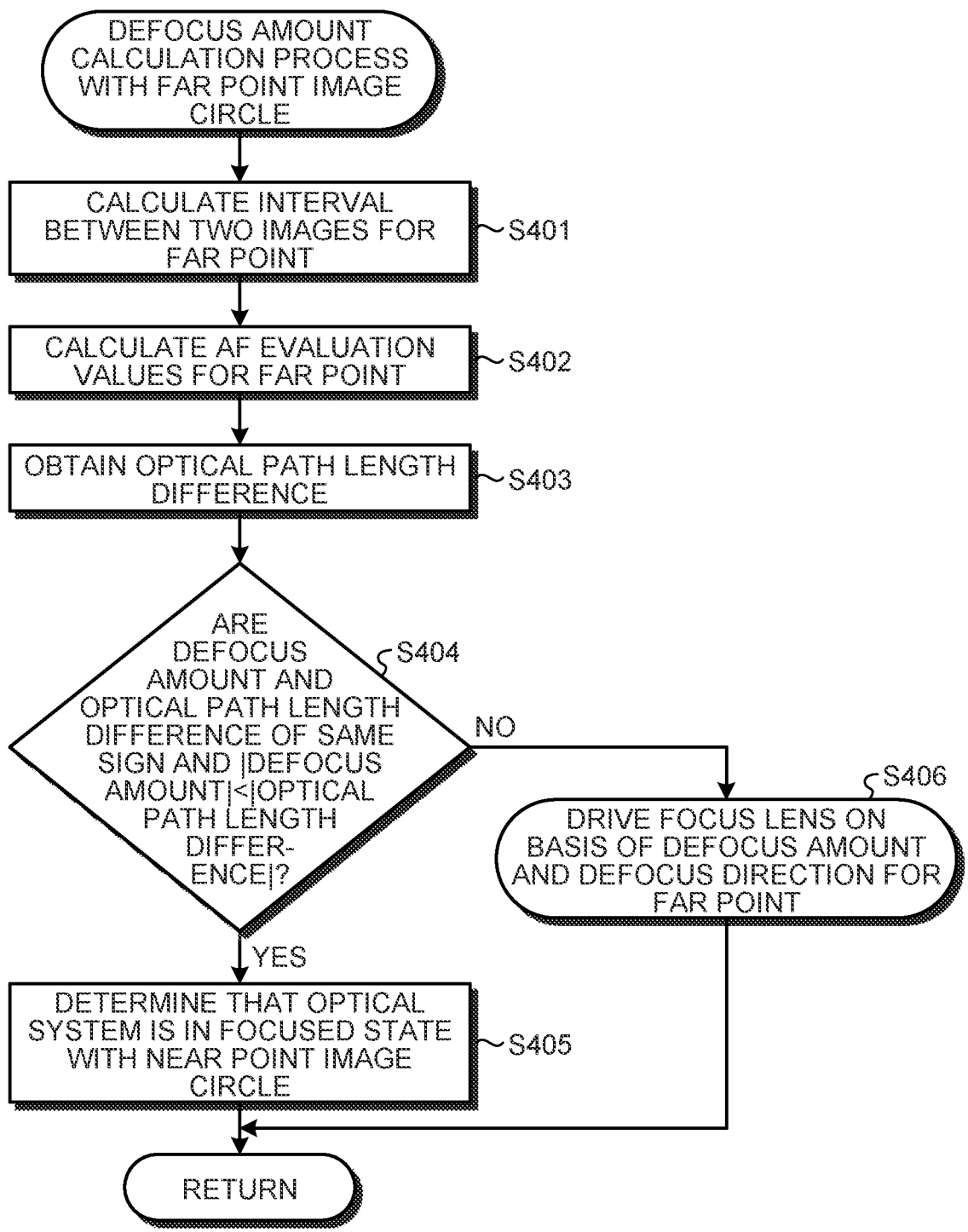
FIG. 35 is a flowchart illustrating an outline of a far point image circle defocus amount calculation process.

The far point image circle defocus amount calculation process at Step S309 in FIG. 34 described above will be described next. FIG. 35 is a flowchart illustrating an outline of the far point image circle defocus amount calculation process.

As illustrated in FIG. 35, firstly, on the basis of the second phase difference signal output from the second imaging portion 602B (far point image circle), the control unit 54 calculates an interval between two images at the far point (a second interval between two images) (Step S401).

Subsequently, on the basis of the interval between two images at the far point, the control unit 54 calculates AF evaluation values for the far point (a second defocus direction and a second defocus amount) (Step 3402) and obtains an optical path length difference (Step S403). This optical path length difference is a difference between lengths of the first optical path and the second optical path.

Subsequently, the control unit 54 determines whether or not the defocus amount (second defocus amount) of the AF evaluation values and the optical path length difference are of the same sign and the defocus amount (second defocus amount) has an absolute value less than the optical path length difference ("defocus amount (second defocus amount)" <"optical path length difference") (Step S404). In a case where the control unit 54 has determined that the defocus amount (second defocus amount) and the optical path length difference are of the same sign and the absolute value of the defocus amount (second defocus amount) is less than the optical path length difference (Step S404: Yes), the control unit 54 determines that the optical system 243 is focused on the near point image circle at the first imaging portion 601A (Step S405).

Figure 36:
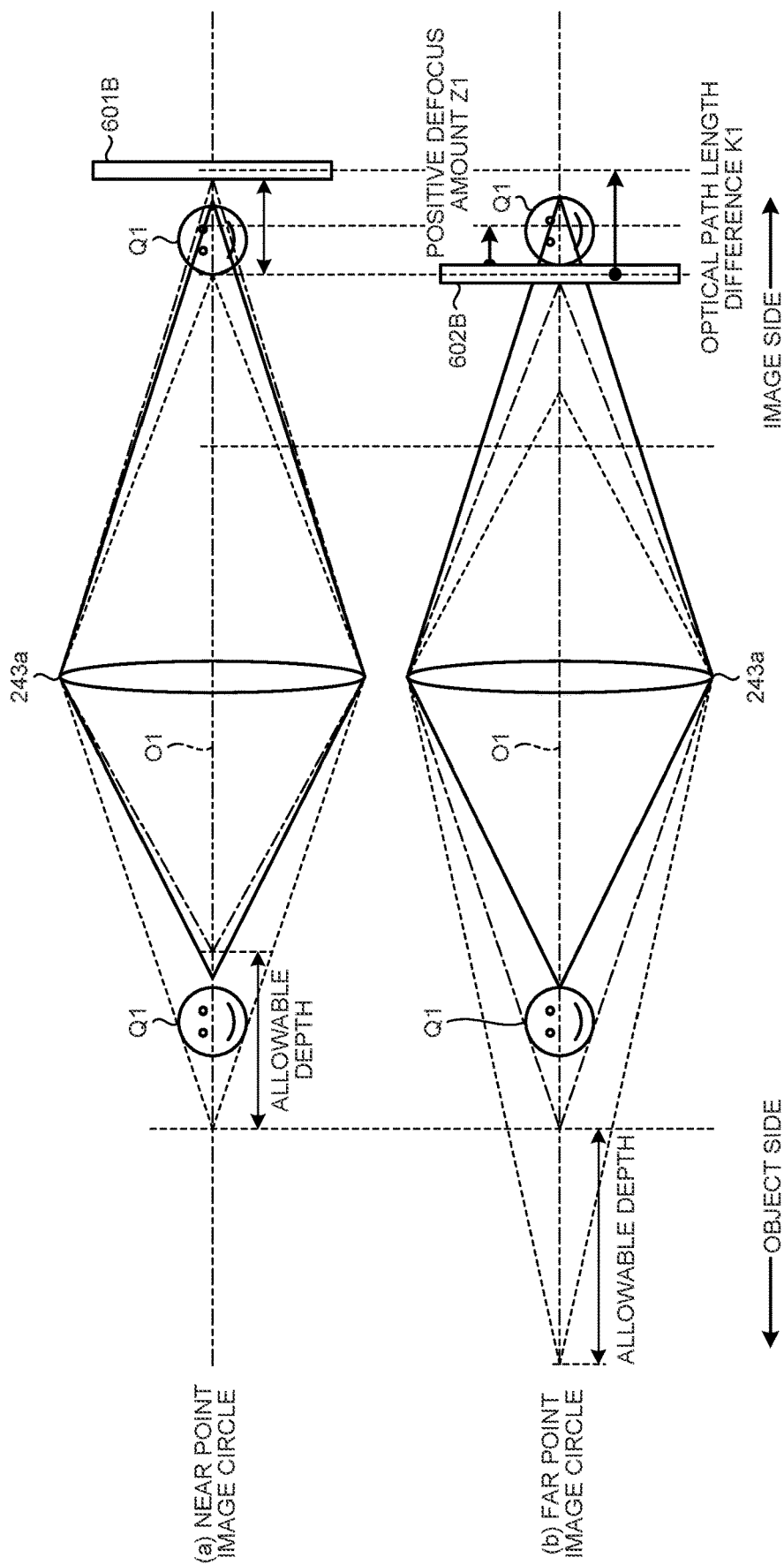
FIG. 36 is a diagram schematically illustrating a focusing state of the optical system in a case where a defocus amount of AF evaluation values and an optical path length difference are of the same sign and the defocus amount has an absolute value less than the optical path length difference.

FIG. 36 is a diagram schematically illustrating a focusing state of the optical system 243 in a case where the defocus amount (second defocus amount) of the AF evaluation values and the optical path length difference are of the same sign and the absolute value of the defocus amount (second defocus amount) is less than the optical path length difference.

As illustrated in FIG. 36, in a case where a defocus amount Z1 (second defocus amount) of the AF evaluation values and an optical path length difference K1 are of the same sign (a second defocus direction is in the positive direction to the image side) and the absolute value of the defocus amount Z1 (second defocus amount) is less than the optical path length difference K1 (Z1<K1), the control unit 54 determines that the optical system 243 is a state (in an allowable depth) of being focused on a subject Q1 in the near point image circle at the first imaging portion 601B. Therefore, without driving the driver 245, the control unit 54 performs control of maintaining the current position of the focus lens 243a on the optical axis O1. After Step S405, the endoscope system 1B returns to the main routine in FIG. 34.

At Step S404, in a case where the control unit 54 has determined that the defocus amount (second defocus amount) has the same sign as the optical path length difference and the absolute value of the defocus amount (second defocus amount) is not less than the optical path length difference (Step S404: No), the control unit 54 causes the focus lens 243a of the optical system 243 to move along the optical axis O1, on the basis of the defocus amount Z1 (second defocus amount) of the second imaging portion 602A, optical path length difference K1, and defocus direction (second defocus direction) (Step S406). After Step S406, the endoscope system 1B returns to the main routine in FIG. 34.

Figure 37:
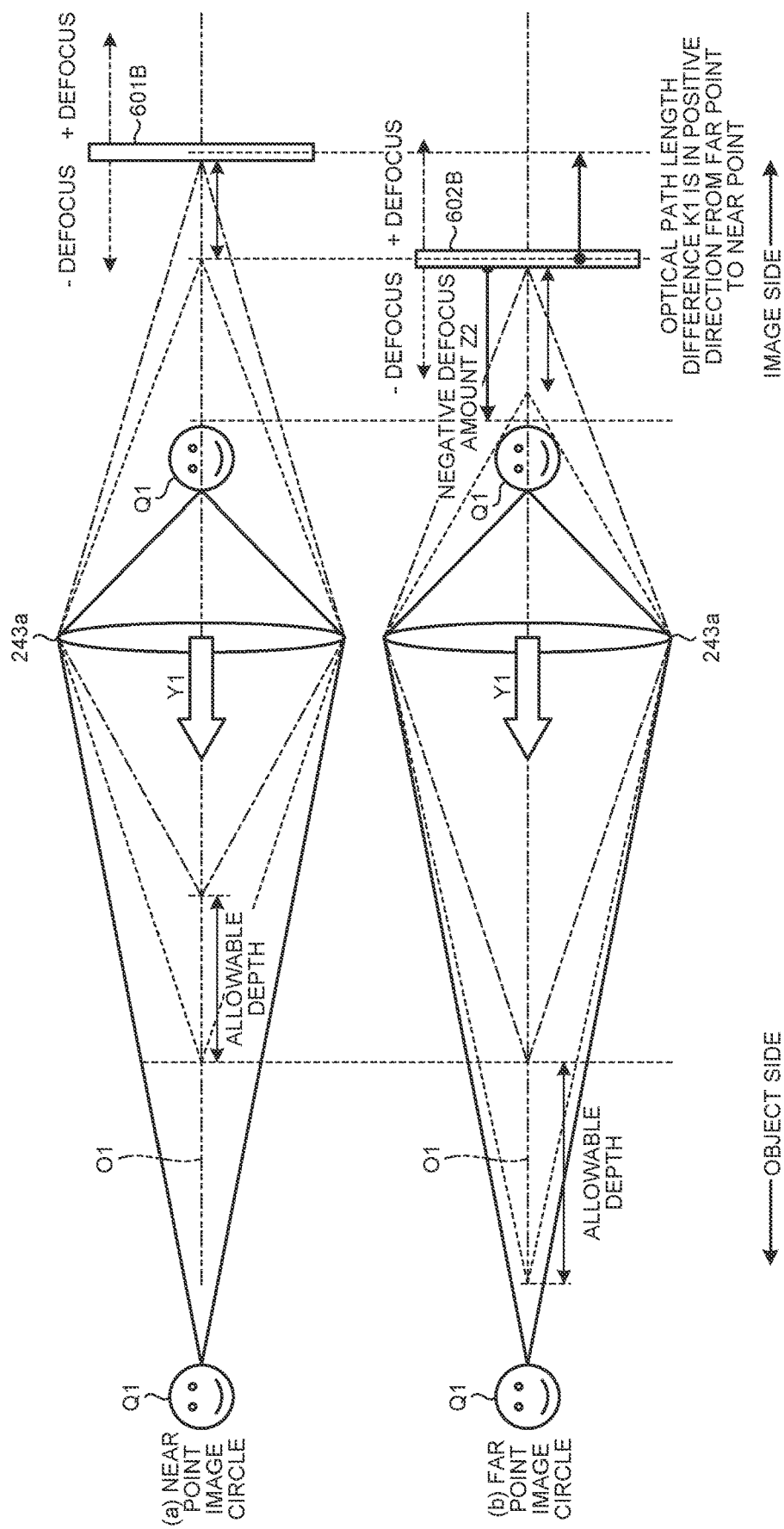
FIG. 37 is a diagram schematically illustrating a focusing state of the optical system in a case where a defocus amount of AF evaluation values and an optical path length difference are of different signs.

FIG. 37 is a diagram schematically illustrating a focusing state of the optical system 243 in a case where a defocus amount of AF evaluation values and an optical path length difference are of different signs.

As illustrated in FIG. 37, in a case where a defocus amount Z2 (a second defocus amount is in a negative direction to the image side) and the optical path length difference K1 (in a positive direction from the far point to the near point) are of different signs, the control unit 54 drives the driver 245, on the basis of the defocus amount (second defocus amount) and defocus direction of the second imaging portion 602A, to thereby cause the focus lens 243a of the optical system 243 to move along the optical axis O1 by the defocus amount Z2 (second defocus amount) toward the subject (an arrow Y1), so that the optical system 243 is focused on the subject Q1 at the far point (far point image circle).

Figure 38:
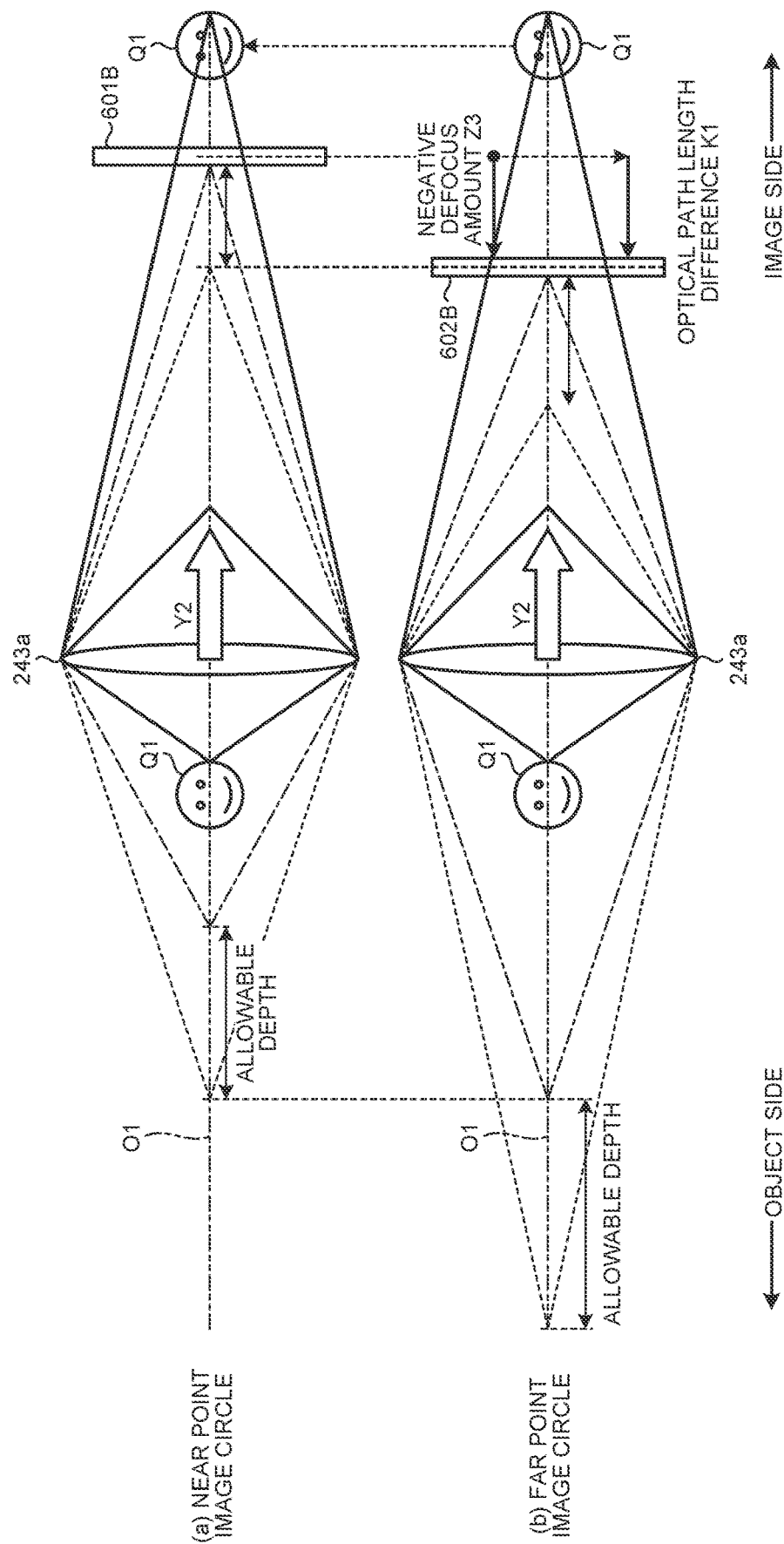
FIG. 38 is a diagram schematically illustrating a focusing state of the optical system in a case where a defocus amount and an optical path length difference are of the same sign and the defocus amount has an absolute value not less than the optical path length difference.

FIG. 38 is a diagram schematically illustrating a focusing state of the optical system 243 in a case where the defocus amount and the optical path length difference are of the same sign and the defocus amount has an absolute value not less than the optical path length difference.

As illustrated in FIG. 38, in a case where a defocus amount Z3 and an optical path length difference K1 are of the same sign (negative direction from the near point to the far point) and the defocus amount Z3 has an absolute value equal to or more than the optical path length difference K1 (Z3≥K1), the control unit 54 drives the driver 245 to thereby cause the focus lens 243a of the optical system 243 to move along the optical axis O1 to the image side (arrow Y2) by the absolute value of a difference between the defocus amount Z3 at the second imaging portion 602B and the optical path length difference K1.

As described above, in a case where the second reliability of the second phase difference signal output from the second phase difference pixels 72B at the second imaging portion 602B is equal to higher than the first reliability, the control unit 54 performs the AF process for the subject Q1 by controlling, on the basis of the defocus direction (second defocus direction) and defocus amount (second defocus amount) of the AF evaluation values and the optical path length difference, the position of the focus lens 243a of the optical system 243.

Near Point Image Circle Defocus Amount Calculation Process

Figure 39:
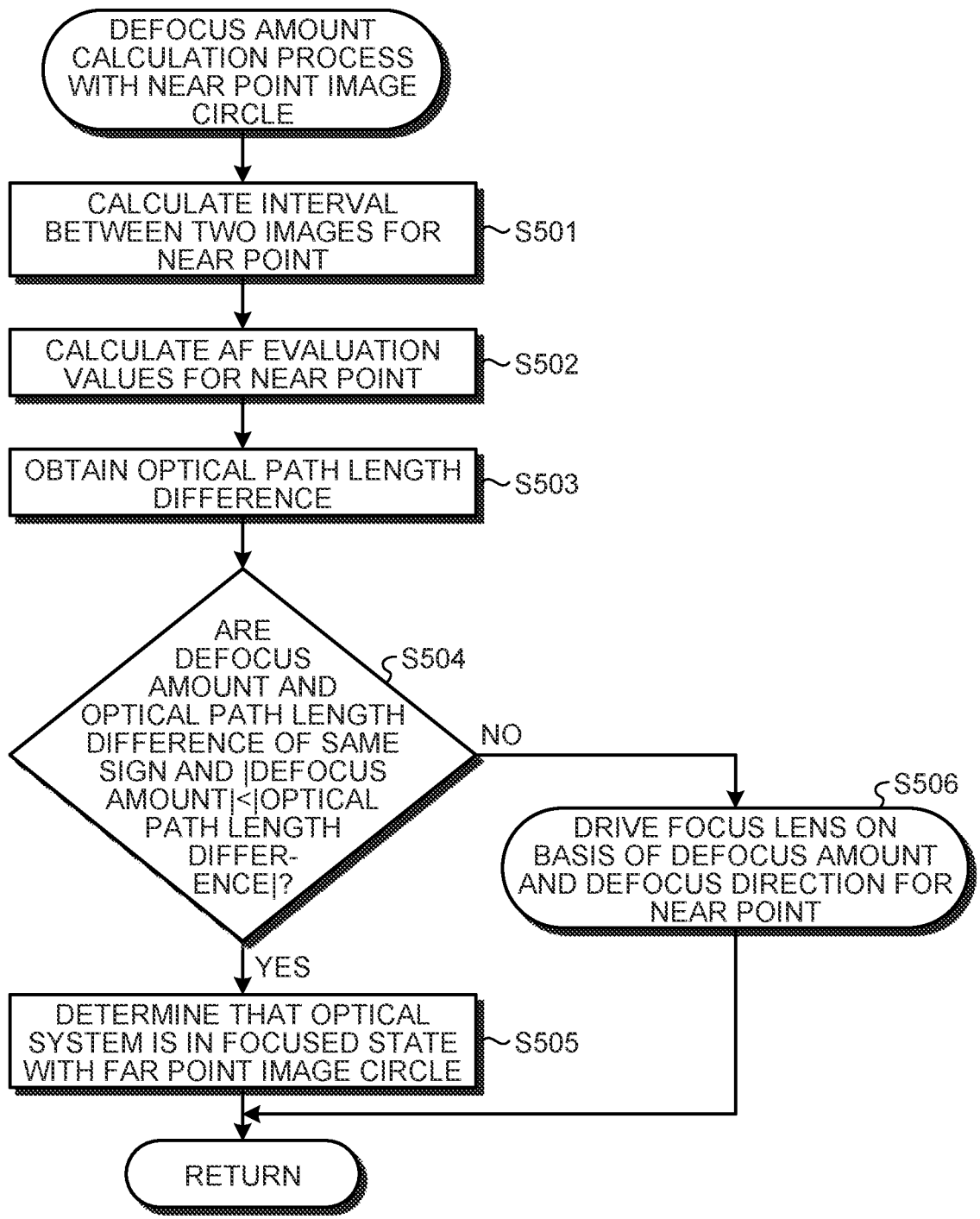
FIG. 39 is a flowchart illustrating an outline of a near point image circle defocus amount calculation process.

The near point image circle defocus amount calculation process at Step S312 in FIG. 34 described above will be described next. FIG. 39 is a flowchart illustrating an outline of the near point image circle defocus amount calculation process.

As illustrated in FIG. 39, firstly, on the basis of a first phase difference signal output from the first imaging portion 601B (near point image circle), the control unit 54 calculates an interval between two images for a near point (Step S501).

Subsequently, the control unit 54 calculates AF evaluation values for the near point (Step S502) and obtains an optical path length difference (Step S503).

Subsequently, the control unit 54 determines whether or not the defocus amount (first defocus amount) of the AF evaluation values and the optical path length difference are of the same sign and the defocus amount (first defocus amount) has an absolute value less than the optical path length difference ("defocus amount (first defocus amount)" <"optical path length difference") (Step S504). In a case where the control unit 54 has determined that the defocus amount (first defocus amount) of the AF evaluation values and the optical path length difference are of the same sign and the defocus amount (first defocus amount) has an absolute value less than the optical path length difference (Step S504: Yes), the control unit 54 determines that the optical system 243 is focused on a far point image circle at the second imaging portion 602A (Step S505). In this case, without driving the driver 245, the control unit 54 performs control of maintaining the current position of the focus lens 243a on the optical axis O1. After Step S505, the endoscope system 1B returns to the main routine in FIG. 40.

At Step S504, in a case where the control unit 54 has determined that the defocus amount (first defocus amount) of the AF evaluation values is of the same sign as the optical path length difference and the defocus amount (first defocus amount) has an absolute value not less than the optical path length difference (Step S504: No), the control unit 54 causes, on the basis of the defocus amount (first defocus amount), optical path length difference, and defocus direction at the first imaging portion 601A, the focus lens 243a of the optical system 243 to move along the optical axis O1 (Step S506). After Step S506, the endoscope system 1B returns to the main routine in FIG. 34.

Figure 40:
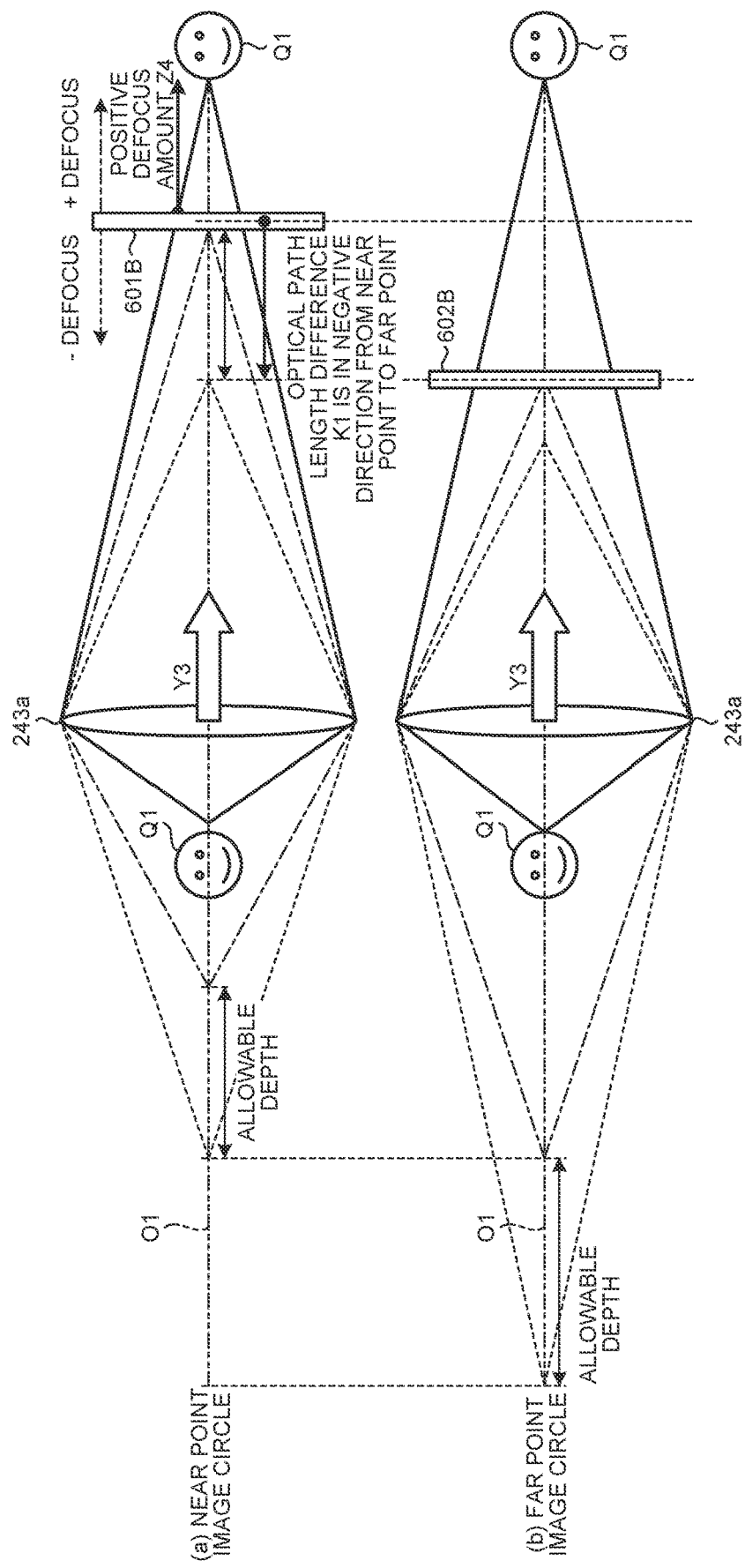
FIG. 40 is a diagram schematically illustrating a focusing state of the optical system in a case where a defocus amount of AF evaluation values and an optical path length difference are of different signs.

FIG. 40 is a diagram schematically illustrating a focusing state of the optical system 243 in a case where the defocus amount of the AF evaluation values and the optical path length difference are of different signs.

As illustrated in FIG. 40, in a case where a defocus amount Z4 (first defocus amount) and the optical path length difference K1 are of different signs (the optical path length difference K1 is in a negative direction from the near point to the far point), the control unit 54 drives the driver 245 to thereby cause the focus lens 243*a* of the optical system 243 to move along the optical axis O1 to the image side (arrow Y3) by the defocus amount Z4 (first defocus amount) of the AF evaluation values.

Furthermore, in a case where the defocus amount Z4 (first defocus amount) of the AF evaluation values and the optical path length difference K1 are of the same sign (the optical path length difference K1 is in the negative direction from the near point to the far point) and the defocus amount Z4 has an absolute value equal to or more than the optical path length difference K1 (Z4 K1), the control unit 54 drives the driver 245 to thereby cause the focus lens 243*a* of the optical system 243 to move along the optical axis O1 to the object side by the absolute value of a difference between the defocus amount Z4 of the first imaging portion 601B and the optical path length difference K1.

As described above, in a case where the second reliability of the second phase difference signal output from the second phase difference pixels 72B of the second imaging portion 602B is not equal to or higher than the first reliability, the control unit 54 performs the AF process for the subject Q1 by controlling the position of the focus lens 243*a* of the optical system 243, on the basis of the defocus direction (first defocus direction) and defocus amount (first defocus amount) of the AF evaluation values at the first imaging portion 601B (near point image circle) and the optical path length difference.

In the above described second embodiment, the control unit 54 obtains the optical path length difference between the first optical path and the second optical path, calculates the first reliability of the first phase difference signal detected by the first phase difference pixels 71B, calculates the second reliability of the second phase difference signal detected by the second phase difference pixels 72B, compares the first reliability to the second reliability, calculates the AF evaluation values on the basis of the second phase difference signal in a case where the second reliability is equal to or higher than the first reliability, calculates the AF evaluation values on the basis of the first phase difference signal in a case where the second reliability is not equal to or higher than the first reliability, and drives the driver 245 on the basis of the optical path length difference and AF evaluation values, to cause the optical system 243 to be focused on the object. In this case, the first phase difference pixels 71B and the second phase difference pixels 72B have pupil division directions different from each other for their light shielding PDs arranged therein. Therefore, on the basis of the AF evaluation values that enable detection of the optimum focus position for a subject, the AF evaluation values being those of either the first phase difference pixels 71B or the second phase difference pixels 72B, the control unit 54 drives the driver 245 to cause the optical system 243 to be focused on the object. As compared to a case where PDs having different pupil division directions are arranged in one of the first imaging portion 601B and the second imaging portion 602B, the defective pixel density is able to be reduced and vertical and horizontal lines are able to be detected simultaneously. As a result, even in a case where the optical system 243 that is a space division EDOF optical system, the first phase difference pixels 71B, and the second phase difference pixels 72B are used, the AF precision is able to be improved.

First Modified Example of Second Embodiment

A first modified example of the second embodiment will be described next. An endoscope system according to the first modified example of the second embodiment has first and second imaging portions configured differently from the above described first imaging portion 601B and second imaging portion 602B according to the second embodiment. The first imaging portion and second imaging portion according to the first modified example of the second embodiment will be described hereinafter. The same reference signs will be assigned to components that are the same as those of the above described endoscope system 1B according to the second embodiment, and detailed description thereof will be omitted.

Figure 41:
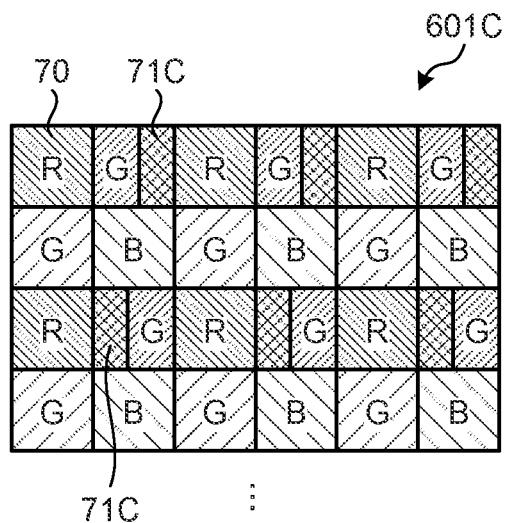
FIG. 41 is a diagram schematically illustrating a first imaging portion according to a first modified example of the second embodiment.
Figure 42:
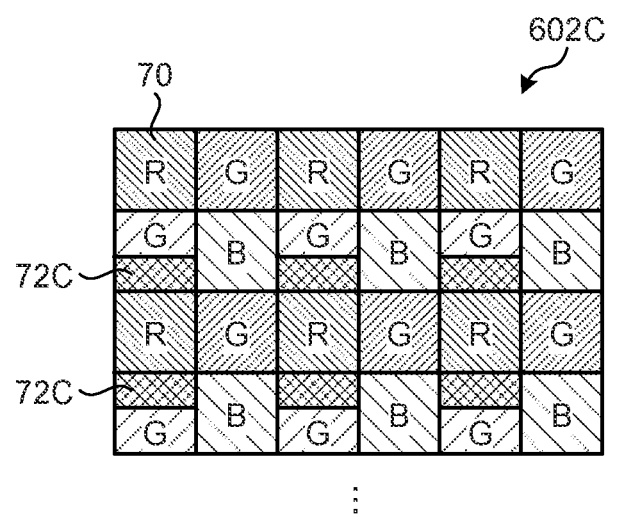
FIG. 42 is a diagram schematically illustrating a second imaging portion according to the first modified example of the second embodiment.

FIG. 41 is a diagram schematically illustrating the first imaging portion according to the first modified example of the second embodiment. FIG. 42 is a diagram schematically illustrating the second imaging portion according to the first modified example of the second embodiment. A first imaging portion 601C and a second imaging portion 602C illustrated in FIG. 41 and FIG. 42 have been integrally formed in an imaging element 244, but without being limited to this example, they may be formed to be separately bodied.

As illustrated in FIG. 41 and FIG. 42, in the first imaging portion 601C and the second imaging portion 602C, phase difference pixels 71 of first phase difference pixels 71C of a PD light shielding type and phase difference pixels 71 of second phase difference pixels 72C of the PD light shielding type are arranged at positions different from each other. Specifically, in the first imaging portion 601C and the second imaging portion 602C, the first phase difference pixels 71C of the PD light shielding type and the second phase difference pixels 72C of the PD light shielding type are arranged to be at positions different from each other, in a case where the first imaging portion 601C and the second imaging portion 602C are superimposed on each other with reference to a predetermined pixel.

Furthermore, the first phase difference pixels 71C and the second phase difference pixels 72C are arranged orthogonally to each other so that the pupil division direction of a first light beam and the pupil division direction of a second light beam differ from each other. Therefore, the image processing unit 51 interpolates pixel values for the first phase difference pixels 71C or second phase difference pixel 72C by using pixel values of imaging pixels 70 of the other imaging portion (the second imaging portion 602C or the first imaging portion 601C), the imaging pixels 70 corresponding to positions at which the first phase difference pixels 71C or the second phase difference pixels 72C are arranged.

In the first modified example of the second embodiment described above, the first phase difference pixels 71C of the PD light shielding type in the first imaging portion 601C and the second phase difference pixels 72C of the PD light shielding type in the second imaging portion 602C are arranged at positions different from each other. Therefore, the image processing unit 51 is able to interpolate pixel values for the first phase difference pixels 71C or second phase difference pixels 72C of the PD light shielding type, the first and second phase difference pixels 71C and 72C being defective pixels, by using the pixel values of the imaging pixels 70 of the other imaging portion (the second imaging portion 602C or the first imaging portion 601C), the imaging pixels 70 corresponding to positions at which the first phase difference pixels 71C or the second phase difference pixels 72C are arranged, the imaging pixels 70 not being defective pixels.

Furthermore, the first modified example of the second embodiment enables improvement of image quality because the first phase difference pixels 71C in the first imaging portion 601C and the second phase difference pixels 72C in the second imaging portion 602C are able to be arranged less densely.

Second Modified Example of Second Embodiment

Figure 43:
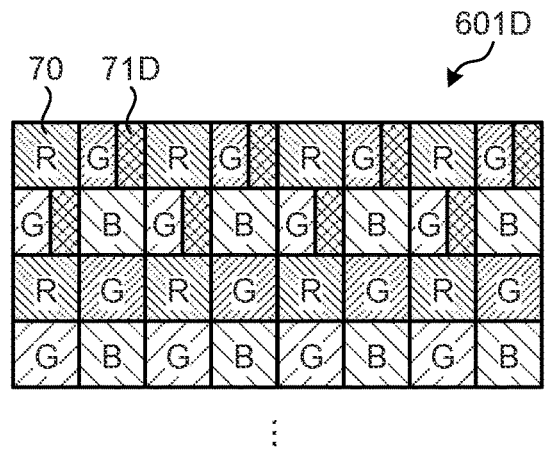
FIG. 43 is a diagram schematically illustrating a first imaging portion according to a second modified example of the second embodiment.
Figure 44:
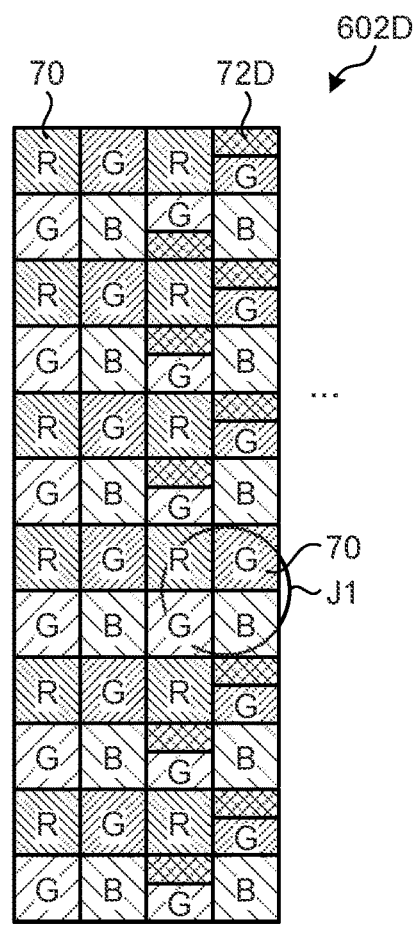
FIG. 44 is a diagram schematically illustrating a second imaging portion according to the second modified example of the second embodiment.
Figure 45:
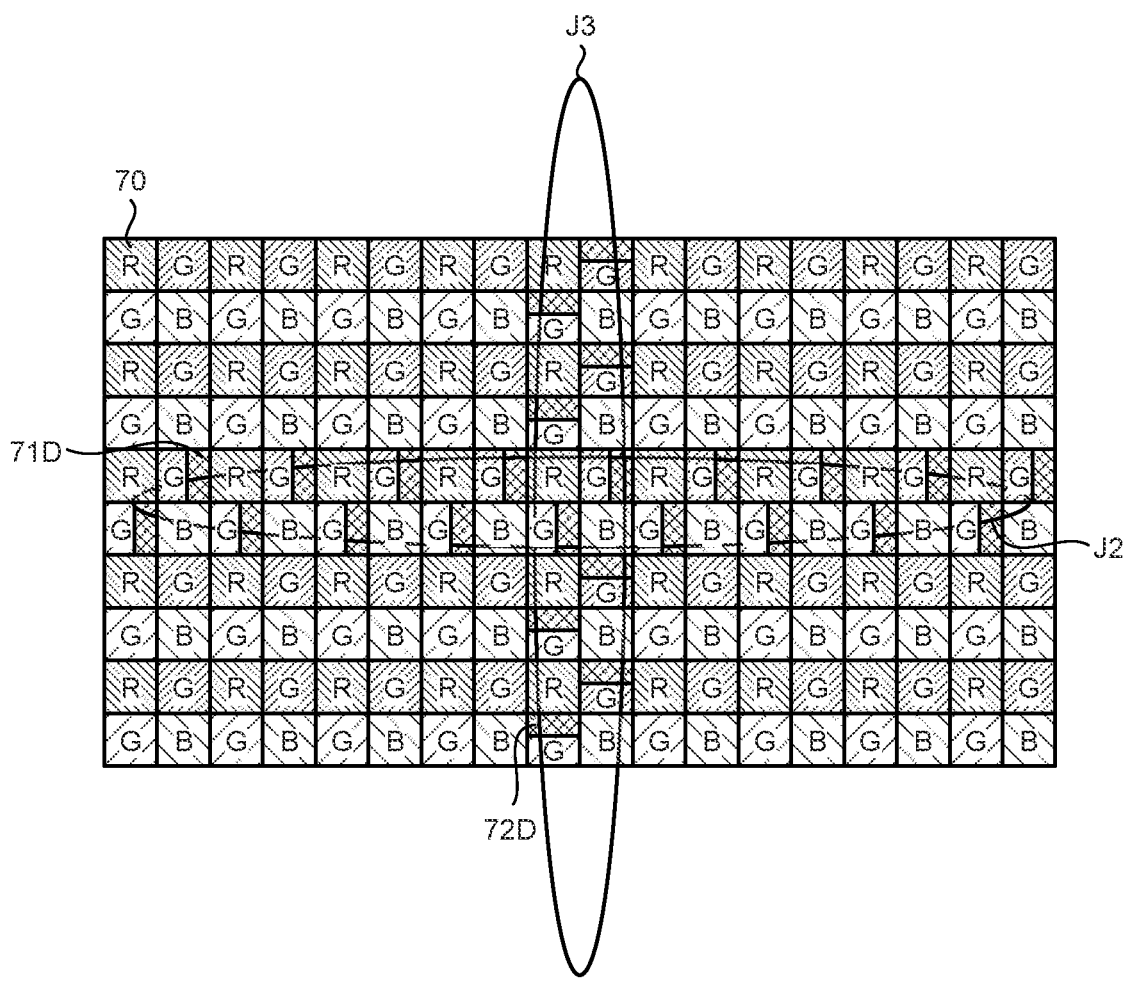
FIG. 45 is a diagram schematically illustrating a state in which the first imaging portion and the second imaging portion have been virtually superimposed on each other.

A second modified example of the second embodiment will be described next. FIG. 43 is a diagram schematically illustrating a first imaging portion according to the second modified example of the second embodiment. FIG. 44 is a diagram schematically illustrating a second imaging portion according to the second modified example of the second embodiment. FIG. 45 is a diagram schematically illustrating a state in which the first imaging portion and the second imaging portion have been superimposed on each other virtually. A first imaging portion 601D and a second imaging portion 602D illustrated in FIG. 43 and FIG. 44 have been integrally formed in an imaging element 244, but without being limited to this example, they may be formed to be separately bodied.

As illustrated in FIG. 43 to FIG. 45, first phase difference pixels 71D and second phase difference pixels 72D of the first imaging portion 601D and the second phase difference pixels 72D of the second imaging portion 602D are arranged to be orthogonal to each other. Furthermore, as illustrated in FIG. 43 to FIG. 45, at positions where any of the first phase difference pixels 71D of the first imaging portion 601D and any of the second phase difference pixels 72D of the second imaging portion 602D overlap each other, only the overlapping first phase difference pixels 71D or only the overlapping second phase difference pixels 72D are provided.

In the second modified example of the second embodiment described above, the first phase difference pixels 71D of a PD light shielding type and the second phase difference pixels 72D of the PD light shielding type of the first imaging portion 601D and the second imaging portion 602D are arranged at positions different from each other. Therefore, the image processing unit 51 is able to perform interpolation by using pixel values of imaging pixels 70 of the other imaging portion (the second imaging portion 602D or first imaging portion 601D), the imaging pixels 70 corresponding to positions at which the first phase difference pixels 71D or second phase difference pixels 72D of the PD light shielding type that are defective pixels are arranged, the imaging pixels 70 not being defective pixels.

Furthermore, the second modified example of the second embodiment enables improvement of image quality because the first phase difference pixels 71D in the first imaging portion 601D and the second phase difference pixels 72D in the second imaging portion 602D are able to be arranged less densely.

Third Modified Example of Second Embodiment

Figure 46:
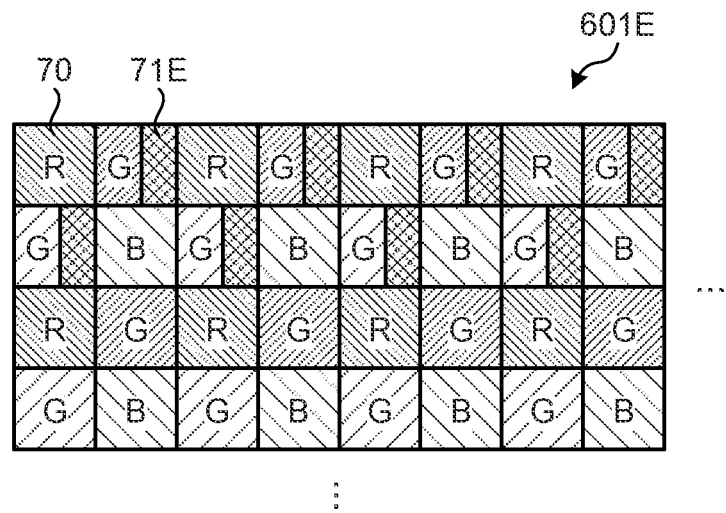
FIG. 46 is a diagram schematically illustrating a first imaging portion according to a third modified example of the second embodiment.
Figure 47:
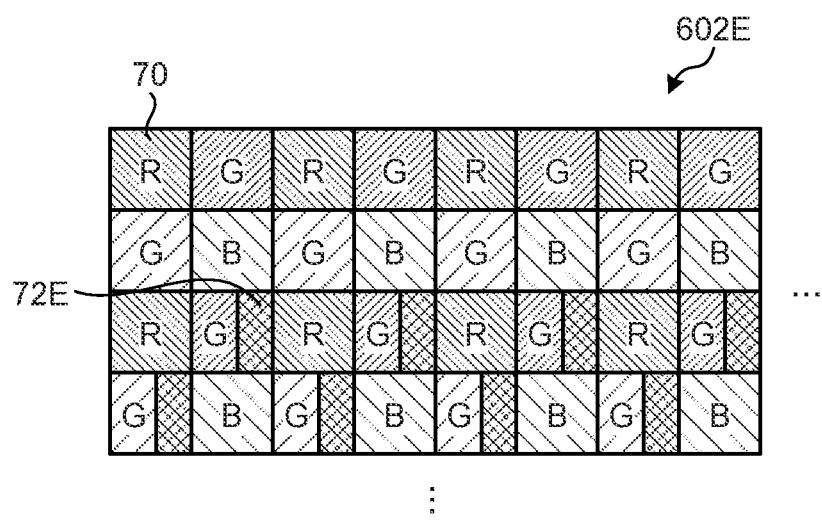
FIG. 47 is a diagram schematically illustrating a second imaging portion according to the third modified example of the second embodiment.

A third modified example of the second embodiment will be described next. FIG. 46 is a diagram schematically illustrating a first imaging portion according to the third modified example of the second embodiment. FIG. 47 is a diagram schematically illustrating a second imaging portion according to the third modified example of the second embodiment. A first imaging portion 601E and a second imaging portion 602E illustrated in FIG. 46 and FIG. 47 have been integrally formed in an imaging element 244, but without being limited to this example, they may be formed to be separately bodied.

As illustrated in FIG. 46 and FIG. 47, first phase difference pixels 71E and second phase difference pixels 72E of the first imaging portion 601E and the second imaging portion 602E are arranged at positions where the first phase difference pixels 71E and second phase difference pixels 72E do not overlap each other in a case where the first imaging portion 601E and the second imaging portion 602E have been superimposed on each other with reference to a predetermined pixel. For example, the first phase difference pixels 71E and second phase difference pixels 72E of the first imaging portion 601E and the second imaging portion 602E are alternately arranged, each in units of two rows.

In the third modified example of the second embodiment described above, the first phase difference pixels 71E of a PD light shielding type and the second phase difference pixels 72E of the PD light shielding type of the first imaging portion 601E and the second imaging portion 602E are arranged at positions different from each other. Therefore, the image processing unit 51 is able to interpolate pixel values of the first phase difference pixels 71E of the PD light shielding type or second phase difference pixels 72D of the PD light shielding type by using pixel values of imaging pixels 70 of the other imaging portion (second imaging portion 602E or first imaging portion 601E), the first phase difference pixel 71E and second phase difference pixels 72E being defective pixels, the imaging pixels 70 corresponding to positions at which the first phase difference pixel 71E or second phase difference pixels 72E are arranged, the imaging pixels 70 not being defective pixels.

Furthermore, the third modified example of the second embodiment enables improvement of image quality because the first phase difference pixels 71E in the first imaging portion 601E and the second phase difference pixels 72E in the second imaging portion 602E are able to be arranged less densely.

Fourth Modified Example of Second Embodiment

Figure 48:
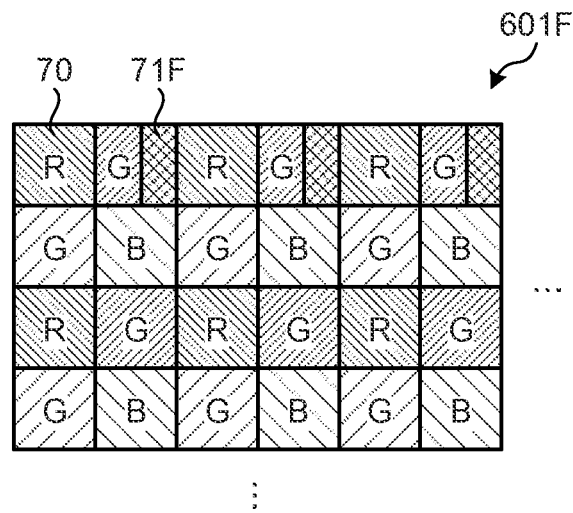
FIG. 48 is a diagram schematically illustrating a first imaging portion according to a fourth modified example of the second embodiment.
Figure 49:
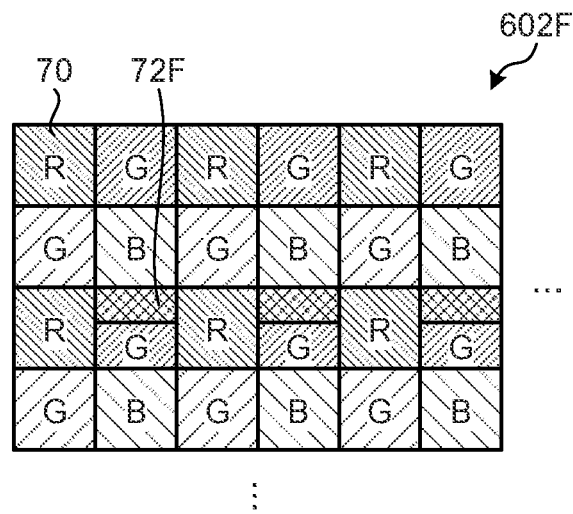
FIG. 49 is a diagram schematically illustrating a second imaging portion according to the fourth modified example of the second embodiment.

A fourth modified example of the second embodiment will be described next. FIG. 48 is a diagram schematically illustrating a first imaging portion according to the fourth modified example of the second embodiment. FIG. 49 is a diagram schematically illustrating a second imaging portion according to the fourth modified example of the second embodiment. A first imaging portion 601F and a second imaging portion 602F illustrated in FIG. 48 and FIG. 49 have been integrally formed in an imaging element 244, but without being limited to this example, they may be formed to be separately bodied.

As illustrated in FIG. 48 and FIG. 49, first phase difference pixels 71F and second phase difference pixels 72F of the first imaging portion 601F and the second imaging portion 602F are arranged so that the first phase difference pixels 71F and the second phase difference pixels 72F will be orthogonal to each other in a case where the first imaging portion 601F and the second imaging portion 602F are superimposed on each other virtually with reference to a predetermined pixel.

In the fourth modified example of the second embodiment described above, the first phase difference pixels 71F of a PD light shielding type and the second phase difference pixels 72F of the PD light shielding type of the first imaging portion 601F and the second imaging portion 602F are arranged at positions different from each other. Therefore, the image processing unit 51 is able to interpolate pixel values of the first phase difference pixels 71D of the PD light shielding type or the second phase difference pixels 72F of the PD light shielding type, the first phase difference pixels 71F and second phase difference pixels 72F being defective pixels, by using pixel values of imaging pixels 70 of the other imaging portion (the second imaging portion 602F or first imaging portion 601F), the imaging pixels 70 corresponding to positions at which the first phase difference pixels 71F or second phase difference pixels 72F are arranged, the imaging pixels 70 not being defective pixels.

Furthermore, in the fourth modified example of the second embodiment, pupil division directions of the light shielding PDs arranged in the first phase difference pixels 71F and second phase difference pixels 72F are orthogonal to each other. Therefore, on the basis of AF evaluation values that enable detection of the optimum focus position for a subject, the AF evaluation values being those of either the first phase difference pixels 71F or the second phase difference pixels 72F, the control unit 54 drives the driver 245 to cause the optical system 243 to be focused on the object. As compared to a case where PDs having different pupil division directions are arranged in one of the first imaging portion 601F and the second imaging portion 602F, the defective pixel densities are able to be reduced and vertical and horizontal lines are able to be detected simultaneously. As a result, even in a case where the optical system 243 that is a space division EDOF optical system, the first phase difference pixels 71F, and the second phase difference pixels 72F are used, the AF precision is able to be improved.

Fifth Modified Example of Second Embodiment

Figure 50:
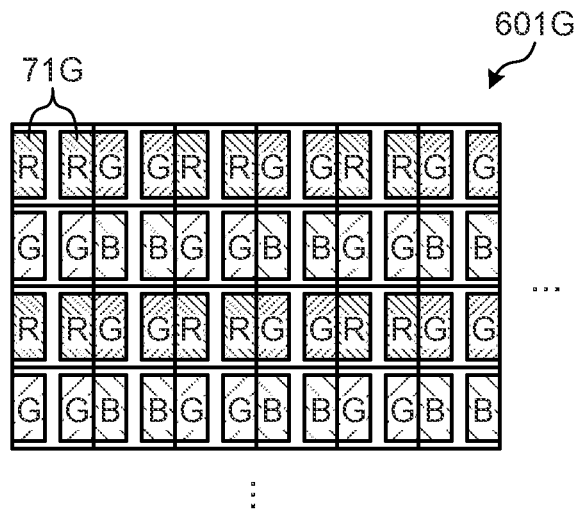
FIG. 50 is a diagram schematically illustrating a first imaging portion according to a fifth modified example of the second embodiment.
Figure 51:
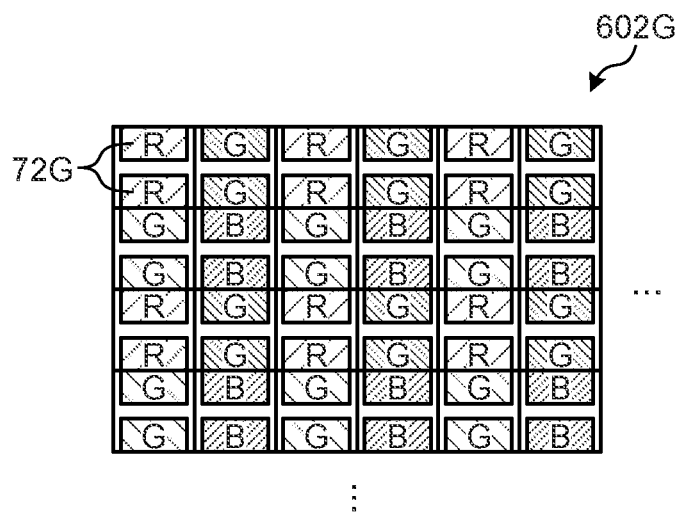
FIG. 51 is a diagram schematically illustrating a second imaging portion according to the fifth modified example of the second embodiment.

A fifth modified example of the second embodiment will be described next. FIG. 50 is a diagram schematically illustrating a first imaging portion according to the fifth modified example of the second embodiment. FIG. 51 is a diagram schematically illustrating a second imaging portion according to the fifth modified example of the second embodiment. A first imaging portion 601G and a second imaging portion 602G illustrated in FIG. 50 and FIG. 51 have been integrally formed in an imaging element 244, but without being limited to this example, they may be formed to be separately bodied.

As illustrated in FIG. 50 and FIG. 51, the first imaging portion 601G and the second imaging portion 602G have first phase difference pixels 71G and second phase difference pixels 72G that are PD division phase difference pixels each including plural photodiodes that individually receive a pair of light beams resulting from pupil division of a first light beam or second light beam. Furthermore, the first phase difference pixels 71G and second phase difference pixels 72G in the first imaging portion 601G and the second imaging portion 602G are arranged to be respectively orthogonal to each other.

Figure 52:
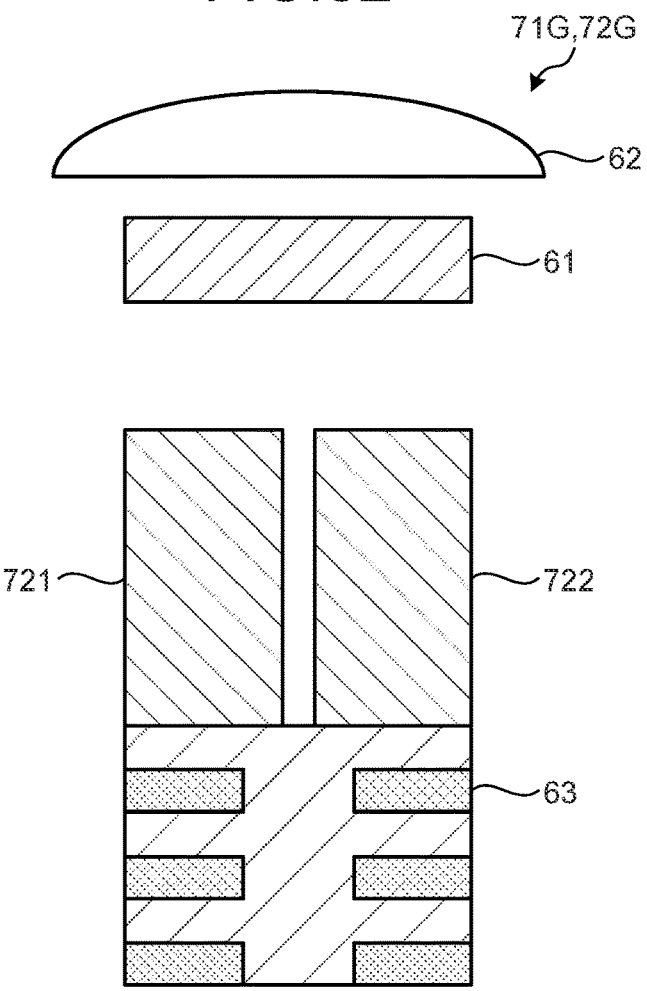
FIG. 52 is a sectional view of a first phase difference pixel according to the fifth modified example of the second embodiment.
Figure 53:
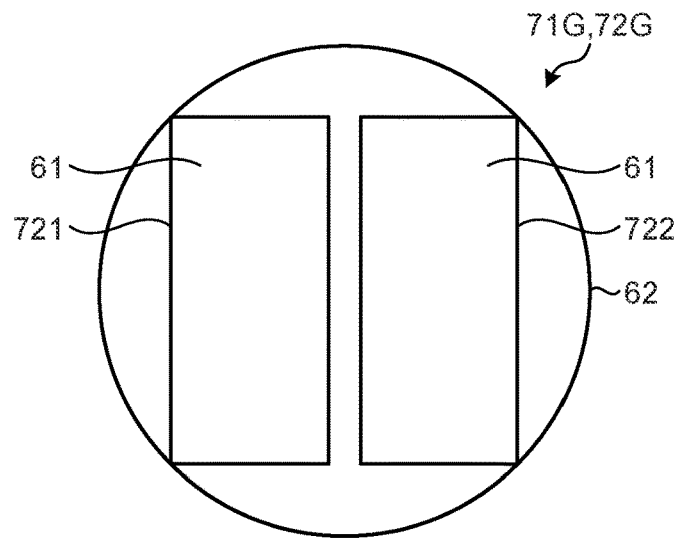
FIG. 53 is a top view of the first phase difference pixel according to the fifth modified example of the second embodiment.

FIG. 52 is a sectional view of the first phase difference pixel 71G. FIG. 53 is a top view of the first phase difference pixel 71G. The first phase difference pixel 71G of the PD division type illustrated in FIG. 52 and FIG. 53 has: two light receiving units 721 and 722 that function as photoelectric conversion elements, the two light receiving units 721 and 722 each including, for example, a photodiode; a color filter 61; and a microlens 62 that have been layered over one another in this order. Furthermore, a reading unit 63 is formed to be layered over the two light receiving units 721 and 722, on a bottom surface side of the two light receiving units 721 and 722.

The first phase difference pixel 71G configured as described above generates a pair of a phase difference signal and an image signal, for adjustment and distance measurement of a focal position, and outputs these phase difference signal and image signal.

In this fifth modified example of the second embodiment described above, pupil division directions of the PD division type are oriented differently between the first phase difference pixels 71G and the second phase difference pixels 72G. Therefore, on the basis of AF evaluation values that enable detection of the optimum focus position for a subject, the AF evaluation values being those of either the first phase difference pixels 71G or the second phase difference pixels 72G, the control unit 54 drives the driver 245 to cause the optical system 243 to be focused on the object. As a result, as compared to a case where PDs having different pupil division directions are arranged in any one of the first imaging portion 601G and the second imaging portion 602G, reduction of the dynamic range is able to be minimized, simultaneous detection of vertical and horizontal lines are enabled, and AF precision is able to be improved.

Other Embodiments

Various embodiments may be formed by combination, as appropriate, of plural components disclosed with respect to the above described endoscope systems according to the first and second embodiments of the present disclosure. For example, some of the components described with respect to the endoscope system according to the above described first or second embodiment of the present disclosure may be eliminated. Furthermore, any components described with respect to the endoscope systems according to the above described embodiments of the present disclosure may be combined as appropriate.

Furthermore, the "units" or the "portions" described above with respect to the endoscope systems according to the first and second embodiments of the present disclosure may be read, for example, as "means" or "circuits". For example, a control unit may be read as a control means or a control circuit.

Furthermore, a program to be executed by the endoscope system according to the first or second embodiment of the present disclosure may be provided as file data in an installable format or executable format, by being recorded in a computer readable recording medium, such as a CD-ROM, a flexible disk (FD), a CD-R, a digital versatile disk (DVD), a USB medium, or a flash memory.

Furthermore, a program to be executed by the endoscope system according to the first or second embodiment of the present disclosure may be configured to be stored on a computer connected to a network, such as the Internet, and to be provided by being downloaded via the network.

In the description of the flowcharts in this specification, the order of the steps in each process is disclosed by use of expressions, such as "firstly", "thereafter", and "subsequently", but the sequence in each process needed for implementation of the disclosure is not uniquely defined by these expressions. That is, the sequences of each process in the flowcharts described in this specification may be modified as far as no contradiction arises from the modification.

What is achieved according to the present disclosure is an effect of preventing image quality degradation and enabling improvement of AF precision, even in a case where a space division EDOF optical system and phase difference pixels for autofocus are used.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging system, comprising:
an optical system including an optical path splitter, the optical system being configured to form a subject image of an object to a near point image circle and a far point image circle by the optical path splitter, the far point image circle being in a different position from the near point image circle;
a driver configured to drive the optical system along an optical axis;
an imaging element configured to capture the subject image and generate image data; and
a processor configured to control the imaging element and the driver,
the imaging element comprising:
a first imaging portion that includes plural pixels each having a photoelectric converter, the first imaging portion being configured to capture the near point image circle formed by an image of a first light beam that travels through a first optical path in the optical system;
a second imaging portion that includes plural pixels each having a photoelectric converter, the plural pixels being arranged in a two-dimensional matrix, the second imaging portion being configured to capture the far point image circle formed by an image of a second light beam that travels, via part of the first optical path, through a second optical path shorter than the first optical path; and
plural phase difference pixels for phase difference autofocus, the plural phase difference pixels being arranged in at least one of the first imaging portion and the second imaging portion, the plural phase difference pixels being arranged at positions different from each other when the first imagining portion and the second imagining portion are superimposed on each other, the plural phase difference pixels being configured to output phase difference signals by receiving a pair of light beams resulting from pupil division of a light beam that passes through the optical system, and
the processor being configured to
calculate an interval between two images based on the phase difference signal,
generate a combined image resulting from combination of a first image obtained by the first imaging portion and a second image obtained by the second imaging portion, and
drive the driver to cause the optical system to be focused on the object for the combined image based on the interval between two images.

2. The imaging system according to claim 1, wherein the optical system comprises:
a lens group configured to form the subject image of the object; and
the optical path splitter including an optical path splitter element that is arranged on an optical path of the lens group and on an image side of the lens group and includes an optical path splitter surface configured to split an image of the object incident via the lens group into the first optical path and the second optical path,
the second optical path is formed on an extension of the optical path of the lens group,
the first optical path is formed to intersect the second optical path, and
the sum total of the number of times transmission of the first optical beam that travels through the first optical path occurs and the number of times reflection of the first optical beam occurs is more than the sum total of the number of times transmission of the second optical beam that travels through the second optical path occurs and the number of times reflection of the second light beam occurs.

3. The imaging system according to claim 1, wherein the processor is configured to
determine whether or not reliability of the phase difference signals is equal to or higher than a predetermined threshold,
when it is determined that the reliability is equal to or higher than the predetermined threshold, calculate the interval between two images, and
when it is determined that the reliability is not equal to or higher than the predetermined threshold, drive the driver to cause a focus state of the optical system to be changed until the reliability is determined to be equal to or higher than the predetermined threshold.

4. The imaging system according to claim 1, wherein
the interval between two images represents a distance on an imaging surface of the imaging element, the distance being a distance between two subject images in a pupil division direction of at least one of the first light beam and the second light beam, and
the processor is configured to calculate a defocus amount and a defocus direction based on the interval between two images.

5. The imaging system according to claim 1, wherein
the plural phase difference pixels for phase difference autofocus include:
a first phase difference pixel that is arranged in the first imaging portion, the first phase difference pixel being configured to output a first phase difference signal for detection of the object; and
a second phase difference pixel that is arranged in the second imaging portion, the second phase difference pixel being configured to output a second phase difference signal for detection of the object, and
the processor is configured to
obtain an optical path length difference between the first optical path and the second optical path,
calculate, based on the first phase difference signal, first reliability of the first phase difference signal detected by the first phase difference pixel,
calculate, based on the second phase difference signal, second reliability of the second phase difference signal detected by the second phase difference pixel,
compare the first reliability and the second reliability to each other,
calculate the interval between two images based on the second phase difference signal when the second reliability is equal to or higher than the first reliability,
calculate the interval between two images based on the first phase difference signal when the second reliability is not equal to or higher than the first reliability, and drive the driver to cause the optical system to be focused on the object based on the optical path length difference and the interval between two images.

6. The imaging system according to claim 5, wherein the processor is configured to
calculate a first interval between two images based on the first phase difference signal, the first interval representing a distance on an imaging surface of the imaging element, the distance being a distance between two subject images in a pupil division direction of the first light beam,
calculate a first defocus amount and a first defocus direction based on the first interval between two images,
calculate a second interval between two images based on the second phase difference signal, the second interval representing a distance on the imaging surface of the imaging element, the distance being a distance between two subject images in a pupil division direction of the second light beam, and
calculate a second defocus amount and a second defocus direction based on the second interval between two images.

7. The imaging system according to claim 6, wherein the processor is configured to
when the second reliability is equal to or higher than the first reliability and further the second defocus direction is to an image side and the second defocus amount has an absolute value not less than the optical path length difference, perform control of causing the optical system to move to the image side by an absolute value of a difference between the second defocus amount and the optical path length difference,
when the second reliability is equal to or higher than the first reliability and further the second defocus direction is to an image side and the second defocus amount has an absolute value less than the optical path length difference, perform control of maintaining position of the optical system,
when the second reliability is equal to or higher than the first reliability and further the second defocus direction is to an object side, perform control of causing the optical system to move to an image side by the second defocus amount,
when the second reliability is not equal to or higher than the first reliability and further the first defocus direction is to an image side, perform control of causing the optical system to move to the image side by the first defocus amount,
when the second reliability is not equal to or higher than the first reliability and further the first defocus direction is to an object side and the first defocus amount is not less than the optical path length difference, perform control of causing the optical system to move to the object side by an absolute value of a difference between the first defocus amount and the optical path length difference, and
when the second reliability is not equal to or higher than the first reliability and further the first defocus direction is to an object side and the first defocus amount is less than the optical path length difference, perform control of maintaining the position of the optical system.

8. The imaging system according to claim 5, wherein a pupil division direction of the first light beam and a pupil division direction of the second light beam are different from each other.

9. The imaging system according to claim 5, wherein each of the first phase difference pixel and the second phase difference pixel includes a light shield configured to block light, the light shield being on part of a light receiving surface of each of the first phase difference pixel and the second phase difference pixel.

10. The imaging system according to claim 5, wherein each of the first phase difference pixel and second phase difference pixel includes plural photodiodes configured to individually receive a pair of light beams resulting from pupil division of either the first light beam or the second light beam.

11. The imaging system according to claim 1, wherein
the first imaging portion and the second imaging portion have a same number of pixels and a same pixel size, and
an arrangement pattern of the first phase difference pixel in the first imaging portion is different from an arrangement pattern of the second phase difference pixel in the second imaging portion.

12. The imaging system according to claim 11, wherein the first phase difference pixel and the second phase difference pixel are arranged at positions different from each other when the first imaging portion and the second imaging portion are superimposed on each other with reference to a predetermined position.

13. The imaging system according to claim 1, wherein, the plural phase difference pixels are arranged in the first imaging portion and the second imaging portion.

14. An endoscope system, comprising:
an endoscope comprising an insertion portion to be inserted into a subject; and
a controller to which the endoscope is detachably connected,
the endoscope comprising:
an optical system including an optical path splitter, the optical system being configured to form a subject image of an object to a near point image circle and a far point image circle by the optical path splitter, the far point image circle being in a different position from the near point image circle;
a driver configured to drive the optical system along an optical axis; and
an imaging element configured to capture the subject image and generates image data,
the controller comprises a processor configured to control the imaging element and the driver,
the imaging element comprising:
a first imaging portion that includes plural pixels each having a photoelectric converter, the plural pixels being arranged in a two-dimensional matrix, the first imaging portion being configured to capture the near point image circle formed by an image of a first light beam that travels through a first optical path in the optical system;
a second imaging portion that includes plural pixels each having a photoelectric converter, the plural pixels being arranged in a two-dimensional matrix, the second imaging portion being configured to capture the far point image circle formed by an image of a second light beam that travels, via part of the first optical path, through a second optical path shorter than the first optical path; and
plural phase difference pixels for phase difference autofocus, the plural phase difference pixels being arranged in at least one of the first imaging portion and the second imaging portion, the plural phase difference pixels being arranged at positions different from each other when the first imagining portion and the second imagining portion are superimposed on each other, the plural phase difference pixels being configured to output phase difference signals that are able to be used in detection of the object by receiving a pair of light beams resulting from pupil division of a light beam that passes through the optical system, and the processor being configured to
- calculate an interval between two images based on the phase difference signal,
- generate a combined image resulting from combination of a first image obtained by the first imaging portion and a second image obtained by the second imaging portion, and
- drive the driver to cause the optical system to be focused on the object for the combined image based on the interval between two images.

15. The endoscope system according to claim 14, wherein the endoscope is a flexible endoscope or a rigid endoscope.

16. A control method executed by a controller configured to control an imaging device comprising: an optical system including an optical path splitter, the optical system being configured to form a subject image of an object to a near point image circle and a far point image circle by the optical path splitter, the far point image circle being in a different position from the near point image circle; a driver configured to drive the optical system along an optical axis; and an imaging element configured to capture the subject image and generate image data, the imaging element including: a first imaging portion that includes plural pixels each having a photoelectric converter, the plural pixels being arranged in a two-dimensional matrix, the first imaging portion being configured to capture the near point image circle formed by an image of a first light beam that travels through a first optical path in the optical system; a second imaging portion that includes plural pixels each having a photoelectric converter, the plural pixels being arranged in a two-dimensional matrix, the second imaging portion being configured to capture the far point image circle formed by an image of a second light beam that travels, via part of the first optical path, through a second optical path shorter than the first optical path; and plural phase difference pixels for phase difference autofocus, the plural phase difference pixels being arranged in at least one of the first imaging portion and the second imaging portion, the plural phase difference pixels being arranged at positions different from each other when the first imagining portion and the second imagining portion are superimposed on each other, the plural phase difference pixels being configured to output phase difference signals that are able to be used in detection of the object by receiving a pair of light beams resulting from pupil division of a light beam that passes through the optical system, the control method including:

calculating an interval between two images based on the phase difference signal;

generating a combined image resulting from combination of a first image obtained by the first imaging portion and a second image obtained by the second imaging portion; and driving the driver to cause the optical system to be focused on the object for the combined image based on the interval between two images.

\* \* \* \* \*